US009567374B2

(12) United States Patent
Pasquier et al.

(10) Patent No.: US 9,567,374 B2
(45) Date of Patent: Feb. 14, 2017

(54) METHOD FOR GENERATING CYAN FLUORESCENT PROTEINS WITH REDUCED PH SENSITIVITY

(75) Inventors: Hélène Pasquier, Montlhery (FR); Fabienne Merola, Gif s/Yvette (FR); Marie Erard, Gentilly (FR); Agathe Espagne, Paris (FR); Asma Fredj, Paris (FR)

(73) Assignees: CENTRE NATIONAL DE LA RECHERCHE SCIENTIFIQUE, Paris (FR); UNIVERWSITE PARIS-SUD 11, Orsay (FR)

( * ) Notice: Subject to any disclaimer, the term of this patent is extended or adjusted under 35 U.S.C. 154(b) by 0 days.

(21) Appl. No.: 14/126,183

(22) PCT Filed: Jun. 15, 2012

(86) PCT No.: PCT/EP2012/061530
§ 371 (c)(1),
(2), (4) Date: Dec. 13, 2013

(87) PCT Pub. No.: WO2012/172095
PCT Pub. Date: Dec. 20, 2012

(65) Prior Publication Data
US 2014/0106392 A1    Apr. 17, 2014

(30) Foreign Application Priority Data
Jun. 15, 2011 (FR) ...................... 11 55227

(51) Int. Cl.
*C07K 14/00* (2006.01)
*G01N 21/64* (2006.01)
*C07K 14/435* (2006.01)
*G01N 33/542* (2006.01)
*G01N 33/58* (2006.01)
*G01N 33/533* (2006.01)

(52) U.S. Cl.
CPC ....... *C07K 14/001* (2013.01); *C07K 14/43595* (2013.01); *G01N 21/6486* (2013.01); *G01N 33/533* (2013.01); *G01N 33/542* (2013.01); *G01N 33/582* (2013.01)

(58) Field of Classification Search
CPC ............ C07K 14/001; C07K 14/43595; G01N 21/6486; G01N 33/533; G01N 33/542; G01N 33/582
See application file for complete search history.

(56) References Cited

U.S. PATENT DOCUMENTS 7,015,310 B2*  3/2006  Remington et al. .......... 530/350
2005/0089908 A1*  4/2005  Piston et al. ..................... 435/6

FOREIGN PATENT DOCUMENTS

EP         2 189 528 A1    5/2010
WO    WO-2009/020197 A1   2/2009

OTHER PUBLICATIONS

Markwardt et al. (PLoS ONE, Mar. 2011, vol. 6 (3) e17896).*
Elsliger et al., "Structural and Spectral Response of Green Flourescent Protein Variants to Changes in pH," Biochemistry, 1999 vol. 38, No. 17, pp. 5296-5301.
Bizzarri et al., "Green Fluorescent protein based pH indicators for in vivo use: a review," Anal Bioannal Chem, 2009, vol. 393, pp. 1107-1122.
Boute et al., "The use of resonance energy transfer in high-throughput screening: BRET versus FRET," Trends in Pharmacological Sciences, 2002, vol. 23, No. 8, pp. 351-354.
Couprie et al., "First use of the UV Super-ACO free-electron laser: Fluorescence decays and rotational dynamics of the NADH coenzyme," Review of Scientific Instruments, 1994, vol. 65, No. 5, pp. 1485-1495.
Cubitt et al., "Understanding, improving and using green fluorescent proteins," Trends in Biochemical Science, 1995, vol. 20, No. 11, pp. 448-455.
Cubitt et al., "Understanding Structure—Function Relationships in the *Aequorea victoria* Green Fluorescent Protein," Methods in Cell Biology, 1999, vol. 58, pp. 19-30.
Day et al., "The fluorescent protein palette: tools for cellular imaging," Chemical Society Reviews, 2009, vol. 38, No. 10, pp. 2887-2921.
Dunn et al., "Imaging of cAMP Levels and Protein Kinase A Activity Reveals That Retinal Waves Drive Oscillations in Second-Messenger Cascades," The Journal of Neuroscience, 2006, vol. 26, No. 49, pp. 12807-12815.
Espagne et al., "Cyan Fluorescent Protein Carries a Constitutive Mutation That Prevents Its Dimerization," Biochemistry, 2011, vol. 50, No. 4, pp. 437-439.
Frommer et al., "Genetically encoded biosensors based on engineered fluorescent proteins," Chemical Society Review. 2009, vol. 38, No. 10, pp. 2833-2841.
Giuliani et al., "DISCO: a low-energy multipurpose beamline at synchrotron SOLEIL," Journal of Synchrotron Radiation, 2009, vol. 16, No. 6, pp. 835-841.
Goedhart et al., "Bright cyan fluorescent protein variants identified by fluorescence lifetime screening," Nature Methods, 2010, vol. 7, No. 2, pp. 137-139.
Griesbeck et al., "Reducing the Environmental Sensitivity of Yellow Fluorescent Protein," The Journal of Biological Chemistry, 2001, vol. 276, No. 31, pp. 29188-29194.
Heyduk, "Measuring protein conformational changes by FRET/LRET," Current Opinion in Biotechnology, 2002, vol. 13, pp. 292-296.
Issad et al., "Looking for an insulin pill? Use the BRET methodology!" Diabetes Metab., 2003, vol. 29, pp. 111-117.
Kelly et al., "How to study proteins by circular dichroism," Biochimica et Biophysica Acta, 2005, vol. 1751, pp. 119-139.

(Continued)

*Primary Examiner* — James H Alstrum Acevedo
*Assistant Examiner* — Tara Martinez
(74) *Attorney, Agent, or Firm* — Foley & Lardner LLP

(57) ABSTRACT

The present invention proposes a method for generating cyan fluorescent proteins which have reduced pH sensitivity, in particular acid-pH sensitivity.

11 Claims, 30 Drawing Sheets

(56) References Cited

OTHER PUBLICATIONS

Figure 1:
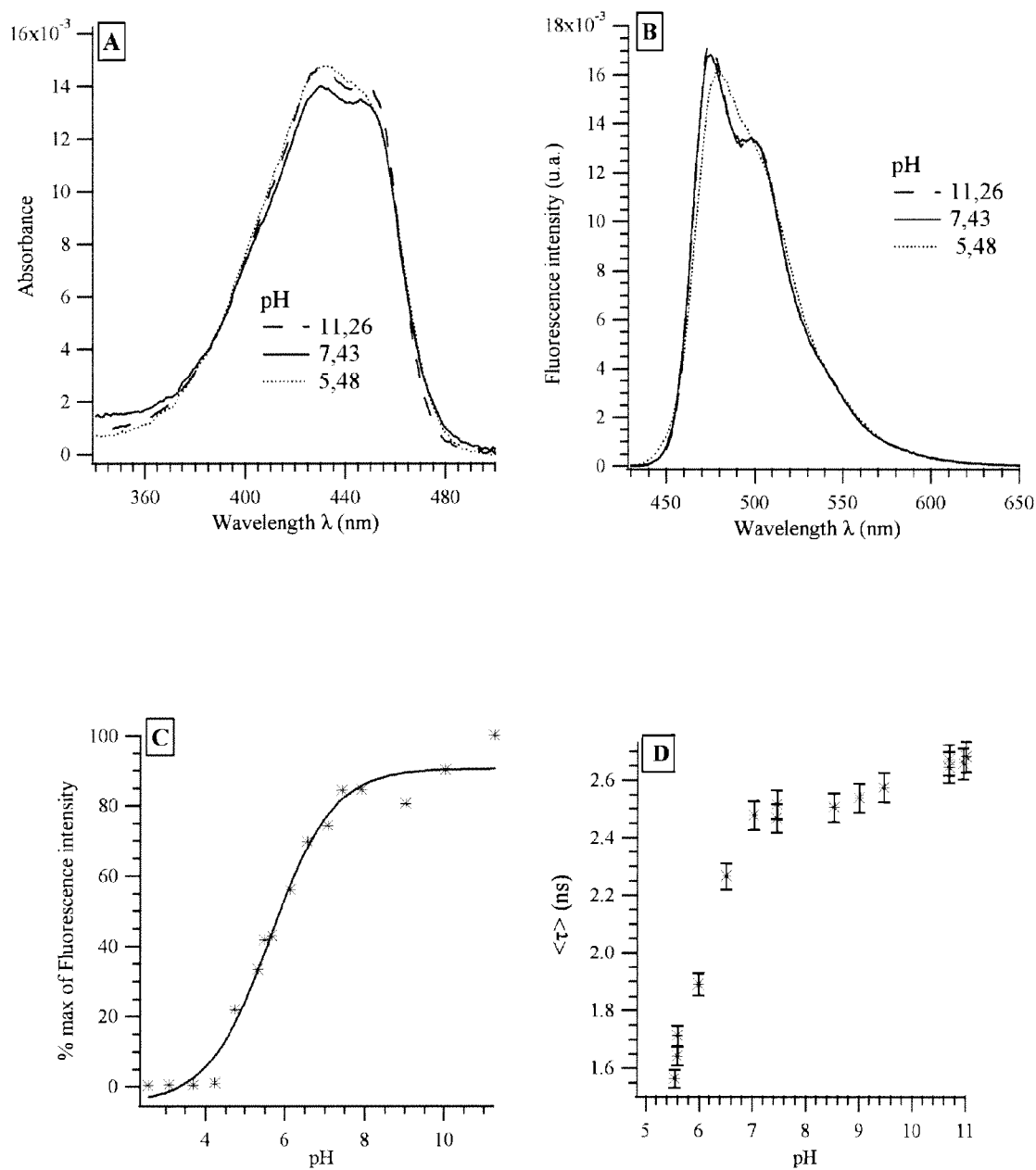

Kumar et al., "FLIM FRET Technology for Drug Discovery: Automated Multiwell-Plate High-Content Analysis, Multiplexed Readouts and Application in Situ," ChemPhysChem, 2011, vol. 12, pp. 609-626.
Lees et al., "A reference database for circular dichroism spectroscopy covering fold and secondary structure space," Bioinformatics, 2006, vol. 22, No. 16, pp. 1955-1962.
Lees et al., "CDtool—an integrated software package for circular dichroism spectroscopic data processing, analysis, and archiving," Analytical Biochemistry, 2004, vol. 332, pp. 285-289.
Llopis et al., "Measurement of cytosolic, mitochondrial, and Golgi pH in single living cells with green fluorescent proteins," Proc. Natl. Acad. Sci. USA, 1998, vol. 95, No. 12, pp. 6803-6808.
Malo et al., "X-ray Structure of Cerulean GFP: A Tryptophan-Based Chromophore Useful for Fluorescence Lifetime Imaging," Biochemistry, 2007, vol. 46, No. 35, pp. 9865-9873.
Mazzola et al., "Stability of Green Fluorescent Protein (GFP) in Chlorine Solutions of Varying pH," Biotechnol. Prog., 2006, vol. 22, pp. 1702-1707.
Merola et al., "Picosecond Tryptophan Fluorescence of Thioredoxin: Evidence for Discrete Species in Slow Exchange," Biochemistry, 1989, vol. 28, pp. 3383-3398.
Merzlyak et al., "Bright monomeric red fluorescent protein with an extended fluorescence lifetime," Nature Methods, 2007, vol. 4, No. 7, pp. 555-557.
Miyawaki et al., "Dynamic and quantitative $Ca^{2+}$ measurements using improved cameleons," Proc. Natl. Acad. Sci. USA, 1999, vol. 96, No. 5, pp. 2135-2140.
Miyawaki et al., "Monitoring Protein Conformations and Interactions by Fluorescence Resonance Energy Transfer between Mutants of Green Fluorescent Protein," Methods in Enzymology, 2000, vol. 327, pp. 472-499.
Morris et al., "Fluorescent Biosensors of Intracellular Targets from Genetically Encoded Reporters to Modular Polypeptide Probes," Cell Biochem Biophys, 2010, vol. 56, pp. 19-37.
Nagai et al., "A variant of yellow fluorescent protein with fast and efficient maturation for cell-biological applications," Nature Biotechnology, 2002, vol. 20, pp. 87-90.
Needleman et al., "A General Method Applicable to the Search for Similarities in the Amino Acid Sequence of Two Proteins," J. Mol. Biol., 1970., vol. 48, pp. 443-453.
Nguyen et al., "Evolutionary optimization of fluorescent proteins for intracellular FRET," Nature Biotechnology, 2005, vol. 23, No. 3, pp. 355-360.
Notification of Transmission of ISR and Written Opinion of the ISA International Searching or Declaration for International Application No. PCT/EP2012/061530 mailed Sep. 19, 2012, 6 pages.
Patterson et al., "Fluorescent protein spectra," Journal of Cell Science, 2001, vol. 114, No. 5, pp. 837-838.
Prasher et al., "Primary structure of the *Aequorea victoria* green-fluorescent protein," Gene, 1992, vol. 111, pp. 229-233.
Preliminary Search Report for French Application No. 115527 dated Jan. 9, 2012, 3 pages.
Rizzo et al., "An improved cyan fluorescent protein variant useful for FRET," Nature Biotechnology, 2004, vol. 22, No. 4, pp. 445-449 (1-5).
Sawano et al., "Directed evolution of green fluorescent protein by a new versatile PCR strategy for site-directed and semi-random mutagenesis," Nucleic Acids Research, 2000, vol. 28, No. 16, p. e78 (i-vii).
Seifert et al., "Backbone Dynamics of Green Fluorescent Protein and the Effect of Histidine 148 Substitution," Biochemistry, 2003, vol. 42, pp. 2500-2512.
Shaner et al., "A guide to choosing fluorescent proteins," Nature Methods, 2005, vol. 2, No. 12, pp. 905-909.
Shaner et al., "Advances in fluorescent protein technology," Journal of Cell Science, 2007, vol. 120, No. 24, pp. 4247-4260.
Tansila et al., "Rational Design of Analyte Channels of the Green Fluorescent Protein for Biosensor Applications," International Journal of Biological Sciences, 2007, vol. 3, No. 7, pp. 463-470.
Tomosugi et al., "An ultramarine fluorescent protein with increased photostability and pH insensitivity," Nature Methods, 2009, vol. 6, No. 5, pp. 351-353.
Tramier et al., "Picosecond-Hetero-FRET Microscopy to Probe Protein-Protein Interactions in Live Cells," Biophysical Journal, 2002, vol. 83, No. 6, pp. 3570-3577.
Trugnan et al., "FRAP, FLIP, FRET, BRET, FLIM, PRIM . . . De nouvelles techniques pour voir la vie en couleur!," Medicines/Sciences, 2004, vol. 20, pp. 1027-1034, with English Summary.
Truong et al., "The use of FRET imaging microscopy to detect protein-protein interactions and protein conformational changes in vivo," Current Opinion in Structural Biology, 2001, vol. 11, No. 5, pp. 573-578.
Whitmore et al., "DICHROWED, an online server for protein secondary structure analyses from circular dichroism spectroscopic data," Nucleic Acids Research, 2004, vol. 32, pp. W668-W673.
Wien et al., "Calcium Fluoride Micro Cells for Synchrotron Radiation Circular Dichroism Spectroscopy," Applied Spectroscopy, 2005, vol. 59, No. 9, pp. 1109-1113.
Zhang et al., "Genetically encoded reporters of protein kinase A activity reveal impact of substrate tethering," Proc Natl Acad Sci USA, 2001, vol. 98, pp. 14997-15002.
Zhang et al., "Insulin disrupts β-adrenergic signalling to protein kinase A in adipocytes," Nature, 2005, vol. 437, No. 22, pp. 569-573.

\* cited by examiner

| Proteins studied | ε (10³ M⁻¹ cm⁻¹) | Q.Yield | $\tau_L$ (ns) ± SD | $c_L$ (%) ± Dev Std | Photostability | | | in living cells |
|---|---|---|---|---|---|---|---|---|
| | | | | | on agarose beads | | | |
| | | | | | % Rev ± 2% | $\tau_{Rev}$ (s) ± 0.1s | $\tau_{Irrev}$ (s) ± 5% | $\tau_{Irrev}$ (s) ± Std Dev |
| ECFPr (SEQ ID N° 4) | 29 | 0,40 | 3,51 ± 0,12 | 52 ± 7 | 23 | 0.6 | 700 | 726 ± 88 (N=37) |
| ECFPr (65S) | 28,5 | 0,59 | 3,78 ± 0,11 | 77 ± 8 | 3 | 1 | 940 | 828 ± 89 (N=23) |
| ECFPr (72A, 145A, 148D) | 29,2 | 0,67 | 3,80 ± 0,13 | 64 ± 7 | 33 | 1 | 610 | 643 ± 97 (N=21) |
| ECFPr (65S, 72A, 145A, 148D) | 34,8 | 0,84 | 4,17 ± 0,09 | 83 ± 11 | 3 | 0.8 | 772 | - |

Figure 22

METHOD FOR GENERATING CYAN FLUORESCENT PROTEINS WITH REDUCED PH SENSITIVITY

INTRODUCTION

The present invention proposes a method for generating cyan fluorescent proteins with reduced pH sensitivity.

Fluorescent proteins (also called fluorescent probes), such as the green fluorescent protein extracted from the *Aequoria Victoria* jellyfish (Green Fluorescent Protein or GFPav) and its variants, constitute an essential tool for exploring living cells, notably in fluorescence imaging techniques, flow cytometry and high throughput biological tests. Fused with various proteins, these fluorescent probes make it possible to determine the localisation and traffic movement of these proteins and to analyse various biological process such as protein-protein interactions, enzyme activities or second messenger signalling. The success of these proteins relies notably on the fact that they can be expressed in a numerous of living organisms and cell compartments (e.g. nucleus, mitochondria, Golgi body). The numerous approaches to directed and random mutagenesis conducted over the past 15 years have thus given rise to a large diversity of variants of the native GFPav (Day et al., 2009). These differ from GFPav through the mutation of a few amino acids and fluoresce in a different colour range from blue to red.

Among the most frequently used GFPav variants is the Enhanced Cyan Fluorescent Protein (ECFPav or ECFP). This protein has 239 amino acids of which 6 to 9 are mutated by comparison to the native GFPav (K26R, S65T, Y66W, F64L, N146I, M153T, V163A, N164H, H231L) (Cubitt et al., 1995; Llopis et al., 1998; Cubitt et al., 1999). Substitution of the Tyr66 amino acid by Tryptophan led to a shift in the excitation and emission spectra towards blue by comparison to GFPav, respectively at 436 and 475 nm, while the other mutations made it possible to enhance some physico-chemical properties such as protein folding, solubility, photostability and brightness. The brightness of this ECFP nevertheless remains less than that of the enhanced GFP (40%).

ECFP is to this day one of the most commonly used fluorescent proteins as a donor in imaging studies by Förster type resonance energy transfer (FRET), more particularly in tandem with EYFP (Miyawaki et al., 1999) and its variants, as a result of partial overlapping of their absorption and emission spectra. The coupling of ECFP to this type of protein has thus made it possible to develop numerous FRET biosensors, notably for the study of cell metabolism.

However, similarly to all real-time imaging methods, FRET requires an extremely precise quantitative analysis of fluorescence signals, which is rarely the case with conventional microscopy techniques. The complex and not very efficient emission properties of ECFP therefore do not enable a reliable interpretation of the results obtained by quantitative imaging in living cells. In fact, ECFP displays several excitation states revealing the existence of several distinct conformations that can be adopted by this protein, as well as low quantum yield and a shortened fluorescence lifetime by comparison to GFPav (Shaner et al., 2007; Patterson et al., 2001; Tramier et al. 2002).

As for most of fluorescent probes, ECFP is characterized by very high sensitivity to environmental factors, particularly to pH (Miyawaki et al., 2000). Its mean fluorescence lifetime (Tau or $\tau$) slightly decreases between pH 11 and pH 7 but is considerably reduced from 2.5 ns to 1.5 ns when the pH drops to pH 5.5. It is also well established that its fluorescence intensity ($I_f$) drops rapidly by ~10% at pH 6.5 and by ~40% at pH 5.5. This pH sensitivity constitutes a major drawback in the use of ECFP in quantitative imaging in intact cells because intracellular pH varies depending on of the cell compartments and experimental conditions tested, such as mitogenic stimulation or metabolic stress. Thus, when ECFP is solubilised in two cell compartments with different pH (for example, neutral pH in the cytosol and acid pH in the lysosomes), it displays distinct emission properties independently from the biological process studied, potentially leading to artefact interpretations. To date, the only way of reducing these artefacts is to regularly check the ambient pH or to fix it (<<clamping>>). It would thus be highly desirable to have an ECFP with reduced pH sensitivity and whose half-transition pH ($pH_{1/2}$) is well below that of the physiological pH.

The efforts undertaken to date to improve the photophysical and physico-chemical performances of ECFP have mainly focused on enhancing its brightness (or fluorescence intensity), its maturation and solubilisation, as well as simplifying its emission properties, particularly its decay in fluorescence emission (Rizzo et al. (2004); Nguyen et al. (2005); Goedhart et al. (2010); Sawano et al. (2000)). Nevertheless, no study has specifically focused on developing cyan fluorescent proteins displaying reduced pH sensitivity, and in which the fluorescence spectrum characteristic of ECFP has been preserved.

There is thus a need to develop a method for generating cyan fluorescent proteins with reduced pH sensitivity, while preserving the spectral properties specific of these proteins.

DETAILED DESCRIPTION

The present invention proposes a method for generating cyan fluorescent proteins with reduced pH sensitivity, particularly acidic pH. Besides cyan fluorescent proteins obtainable by said method, other aspects of the invention relate to nucleic acids coding for said proteins, recombinant vectors comprising said nucleic acid, host cells expressing said proteins, biosensors comprising said proteins, as well as the use of said proteins, said nucleic acids, said host cells and said biosensors.

The present inventors have indeed discovered that the pH sensitivity of the cyan fluorescent protein ECFP is strongly governed by the nature of specific amino acids, and more particularly of amino acids at positions 65 and 148 of the ECFP protein sequence. The method of the invention therefore comprises a step in which a mutation is introduced into the cyan fluorescent protein ECFP of sequence SEQ ID NO:2, preferably at position 65 and/or 148 of this sequence. In addition, although the introduction of a single mutation can dramatically affect the physico-chemical properties, notably spectral, of fluorescent proteins (Espagne et al., 2011; Sawano et al., 2000), the introduction of some mutations identified by the inventors at position 65 and/or 148 of SEQ ID NO:2, does not produce a negative effect on said properties and can moreover increase the average fluorescence lifetime (Tau or $\tau$) at neutral pH of these proteins, and lower $pH_{1/2}$.

The <<cyan fluorescent proteins>> according to the invention designate all mutated fluorescent proteins originating from *Aequora victoria* (ECFP) protein sequence SEQ ID NO:2, whose absorption spectrum displays an absorbance maximum comprised between 415 and 450 nm, and whose emission spectrum has a fluorescence maximum comprised between 470 and 490 nm. Preferably, the absorption spectrum of said proteins displays an absorbance maximum around 435 nm, and their emission spectrum displays a fluorescence maximum around 476 nm. The absorption spectrum corresponds to the wavelengths at which the fluorescent protein is excited, while the emission spectrum corresponds to wavelengths at which the protein emits fluorescence.

The mutated cyan fluorescent proteins according to the present invention therefore have the advantage of displaying an absorption and emission spectrum similar to the spectrum of ECFP of SEQ ID NO:2. Moreover, the fluorescence intensity of these proteins ($I_f$) and their average fluorescence lifetime (Tau or τ) remain stable and higher over a broader pH range.

The method of the invention thus enables to obtain cyan fluorescent proteins whose loss of fluorescence intensity ($I_f$) and average fluorescence lifetime (τ) at acidic pH are inferior to those of ECFP, in other words respectively inferior to 50% and 33%, preferably inferior to 30%, even more preferably inferior to 20%. Even more preferably, these losses are null.

The average lifetime at neutral pH of these mutated proteins is moreover enhanced by comparison to ECFP. This lifetime is therefore superior to 2.5 nanoseconds (ns), and can reach 4.12 ns.

The $pH_{1/2}$ of the proteins of the invention is also reduced to a $pH_{1/2}$ value inferior to that of the ECFP, since it is less than 5.6, and can reach a $pH_{1/2}$ value of 3.4 and even 3.1.

Another particular advantage of the invention resides in the fact that these single mutations can be introduced directly into existing biosensors, which are more particularly used in FRET applications. The cyan fluorescent proteins according to the invention can notably be coupled, within biosensors, to orange fluorescent proteins (TagRFP) or yellow fluorescent proteins (type YFP), whose pH sensitivity has been reduced. The development of such biosensors therefore allows the study of a variety of biological processes under any pH condition, and in particular at acidic pH, which was impossible up to now due to the pH sensitivity of the ECFP protein. In this regard, the inventors have developed a biosensor with reduced pH sensitivity in which the cyan fluorescent protein of the invention has been coupled to the orange fluorescent protein TagRFP.

The present invention thus meets the requirements of current real-time quantitative imaging methods, and allows the use of cyan fluorescent proteins under acidic pH conditions.

A first aspect of the present invention is a method for generating cyan fluorescent proteins displaying reduced pH sensitivity comprising a step a) according to which a single mutation is introduced into a protein sequence comprising the sequence SEQ ID NO:2, as described below:

positions such as methionine in N-terminal, a signal peptide sequence or even an amino acid sequence allowing protein purification. The latter can be chosen by the skilled person in the art Among the peptide sequences which do not affect the functional properties of proteins, such as a polyhistidine sequence and/or a protease cleavage site sequence (e.g. SEQ ID NO:70 of sequence MSYYHHHHHHDYDIPTTENLY-FQGA). Thus the protein sequence to be mutated can comprise or consist of the sequence SEQ ID NO:4.

According to another preferred embodiment, said sequence SEQ ID NO:2 does not comprise other amino acids, and said protein sequence then consists only of the sequence SEQ ID NO:2.

Preferably, said mutation is introduced at position 65 or 148 of sequence SEQ ID NO:2.

According to a particular embodiment of the invention, the method comprises another step b) according to which an additional mutation is introduced at position 65 of sequence SEQ ID NO:2 if the mutation in step a) is introduced at position 148. Reciprocally, step b) of said method consists in introducing additional mutation at position 148 of sequence SEQ ID NO:2 if the mutation in step a) is introduced at position 65.

According to another particular embodiment of the invention, the method consists of step a) and step b), as defined above.

According to an advantageous embodiment, the method consists solely of step a) as defined above.

Preferably, according to the different embodiments of the method as described above, the amino acid at position 65 is substituted by serine and/or the amino acid at position 148 is substituted by glycine, alanine, serine or glutamic acid. Even more preferably, said amino acid at position 148 is substituted by glycine, alanine or serine. According to another preferred embodiment, the amino acid in position 65 is substituted by serine and the amino acid in position 148 is substituted by glycine, aspartic acid, glutamic acid or serine, preferably by glycine, aspartic acid or serine. Even more preferably, the amino acid at position 65 is substituted by serine and the amino acid at position 148 is substituted by glycine.

It is understood that the method of the invention, whether or not it comprises or consists of step a) or step a) and b), allows the generation of cyan fluorescent proteins as defined above and displaying reduced pH sensitivity.

In the case where the amino acid is at position 65 is substituted by serine, the cyan fluorescent proteins obtained according to the method of the invention also display an increased quantum yield, a simplified fluorescence kinetic, a

```
                                                            (SEQ ID NO: 2)
VSKGEELFTGVVPILVELDGDVNGHKFSVSGEGEGDATYGKLTLKFICTTGKLP

VPWPTLVTTLTWGVQCFSRYPDHMKQHDFFKSAMPEGYVQERTIFFKDDGNYKTRAEVKF

EGDTLVNRIELKGIDFKEDGNILGHKLEYNYISHNVYITADKQKNGIKANFKIRHNIEDG

SVQLADHYQQNTPIGDGPVLLPDNHYLSTQSALSKDPNEKRDHMVLLEFVTAAGITLGMDELYK.
                                                                 60
```

By <<comprising>> or <<containing>>, it is meant herein that the listed elements are required or mandatory but that other optional elements may or may not be present.

Thus, by <<protein sequence comprising sequence SEQ ID NO:2>>, it is meant herein that the sequence SEQ ID NO:2 can comprise other amino acids at its N- or C-terminal reduced reversible photobleaching as well as a slowed irreversible photobleaching. As a result of their advantageous photophysical properties, the cyan fluorescent proteins of the invention comprising at least the 65S mutation are particularly useful in imaging applications of living cells, such as FRET or FLIM type applications.

According to the method of the invention, by <<mutation>>, it is meant an alteration in the amino acid sequence SEQ ID NO:2 of the ECFP protein, following modification of the nucleotide sequence SEQ ID NO:1 coding for said protein. The mutation according to the invention can be an addition, a deletion or a substitution of an amino acid by another amino acid relative to the original protein sequence. Preferably, said mutation is a substitution.

The methods allowing introduction of a mutation in a nucleotide sequence are known to the skilled person in the art. For example, it is possible to introduce a mutation by random or directed mutagenesis, by PCR by using degenerate primers, by radiation or by using a mutagenic agent. Said techniques are notably described by Sambrook et al. in "Molecular Cloning: A laboratory Manual", $3^{rd}$ edition, Cold Spring Harbor Laboratory Press, (2001), and by Ausubel et al. in "Current Protocols in Molecular Biology", John Wiley & Sons (2011). Preferably, the mutation according to the invention is introduced by directed mutagenesis. It is understood that in order to introduce said mutations, the skilled person in the art can use functionally equivalent codons (or nucleotide triplets), that is to say codons which code for the same amino acids, or biologically equivalent amino acids. Moreover, should the skilled person in the art wish to optimise the expression of the mutated cyan fluorescent protein of the invention, s/he can refer to the database on the website http://www.kazusa.or.jp/codon/ which lists the optimal use of codons in various organisms and organelles.

By <<amino acid>>, it is meant, in the context of this invention, that all the residues of the natural a-amino acid (for example alanine (Ala, A), arginine (Arg, R), asparagine (Asn, N), aspartic acid (Asp, D), cysteine (Cys), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y) and valine (Val, V) in the D or L form), as well as non natural amino acids.

Another aspect of the invention relates to the cyan fluorescent proteins with reduced pH sensitivity that are obtainable according to the method described above, said method comprising or consisting of step a), or step a) and b).

By <<pH sensitivity>> or pH dependence according to the invention, it is meant herein the loss of fluorescence intensity ($I_f$) and/or decrease in fluorescence lifetime (Tau or τ) of a cyan fluorescent protein when the pH of the medium in which the protein is goes from a basic pH to an acidic pH. pH sensitivity according to the invention can be defined by at least one of the two above-mentioned criteria.

Preferably, the term <<pH sensitivity>> refers to the loss of fluorescence intensity ($I_f$) and decrease in fluorescence lifetime (Tau or τ) of a cyan fluorescent protein when the pH of the medium in which the protein is goes from a basic pH to an acidic pH. According to the invention, the terms loss, lowering, decrease, decay or reduction are synonyms and can be used interchangeably.

The terms fluorescence intensity($I_f$), quantum yield or brightness are interdependent. In the context of the invention, the term <<fluorescence intensity>> means the number of photons emitted by a fluorescent protein per unit of volume and per unit of time at a given wavelength. The term <<quantum yield>> designates the ratio of the intensity of the emitted fluorescence over the whole of the emission spectrum and of the absorbed intensity of said protein. As for the term <<brightness>>, this refers to the product of quantum yield and the molar absorption coefficient of said protein.

The <<fluorescence intensity>> of a fluorescent protein can be obtained with the aid of a spectrofluorimeter, such as for example Fluorolog®3 (HORIBA Jobin Yvon), and under low concentration conditions such as $\epsilon(\lambda_{ex}) \cdot C \cdot 1 < 0.05$, expressed as:

$$I_{em}(\lambda_{ex}, \lambda_{em}) = k \cdot I_0(\lambda_{ex}) \cdot f(\lambda_{em}) \cdot \epsilon(\lambda_{ex}) \cdot C \cdot 1$$

wherein $\epsilon(\lambda_{ex})$ and $I_0(\lambda_{ex})$ respectively designate the molar absorption coefficient of said protein and the intensity of the incident beam at the excitation wavelength $\lambda_{ex}$;

$f(\lambda_{em})$ represents the fluorescence intensity at the emission wavelength $\lambda_{em}$.

Incorporated into the emission spectrum, this parameter is equal to the quantum yield;

C is the concentration of said protein;

and 1 is the length of the optical path in the sample.

A method allowing the measurement of these parameters is described by B. Valeur in <<Molecular Fluorescence: Principles and Applications>>, $3^{rd}$ edition. (2006), Wiley-VCH. In addition, measurement of the fluorescence intensity makes it possible to take into account variations:

in the molar absorption coefficient, and therefore in the absorption spectrum;

in the probability of emission at the emission wavelength, and therefore by extension of the emission spectrum, when the protein is studied under different pH conditions.

The term <<fluorescence lifetime>> (Tau, <τ>) means the average time during which a fluorescent protein remains in an excited state before returning to its basal state. This duration is preferably measured in nanoseconds. Here, the fluorescence lifetime is a mean lifetime (<τ>) and is obtained by adjusting fluorescence emission decays I(t) using an exponential sum according to the equation:

$$\langle \tau \rangle = \frac{\sum_i a_i \cdot \tau_i}{\sum_i a_i}$$

with $$I(t) = \sum_i a_i \cdot e^{-t/\tau_i}$$

Here, fluorescence emission decays are obtained by means of a unique photon counting technique described by O'Connor et al. (1984).

Among the methods for measuring fluorescence lifetime, we can cite Fluorescence Lifetime Imaging Microscopy (FLIM) and Time-Correlated Single Photon Counting (TCSPC).

The methods as described above can preferably be implemented in a temperature range comprised between 0° C. and 100° C., preferably in a range comprised between 1° C. and 90° C., 2° C. and 80° C., 3° C. and 70° C., 4° C. and 60° C., 5° C. and 50° C., even more preferably between 6° C. and 40° C., 7° C. and 30° C., 8° C. and 25° C., 9° C. and 24° C., 10° C. and 23° C., and even more preferably between 11° C. and 22° C., 12° C. and 21° C. Advantageously, said temperature range is 20° C.+/−0.1° C.

By basic pH, it is meant a pH value comprised between 7 and 14, and by acidic pH, it is meant a pH value comprised between 0 and 7. Said pH sensitivity according to the invention is therefore studied over a pH range going from 0 to 14, preferably a pH range from pH 1 to pH 13, from pH 2 to pH 12, more preferably over a range from pH 2.5 to pH 11, from pH 3 to 10, pH 4 to pH 9, and even more preferably over a range from pH 5 to pH 8, and from pH 5.5 to pH 7.5. Advantageously, the tested pH goes from pH 5.5 to pH 7.4. The losses, decreases, or changes mentioned above are always measured, according to the invention, between the most basic pH and the most acidic pH.

By <<reduced pH sensitivity>>, it is meant that the loss of fluorescence intensity ($I_t$) of a protein obtainable according to the method of the invention is inferior to 50%, preferably inferior to 33%, even more preferably inferior to 30%, 25%, 20%, 15%, 10%, 5% and advantageously equal to 0%, when the pH of the medium in which said protein is goes from a basic pH to an acidic pH. More particularly, said loss of fluorescence intensity is inferior to 50%, preferably inferior to 33%, even more preferably inferior to 30%, 25%, 20%, 15%, 10%, 5% and advantageously equal to 0%, when said pH goes from pH 7.4 to pH 5.5.

The term <<reduced pH sensitivity>> can also mean that the loss of the fluorescence lifetime (Tau or τ) of a protein obtainable according to the method of the invention is inferior to 33%, preferably inferior to 32%, even more preferably inferior to 30%, 25%, 20%, 15%, 10%, 5% and advantageously equal to 0%, when the pH of the medium in which said protein goes from a basic pH to an acidic pH. More particularly, said loss of fluorescence lifetime is inferior to 33%, preferably inferior to 32%, even more preferably inferior to 30%, 25%, 20%, 15%, 10%, 5% and advantageously equal to 0%, when said pH goes from pH 7.4 to pH 5.5.

The pH sensitivity of a cyan fluorescent protein is reduced according to the invention when at least one of the two above-defined criteria is fulfilled.

Preferably, the pH sensitivity of a cyan fluorescent protein is reduced if the two above-defined criteria are fulfilled.

In addition to these criteria, the cyan fluorescent proteins with <<reduced pH sensitivity>> can sometimes display a decrease in their half-transition pH ($pH_{1/2}$) with respect to the $pH_{1/2}$ value of the ECFP. Thus the decrease in $pH_{1/2}$ is of at least 0.1, 0.2, 0.3, 0.4 pH unit, preferably of at least 0.5, 1, 1.5, 2 pH units and yet more preferably of at least 2.2 pH units.

By <<$pH_{1/2}$>> according to the invention, it is meant herein the pH value for which the sum of fluorescence intensities at 474 nm of the protein at the most basic pH and at the most acidic pH as defined above is reduced by half. The fluorescence intensity is measured by the method defined above. Preferably, the $pH_{1/2}$ is the pH value for which the sum of fluorescence intensities at 474 nm of said protein at pH 7.4 and at pH 2.5 is reduced by half. An equivalent method for measuring the half-transition pH of a fluorescent protein consists in measuring, at each tested pH value, the intensity of total fluorescence emitted by said protein by calculating the area under the fluorescence emission spectrum obtained by excitation at 420 nm. This total intensity is then corrected from the absorbance at 420 nm. The half-transition period can also be estimated from the variation as a function of pH of the corrected total intensity thus obtained according to a similar calculation method (pH value such as the sum of these total intensities are the most basic and at the most acidic is reduced by half).

Furthermore, these proteins can also show a prospective increase in their fluorescence lifetime (Tau or τ) at pH 7.4 compared to the ECFP lifetime. Thus the increase in τ value is at least of 0.1 ns, preferably of at least 0.5 ns, 1 ns and even more preferably of at least 1.5 ns.

Nevertheless, the <<reduced pH sensitivity>> property should not be liken to that of thermodynamic or kinetic stability, more commonly known as <<stability>>. The <<stability>> of a protein is indeed characterized by the retention of the native structure of this protein within a given range of external physicochemical conditions (temperature, pressure, etc), and is a complex concept that can be difficult to assess as it depends not only on external conditions used to disrupt the protein structure but also on the parameters selected to evaluate the denatured state of this protein.

The norm according to the invention for describing cyan fluorescent proteins follows the following rule: ECFP (mutated amino acid number—name of the introduced amino acid).

The numbering of amino acids according to the invention is not a conventional one based on the N-terminal methionine amino acid, but on the basis of the valine amino acid of the ECFP SEQ ID NO:2 sequence. Thus, the SEQ ID NO:2 sequence acts as a reference to allocate the number or position of the mutated amino acid, and the name of the amino acid introduced can be determined by carrying out an optimal alignment, as further described, of the SEQ ID NO:2 sequence with that of the cyan fluorescent protein obtained according to the method of the invention.

Examples of cyan fluorescent proteins with reduced pH sensitivity according to the invention comprise, without being limitation, or consist of a protein sequence selected from among the group consisting of the sequences SEQ ID NO:6, SEQ ID NO:8, SEQ ID NO:58, SEQ ID NO:10, SEQ ID NO:12, SEQ ID NO:14, SEQ ID NO:60, SEQ ID NO:72, SEQ ID NO:74 and SEQ ID NO:76 (see Table 1 below).

According to a preferred embodiment of the invention, the cyan fluorescent proteins according to the invention comprise, without limitation, or consist of a protein sequence selected from the group consisting of the sequences SEQ ID NO:12, SEQ ID NO:14, SEQ ID NO:60, SEQ ID NO:74 and SEQ ID NO:76.

According to another advantageous embodiment, the cyan fluorescent protein according to the invention comprises or consists of a protein sequence of sequence SEQ ID NO:12.

The invention also relates to the nucleic acids coding for the cyan fluorescent proteins as defined above.

By <<nucleic acid>>, or nucleotide sequence, it is meant a precise chain of nucleotides, modified or not, enabling to define a fragment or a region of a nucleic acid, including or not non-natural nucleotides, and that may correspond both to a single strand or double strand DNA chosen from a cDNA, a genomic DNA and a plasmid DNA, and the transcription products of said DNA.

Examples of nucleic acids according to the invention comprise, without limitation, or consist of a nucleotide sequence selected from the group consisting of the sequences SEQ ID NO:5, SEQ ID NO:7, SEQ ID NO:57, SEQ ID NO:9, SEQ ID NO:11, SEQ ID NO:13, SEQ ID NO:59, SEQ ID NO:71, SEQ ID NO:73 and SEQ ID NO:75 (see Table 1 below).

According to a preferred embodiment of the invention, the nucleic acids comprise, without limitation, or consist of a nucleotide sequence selected from the group consisting of the sequences SEQ ID NO:11, SEQ ID NO:13 SEQ ID NO:59, SEQ ID NO:73 and SEQ ID NO:75.

According to another advantageous embodiment, the nucleic acid according to the invention comprises or consists of a nucleotide sequence of sequence SEQ ID NO:11.

The nucleic acids as defined above can comprise or not a start codon at the 5' end and/or a stop codon at the 3' end of their sequence. The start codons include, without limitation, the codons (or trinucleotides, or nucleotide triplets) ATG, AUG, TTG, UUG, GTG, GUG, CTG and CUG and can be selected by the skilled person in the art based on the host cell in which said nucleic acid to be translated. The stop codons include in particular codons TAG, UAG, TAA, UAA, TGA and UGA and can be selected by the skilled person in the art based on the host cell in which said nucleic acid is to be translated.

Advantageously, these nucleic acids do not comprise a start codon and/or a stop codon when the cyan fluorescent protein for which they code is fused, directly or indirectly, with another protein.

These nucleic acids can also comprise at their 5' end and/or 3' end a nucleotide sequence coding for a signal peptide and/or a nucleotide sequence coding for an amino acid sequence allowing purification of the protein for which they code. The latter can be chosen by the skilled person in the art among nucleotides which do not affect the functional properties of proteins, such as a polyhistidine sequence and/or a protease cleavage site sequence (e.g. SEQ ID NO:69 of sequence ATGTCGTACT ACCATCACCA TCACCATCAC GATTACGATA TCCCAACGAC CGAAAACCTG TATTTTCAGG GCGCC).

According to another embodiment of the invention, the method comprises in addition to step a), or to step a) and step b), a step c) according to which at least one other mutation selected from the group 9G, 11I, 19E, 26R, 68L, 72A, 87V, 145A, 164H, 167A, 172T, 175G, 194I and 206K is introduced into the SEQ ID NO:2 sequence, said step c) being carried out either before or after step a) and/or step b).

The <<cyan fluorescent proteins>> according to the invention can therefore have one or several supplementary (or additional) mutations at positions other than position 65 and 148, providing that that these mutations allow the preservation of the absorption and emission spectra of the proteins of the invention as previously described. Such conservative mutations are known to the skilled person in the art and can be selected in a non-limitative manner, among mutations 9G, 11I, 19E, 26R, 68L, 72A, 87V, 145A, 164H, 167A, 172T, 175G, 194I, and 206K, and preferably among mutations 26R, 72A, 145A, 164H and 206K. These supplementary mutations can moreover be introduced before or after the mutations at position 65 and/or 148 characteristic of the invention, according to an identical method. Thus, the method of the invention comprising or consisting of step a), b) and c) allows the production of cyan fluorescent proteins as defined above and displaying a reduced pH sensitivity.

The amino acid sequences of the cyan fluorescent proteins mutated in this way can therefore display at least about 60%, 65%, 70%, 75%, 80%, 85%, 90%, 91%, 92%, 93%, 94% 95%, 96%, 97%, 98%, 99% identity with SEQ ID NO:2 sequence of ECFP, contiguously or non-contiguously. Preferably the amino acid sequences according to the invention display at least about 85%, advantageously at least about 90% identity with SEQ ID NO:2 sequence, contiguously or non-contiguously. Even more preferably, the amino acid sequences according to the invention display at least about 95% identity, advantageously at least about 97% and even more preferably at least about 99% identity with SEQ ID NO:2 sequence, contiguously or non-contiguously.

The percentage of identity described above can be determined by carrying out an optimal alignment of the amino acid sequences to be compared (here with SEQ ID NO:2 sequence), this percentage being purely statistical and the differences between the two sequences being distributed over their whole length. This alignment can be carried out using an algorithm known to the skilled person in the art, such as the global alignment of Needleman and Wunsch (J. Mol. Biol., 1970, 48:443) and computerised applications, or just by a mere inspection. The best alignment (that is to say the one producing the highest percentage of identity) is then selected. The percentage of identity between two amino acid sequences is determined by comparing these two sequences aligned in an optimal manner in which the amino acid sequences to be compared can comprise additions or deletions by comparison to the reference sequence (here SEQ ID NO:2 sequence) for an optimal alignment of these two sequences. The percentage of identity is calculated by determining the number of identical positions for which the amino acid residue is identical between the two sequences, dividing this number of identical positions by the total number of positions and multiplying the result obtained by 100 to obtain the percentage of identity between these two sequences.

Preferably, 1 to 20 supplementary mutations can be introduced into the SEQ ID NO:2 sequence, preferably 1 to 10 mutations, even more preferably 1 to 5 mutations and advantageously 1 to 2 mutations.

According to a preferred embodiment of the invention, the additional mutations introduced into the SEQ ID NO:2 sequence are selected solely among mutations 9G, 11I, 19E, 26R, 68L, 72A, 87V, 145A, 164H, 167A, 172T, 175G, 194I and 206K. Even more preferably, these additional mutations are selected solely among mutations 26R, 72A, 145A, 164H and 206K.

Examples of proteins that can be produced in this way, comprising, without limitation, or consisting of a protein sequence selected from the group consisting of the sequences SEQ ID NO:16, SEQ ID NO:18, SEQ ID NO:20, SEQ ID NO:62, SEQ ID NO:22, SEQ ID NO:24, SEQ ID NO:26, SEQ ID NO:64, SEQ ID NO:28, SEQ ID NO:30, SEQ ID NO:32, SEQ ID NO:66, SEQ ID NO:34, SEQ ID NO:80 and SEQ ID NO:82 (see Table 1 below).

According to a preferred embodiment, the cyan fluorescent proteins of the invention comprise, without limitation, or consist of a protein sequence selected from the group consisting of the sequences SEQ ID NO:18, SEQ ID NO:20, SEQ ID NO:62, SEQ ID NO:22, SEQ ID NO:24, SEQ ID NO:26, SEQ ID NO:64, SEQ ID NO:28, SEQ ID NO:30, SEQ ID NO:32, SEQ ID NO:66, SEQ ID NO:34, SEQ ID NO:80 and SEQ ID NO:82.

According to an even more preferred embodiment, the cyan fluorescent proteins according to the invention comprise, without limitation, or consist of a protein sequence selected from the group consisting of the sequences SEQ ID NO:18, SEQ ID NO:20, SEQ ID NO:62, SEQ ID NO:22, SEQ ID NO:24, SEQ ID NO:26, SEQ ID NO:64, SEQ ID NO:28, SEQ ID NO:30, SEQ ID NO:32, SEQ ID NO:66, SEQ ID NO:80 and SEQ ID NO:82.

Even more preferably, the cyan fluorescent proteins of the invention comprise, without limitation, or consist of a protein sequence selected from the group consisting of the sequences SEQ ID NO:22, SEQ ID NO:24, SEQ ID NO:26, SEQ ID NO:64, SEQ ID NO:28, SEQ ID NO:30, SEQ ID NO:32, SEQ ID NO:66, SEQ ID NO:80 and SEQ ID NO:82.

According to an even more advantageous embodiment, the cyan fluorescent proteins of the invention comprise, without limitation, or consist of a protein sequence selected from the group consisting of the sequences SEQ ID NO:22, SEQ ID NO:24, SEQ ID NO:26 and SEQ ID NO:64.

According to another advantageous embodiment of the invention, the cyan fluorescent proteins of the invention comprise, without limitation, or consist of a protein sequence selected from the group consisting of the sequences SEQ ID NO:28, SEQ ID NO:30, SEQ ID NO:32 and SEQ ID NO:66.

According to another advantageous embodiment, the cyan fluorescent protein of the invention comprises or consists of the protein sequence SEQ ID NO:80 or SEQ ID NO:82.

The invention also relates to the nucleic acids coding for the cyan fluorescent proteins as described above.

The nucleic acids coding for said proteins, or nucleotide sequences, can therefore display at least about 60%, 65%, 70%, 75%, 80%, 85%, 90%, 91%, 92%, 93%, 94% 95%, 96%, 97%, 98%, 99% identity with the ECFP sequence SEQ ID NO:1, contiguously or non-contiguously. Preferably, the nucleotide sequences according to the invention display at least about 85%, advantageously at least about 90% identity with the SEQ ID NO:1 sequence, contiguously or non-contiguously. Even more preferably, the nucleotide sequences according to the invention display at least about 95% identity, advantageously at least about 97% and even more preferably at least about 99% identity with the SEQ ID NO:1 sequence, contiguously or non-contiguously.

The percentage of identity described above can be determined by carrying out an optimal alignment of the nucleotide sequences to be compared (here with the SEQ ID NO:1 sequence), this percentage being purely statistical and the differences between the two sequences being distributed over their whole length. This alignment can be carried out using an algorithm known to the skilled person in the art, such as the global alignment of Needleman and Wunsch (J. Mol. Biol., 1970, 48:443) and computerised applications, or just by a mere inspection. The best alignment (in other words the one producing the highest percentage of identity) is then selected. The percentage of identity between two nucleotide sequences is determined by comparing these two sequences aligned in an optimal manner in which the nucleotide sequence to be compared can comprise additions or deletions by comparison to the reference sequence (in this case sequence SEQ ID NO:1) for an an optimal alignment of these two sequences. The percentage of identity is calculated by determining the number of identical positions for which the nucleic acid is identical between the two sequences, dividing this number of identical positions by the total number of positions and multiplying the result obtained by 100 to obtain the percentage of identity between these two sequences.

Examples of nucleic acids coding for the proteins of the invention displaying additional mutations comprise, without limitation, or consist of a nucleotide sequence selected from the group consisting of the sequences SEQ ID NO:15, SEQ ID NO:17, SEQ ID NO:19, SEQ ID NO:61, SEQ ID NO:21, SEQ ID NO:23, SEQ ID NO:25, SEQ ID NO:63, SEQ ID NO:27, SEQ ID NO:29, SEQ ID NO:31, SEQ ID NO:65, SEQ ID NO:33, SEQ ID NO:79 and SEQ ID NO:81 (see Table 1 below).

According to a preferred embodiment, the nucleic acids coding for cyan fluorescent proteins according to the invention comprise, without limitation, or consist of a nucleotide sequence selected from the group consisting of the sequences SEQ ID NO:17, SEQ ID NO:19, SEQ ID NO:61, SEQ ID NO:21, SEQ ID NO:23, SEQ ID NO:25, SEQ ID NO:63, SEQ ID NO:27, SEQ ID NO:29, SEQ ID NO:31, SEQ ID NO:65, SEQ ID NO:33, SEQ ID NO:79 and SEQ ID NO:81.

According to a more preferred embodiment, the nucleic acids according to the invention comprise, without limitation, or consist of a nucleotide sequence selected from the group consisting of the sequences SEQ ID NO:17, SEQ ID NO:19, SEQ ID NO:61, SEQ ID NO:21, SEQ ID NO:23, SEQ ID NO:25, SEQ ID NO:63, SEQ ID NO:27, SEQ ID NO:29, SEQ ID NO:31, SEQ ID NO:65, SEQ ID NO:79 and SEQ ID NO:81.

Even more preferably, the nucleic acids according to the invention comprise, without limitation, or consist of a nucleotide sequence selected from the group consisting of the sequences SEQ ID NO:21, SEQ ID NO:23, SEQ ID NO:25, SEQ ID NO:63, SEQ ID NO:27, SEQ ID NO:29, SEQ ID NO:31, SEQ ID NO:65, SEQ ID NO:79 and SEQ ID NO:81.

According to an even more advantageous embodiment, the nucleic acids of the invention comprise, without limitation, or consist of a nucleotide sequence selected from the group consisting of the sequences SEQ ID NO:21, SEQ ID NO:23, SEQ ID NO:25, and SEQ ID NO:63.

According to another advantageous embodiment of the invention, the nucleic acids of the invention comprise, without limitation, or consist of a nucleotide sequence selected from the group consisting of the sequences SEQ ID NO:27, SEQ ID NO:29, SEQ ID NO:31, and SEQ ID NO:65.

According to another advantageous embodiment, the nucleic acid according to the invention comprises or consists of the nucleotide sequence SEQ ID NO:79 or SEQ ID NO:81.

TABLE 1 list of mutations that can be introduced in the SEQ ID NO: 2 sequence, with the corresponding amino acid sequences and nucleotide sequences.

| Mutation(s) introduced into the SEQ ID NO: 2 sequence | Protein sequence reference | Reference for the nucleic acid sequence coding for said protein sequence |
| --- | --- | --- |
| 148G | SEQ ID NO: 6 | SEQ ID NO: 5 |
| 148S | SEQ ID NO: 8 | SEQ ID NO: 7 |
| 148A | SEQ ID NO: 58 | SEQ ID NO: 57 |
| 148E | SEQ ID NO: 72 | SEQ ID NO: 71 |
| 65S | SEQ ID NO: 10 | SEQ ID NO: 9 |
| 65S, 148G | SEQ ID NO: 12 | SEQ ID NO: 11 |
| 65S, 148S | SEQ ID NO: 14 | SEQ ID NO: 13 |
| 65S, 148A | SEQ ID NO: 60 | SEQ ID NO: 59 |
| 65S, 148D | SEQ ID NO: 74 | SEQ ID NO: 73 |
| 65S, 148E | SEQ ID NO: 76 | SEQ ID NO: 75 |
| 72A, 145A, 148D | SEQ ID NO: 16 | SEQ ID NO: 15 |
| 72A, 145A, 148G | SEQ ID NO: 18 | SEQ ID NO: 17 |
| 72A, 145A, 148S | SEQ ID NO: 20 | SEQ ID NO: 19 |
| 72A, 145A, 148A | SEQ ID NO: 62 | SEQ ID NO: 61 |
| 65S, 72A, 145A, 148D | SEQ ID NO: 22 | SEQ ID NO: 21 |
| 65S, 72A, 145A, 148G | SEQ ID NO: 24 | SEQ ID NO: 23 |
| 65S, 72A, 145A, 148S | SEQ ID NO: 26 | SEQ ID NO: 25 |
| 65S, 72A, 145A, 148A | SEQ ID NO: 64 | SEQ ID NO: 63 |
| 65S, 72A, 148D, 206K | SEQ ID NO: 28 | SEQ ID NO: 27 |
| 65S, 72A, 148G, 206K | SEQ ID NO: 30 | SEQ ID NO: 29 |
| 65S, 72A, 148S, 206K | SEQ ID NO: 32 | SEQ ID NO: 31 |
| 65S, 72A, 148A, 206K | SEQ ID NO: 66 | SEQ ID NO: 65 |
| 65S, 72A, 206K | SEQ ID NO: 34 | SEQ ID NO: 33 |
| 26R, 65S, 148G, 164H, 206K | SEQ ID NO: 80 | SEQ ID NO: 79 |

Another aspect of the invention relates to recombinant vectors comprising the nucleic acid coding for the mutated cyan fluorescent protein according to the invention, as defined above. Said nucleic acid can thus be inserted into a vector capable of replication with the objective of amplifying this nucleic acid, or to express the cyan fluorescent protein according to the invention. Among the vectors according to the invention are comprised cloning vectors which allow the amplification of a nucleic acid, and expression vectors which allow a protein to be expressed; these vectors are well known to the skilled person in the art. Such vectors include, without limitation, plasmids, cosmids, YACS, viral (adenovirus, retrovirus, episome EBV) and phagic vectors. The skilled person in the art can moreover use any other appropriate vector allowing expression of the cyan fluorescent protein of the invention.

Methods for inserting nucleic acids into such vectors are known to the skilled person in the art. In general, a nucleic acid is inserted into at least one appropriate endonuclease restriction site by using techniques known in the art (see, for example, the techniques described in Sambrook et al. (2001) and Ausubel et al. (2011).

Nucleotide sequences allowing the transcription of the nucleic acid of the invention, the expression and/or purification of the cyan fluorescent protein of the invention are moreover contained in the recombinant vector of the invention. These sequences include, generally and without limitation, one or several peptide signal sequence(s), a replication origin, one or several selection gene marker (s), an amplifying element, a promoter, a transcription stop sequence and possibly a sequence allowing purification of a protein. The insertion of such sequences into said vector can be carried out via standard ligation techniques known to the skilled person in the art.

Depending on the selected replication origin, said cloning or expression vector can replicate in one or more host cells. Thus, the replication origin of plasmid pBR322 is adapted to the majority of Gram negative bacteria, that of plasmid 2μ is specific to yeast, and various viral replication origins (SV40, polyome, adenovirus, VSV or BPV) are useful for cloning vectors in mammalian cells.

Depending on the selected promoter, the nucleic acid can be transcribed and the corresponding protein expressed in one or more host cells. Thus, the promoters T7, Lac, trp, tac, λPL are specific to bacteria of the $E.$ $coli$ genus; the promoters PHO5, GAP, TPI1, ADH are adapted to yeast; the promoters polyhedrin and P10 and their equivalent are used in insect cells; and finally the promoters CMV, MT1, from SV40, SRα, retroviral, and thermal shock protein gene promoters are adapted to mammalian cells.

Among the selection marker genes typically contained in cloning or expression vectors, can be cited without limitation: (a) genes conferring resistance to an antibiotic or toxin (for example, neomycin, zeocin, hygromycin, ampicillin, kanamycin, tetracyclin, chloramphenicol), and (b) genes allowing compensation for auxotrophic deficiencies (for example the gene coding for dihydrofolate reductase DHFR allowing resistance to methotrexate or even the TPI gene in $S.$ $pombe$).

Among the nucleotide sequences allowing protein purification, are included, without limitation, the Histidine sequence (Histidine Tag or Hisx6), the FLAG sequence and the GST sequence. A protease cleaving sequence such as TEV, can moreover be present in order to subsequently suppress the purification sequence.

According to a preferred embodiment of the invention, a nucleotide sequence of 6 histidines and a protease cleaving sequence TEV are present in the recombinant vector of the invention, and more particularly a nucleotide sequence coding for the amino acid sequence MSYYHHHHHHDYDIPTTENLYFQGA (SEQ ID NO:70).

According to a particularly preferred embodiment of the invention, the expression vector of the invention is vector pPROEX™ HTa (GibcoBRL).

Methods allowing the nucleic acid according to the invention to be connected to the additional sequences mentioned above are known to the skilled person in the art.

The present invention also relates to a host cell transformed by the nucleic acid coding for said protein, or by the recombinant vector comprising said nucleic acid.

As used herein, the term <<host cell>>, <<cell>> and <<cell line>> can be used interchangeably. All these terms also include their descendance, which include all subsequent generations. It is understood that all descendants are not necessarily identical given deliberate or accidental mutations.

By <<host cell>>, it is referred herein to a prokaryotic or eukaryotic cell, capable of replicating the nucleic acid coding for the mutated fluorescent protein according to the invention or the recombinant vector as previously described, and thus capable of expressing the mutated fluorescent protein of the invention. A host cell can be <<transfected>> or <<transformed>> according to a process known to the skilled person in the art by means of which said nucleic acid or said vector is transferred or introduced into the host cell. Examples of such methods include, without limitation, electroporation, lipofection, calcium phosphate transfection, transfection via DEAE-Dextran, microinjection, and biolistic.

Among host cells are included, without limitation, bacteria, yeasts, fungi, or any other higher eukaryotic cell. The skilled person in the art can therefore choose the appropriate host cells among the many available cell lines, notably via the American Type Culture Collection (ATCC) (www.ATCC.org). Examples of host cells include, without limitation, microorganisms such as Gram negative bacteria of the genus $Escherichia$ (for example, $E.$ $coli$ RR1, LE392, B, X 1776, W3110, DH5 alpha, JM109, KC8), $Serratia,$ $Pseudomonas,$ $Erwinia,$ $Methylobacterium,$ $Rhodobacter,$ $Salmonella$ or $Zymomonas$, Gram positive bacteria of the genus $Corynebacterium,$ $Brevibacterium,$ $Bacillus,$ $Arthrobacter,$ or $Streptomyces$, yeasts of the $Saccharomyces$ genus, cells from fungi of the genus $Aspergillus,$ $Neurospora,$ $Fusarium$ and $Trichoderma$, animal cells including HEK293, NIH3T3, Jurkat, MEF, Vero, HeLa, CHO, W138, BHK, COS-7, MDCK, C127, Saos, PC12, HKG, and insect cells Sf9, Sf21, Hi Five™ or $Bombyx$ $mori$. The use of insect cells is described in particular in the manual <<Baculovirus Expression vectors, A Laboratory Manual>>, by David R. O'Reilly et al., Oxford University Press, USA, (1992).

In the case where the host cell is transformed by the recombinant vector of the invention as described above, the choice of said host cell can be dictated by the choice of said vector, and depending on the chosen use, that is to say cloning of the nucleic acid or expression of the mutated cyan fluorescent protein of the invention.

Another aspect of the invention relates to a method for expressing and purifying the mutated cyan fluorescent protein of the invention. According to this method, the host cell as described above is cultured in an appropriate culture medium under conditions allowing expression of the protein of the invention. The skilled person in the art can use any conventional method allowing isolation and purification of said protein. For example in the case where said protein has been expressed in a soluble form in the host cells, the latter is recovered by centrifugation and suspended in a buffer, then a cellular extract is obtained by destroying the cells by means, for example, of an ultrasound homogeniser. From the supernatant obtained by centrifugation of this extract, a purified sample can be obtained by using a conventional method or a combination of conventional methods to isolate and purify the protein of the invention. These methods include, without limitation, extraction by solvent, ammonium sulphate release, desalting, precipitation by an organic solvent, gel filtration, preparative electrophoresis, isoelectric focalisation, ultrafiltration, numerous chromatography methods such as ion exchange chromatography (either anionic, using for example a resin such as diethylaminoethyl (DEAE) Sepharose, or cationic using for example a resin such as S-Sepharose (Pharmacia)), hydrophobic chromatography (using for example a resin such as Butyl Sepharose or Phenyl Sepharose), affinity chromatography by means of antibodies, adsorption chromatography, chromatofocalisation, high performance liquid chromatography (HPLC) and reverse phase HPLC.

Moreover, if a nucleotide sequence allowing purification of the protein, said sequence being fused with a cleavage sequence by a protease, is present in the recombinant vector, the produced protein can be recovered through treatment with a protease specific to said cleavage sequence (thrombin, trypsin, protease TEV, etc).

Another aspect of the invention relates to a biosensor comprising the cyan fluorescent protein according to the invention.

By <<biosensor>> is shall be understood herein a molecule comprising a biosensitive sensor, linked, by a covalent or non covalent bond, to another molecule, and allowing a biological response to be converted into an electrical, chemical, physical, photophysical or photochemical signal. A <<biosensitive sensor>> according to the invention is a natural or synthetic molecule, allowing the detection of the presence and/or the measurement of the concentration or activity of an analyte such as an ion, a sugar, an enzyme, a nucleic acid, an antibody, a cofactor or a natural or modified protein (for example by glycosylation or phosphorylation), when the biosensor is expressed in a host cell as defined above. Thus, the interaction between said analyte present in said cell and said sensor leads to structural rearrangement of the biosensor, which is reflected by a signal as described above. Said sensor can, for example, be a sugar, a lipid, a protein or a nucleic acid. Preferably, said sensor is a molecule of peptide nature.

According to a preferred embodiment of the invention, the biosensitive sensors include, without limitation, peptides such as mellitin, hydrid polypeptides (that is to say popylpeptides resulting from the fusion of at least two proteins), antibodies, enzymes or even enzyme substrates. Among said hydrid polypeptides, can be cited enzymes fused to binding sites (for example, calmodulin fused to peptide M13, or even GTPase fused to a domain capable of recognizing its active conformation). As an example of sensitive biosensor can also be cited a peptide sequence that is a protein kinase substrate, a peptide sequence that is a protease substrate, a cAMP binding domain, a phosphorylated amino acid binding domain (FHA), a glutamate binding domain (YbeJ), a sucrose binding domain (for example MBP, which binds maltose), and a $Ca^{2+}$ binding domain such as Troponin C and its fragments.

A biosensor according to the invention can thus allow the study of cell metabolism or cell signalling events.

In the context of the present invention, the biosensor comprises a cyan fluorescent protein displaying a reduced pH sensitivity linked, by a covalent or non covalent bond, to said sensitive biosensor. Thus, when this biosensor is expressed in a host cell, the interaction between the analyte present in said cell and said sensor leads to structural rearrangement of said biosensor which is reflected by a modification of the fluorescence emission of the fluorescent protein to which it is fused. By <<modification of fluorescence emission>>, it is meant herein a variation in the fluorescence intensity emitted by said protein characterized in that said variation is proportional to the concentration or activity of said analyte, or reflects the presence of this analyte. The fluorescence intensity can be measured as described previously.

According to a preferred embodiment, the biosensor of the invention further comprises a fluorescent protein whose absorption spectrum partially overlaps with the emission spectrum of the cyan protein of said biosensor.

According to a particular embodiment, the fluorescent protein whose absorption spectrum partially overlaps with the emission spectrum of the cyan protein is directly linked to said biosensor. By <<Directly linked>>, it is meant herein that said protein is linked, covalently or non-covalently, to the biosensitive sensor of said biosensor.

According to another particular embodiment, the fluorescent protein whose absorption spectrum partially overlaps with the emission spectrum of the cyan protein is indirectly linked to the biosensor. By <<Indirectly linked>>, it is meant herein that said protein is linked to the biosensitive sensor of said biosensor via a molecule, for example via non-covalent bonds between said molecule and said sensor.

Preferably, the fluorescent protein whose absorption spectrum partially overlaps with the emission spectrum of the cyan protein of the invention displays an absorbance maximum comprised between 495 and 600 nm, advantageously between 500 and 590 nm, and even more advantageously between 510 and 580 nm, and even more advantageously between 520 and 570 nm, and between 550 and 570 nm. Examples of fluorescent proteins which can be fused in this way to the protein of the invention via a biosensitive sensor includes, without limitation, yellow fluorescent proteins such as YFP, Topaz, EYFP, YPET, SYFP2, Citrin, Venus, cp-Venus, fluorescent orange proteins such as Kusabira Orange, Kusabira Orange2, mOrange, mOrange2, dTomato, dTomato-Tandem, DsRed and its variants (DsRed2, DsRed-Express (T1), DsRed-Express2, DsRed-Max, DsRed-Monomer), TagRFP and TagRFP-T, red fluorescent proteins such as mRuby, mApple, mStrawberry, AsRed2, mRFP1, JRed, mCherry, eqFP611, tdRFP611, HcRed1, mRaspberry, as well as fluorescent proteins emitting in the far red such as tdRFP639, mKate, mKate2, Katushka, tdKatushka, HcRed-Tandem, mPlum and AQ143 (Day et al., 2009). Preferably, the fluorescent protein whose absorption spectrum partially overlaps with the emission spectrum of the cyan protein of the invention is selected among the yellow or orange fluorescent proteins as described above.

In a particularly advantageous manner, the fluorescent protein whose absorption spectrum partially overlaps with the emission spectrum of the cyan protein of the invention displays itself a reduced pH sensitivity. This protein can then be selected among the proteins Citrine, Venus, cp-Venus, TagRFP and TagRFP-T, preferably among TagRFP and TagRFP-T, and even more preferably this protein is TagRFP (Merzlyak et al., 2007).

According to a particularly advantageous embodiment of the invention, the biosensor of the invention comprises, in addition to a cyan fluorescent protein of the invention whose sequence comprises at least the 65S and 148G mutations, the TagRFP fluorescent protein. According to a preferred embodiment, said cyan fluorescent protein comprises or consists of a protein sequence selected from the group consisting of the sequences SEQ ID NO:12, SEQ ID NO:80 or SEQ ID NO:82, and even more preferably of the proteic SEQ ID NO:82 sequence.

Fusion of the biosensitive sensor to a fluorescent protein for the construction of the biosensor of the invention is carried out using genetic engineering, enzymatic or chemical coupling techniques known to the skilled person in the art. Such techniques are described in Sambrook et al. (2001) and Ausubel et al. (2011).

According to a particularly advantageous embodiment of the invention, the biosensor can be generated by mutating existing biosensors according to the method of the invention, that is to say by introducing at least one unique mutation allowing the pH sensitivity to be reduced. Among existing biosensors, which are besides known to the skilled person in the art, can be cited, without limitation, the biosensors Epac, Epac2, ECFP-YbeJ-Venus, ECFP-MBP-EYFP, CFP-TnC-Citrine, Aldus, Atomic, Erkus, Phocus, Picchu, AKAR, AKAR1 (Zhang et al., 2001), AKAR2 (Zhang et al., 2005), AKAR2.2 (Dunn et al., 2006), AKAR3, BKAR, CKAR and DKAR. Preferably, the mutated biosensor is an AKAR type biosensor, and even more preferably the biosensor is AKAR2.2.

According to an advantageous embodiment, the 65S and 148G mutations are introduced into said biosensor according to the method of the invention. Thus, when the 65S and 148G mutations are introduced into the AKAR2.2 biosensor, the latter comprises a cyan fluorescent protein comprising the SEQ ID NO:82 sequence. Even more preferably, the 65S and 148G mutations are introduced into the AKAR2.2 biosensor according to the method of the invention and the Citrine expressed by it is replaced by the TagRFP protein by means of classical genetic engineering, enzymatic or chemical coupling known techniques to the skilled person in the art, said biosensor thereby comprising a cyan fluorescent protein including the SEQ ID NO:82 sequence and the TagRFP orange fluorescent protein.

For more detailed information regarding the biosensors, the skilled person in the art can refer to the publications by M. C. Morris (2010) and Frommer et al. (2009).

The biosensors of the invention can be used according to the techniques described below, which are more preferably according to the invention FRET and/or FLIM.

Another aspect of the present invention relates to the use of the products of the invention (notably the mutated fluorescent proteins, nucleic acids coding for these proteins, recombinant vectors, host cells and biosensors as defined above).

These include, without limitation, flow cytometry (FACS), conventional imaging methods such as photon or confocal microscopy, real-time quantitative imaging methods such as fluorescence correlation spectroscopy (FCS) and variations thereof (for example FCCS), Förster resonance energy transfer (FRET), bioluminescence resonance energy transfer (BRET), fluorescence lifetime imaging microscopy (FLIM), fluorescence redistribution after photobleaching (FRAP), fluorescence loss induced by photobleaching (FLIP), time-correlated single photon counting (TCSPC), anisotropy and fluorescence depolarisation, photoactivation localisation microscopy (PALM), stochastic optic reconstruction microscopy (STORM) stimulated emission depletion microscopy (STED). This also includes high throughput detection methods such as high content screening, high throughput microscopy and conventional or ultra high throughput microfluidic methods.

The most preferable imaging methods used according to the invention are FRET and FLIM.

The term <<Förster resonance energy transfer>> (FRET) refers herein to non-radiative transfer of excitation energy originating from a fluorescent molecule <<donor>> of photons to an <<acceptor>> fluorescent molecule, this transfer only being possible when the <<donor>> of photons is sufficiently close to the <<acceptor>> molecule, that is at a distance of 10 to 100 Å depending on the geometry of the molecules and the observation system (Heyduk (2002), Truong et al. (2001), Issad et al. (2003), Boute et al. (2002)). This method allows the quantification of either the decrease in fluorescence of the <<donor>> of photons (for example by measuring the fluorescence intensity or lifetime of this <<donor>>) or the increase in fluorescence of the <<acceptor>> (for example by measuring the fluorescence intensity of this <<acceptor>>). Any method derived from FRET also applies to the present invention. In the case of FRET, the mutated cyan fluorescent protein according to the invention is preferably used as a <<donor>> of photons.

The <<bioluminescence resonance energy transfer>>, or BRET, differs from FRET in that the energy of the <<donor>> originates from a bioluminescent molecule, such as luciferin (eg: coelenterazine), which is excited in the presence of an enzyme (for example luciferase) and emits photons. These photons are then transferred to an <<acceptor>> fluorescent molecule of GFP type which emits fluorescence if the conditions of proximity and geometry for energy transfer are met. The mutated fluorescent protein according to the invention must therefore be used as an <<acceptor>> fluorescent molecule in this type of application.

The FLIM (or fluorescence lifetime imaging microscopy) is a technique that allows the measurement the fluorescence decay of a fluorescent molecule and the quantification of the fluorescence lifetime of this molecule. This technique can be used alone or in combination with FRET, particularly for the localisation of protein-protein interactions or to study cell signalling. Any method derived from FLIM such as tomographic FLIM, multiplex FLIM, multi-well plate automated FLIM or confocal endomicroscopy FLIM is included in the present invention. In the case where the FLIM technique is used in the present invention, the mutated cyan fluorescent protein is preferably a donor of photons.

For any further detail regarding the above-mentioned techniques, the skilled person in the art can refer to the articles by Day et al. (2009), Trugnan et al. (2004), and Kumar et al. (2011).

A particular embodiment relates to the use of the products of the invention in screening methods for chemical compounds and/or cells. Preferably, said screening methods are high throughput detection methods such as high content screening, flow cytometry, high throughput microscopy, microfluidic methods (conventional or ultra-high throughput) and plate reader assays.

Another particular embodiment relates to the use of said products in toxicology, genotoxicity or environmental pollution detection tests carried out in solution, more particularly from a sample, a biological extract, a cell, tissue or a living organisms.

The present invention will be better understood in the light of the examples hereafter.

FIGURES

FIG. 1: pH dependence of the fluorescence properties of the purified ECFPr (SEQ ID NO:4). Graph A: Absorption spectra normalised to the same area Graph B: Fluorescence emission spectra normalised to the same area ($\lambda$ex=420 nm).

Graph C: Fluorescence intensity emitted at 474 nm (Δλ=6 nm) normalised to the maximum value, as a function of pH. Graph D: Fluorescence lifetime <τ> (ns), as a function of pH.

Figure 2:
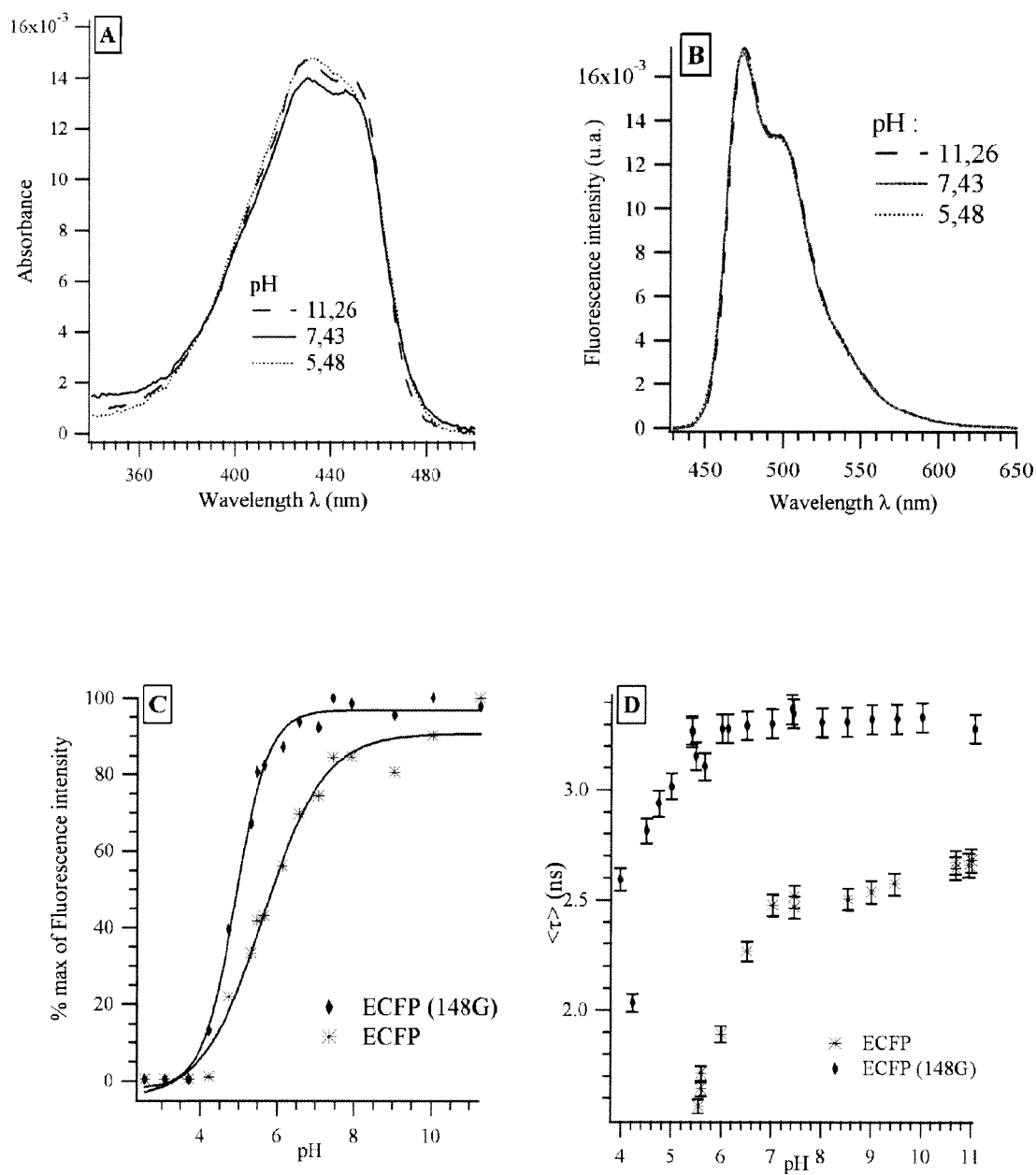

FIG. 2: pH dependence of the fluorescence properties of the purified ECFPr (148G). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value, as a function of pH-comparison with ECFPr. Graph D: Fluorescence lifetime <τ> (ns), as a function of pH-comparison with ECFPr.

Figure 3:
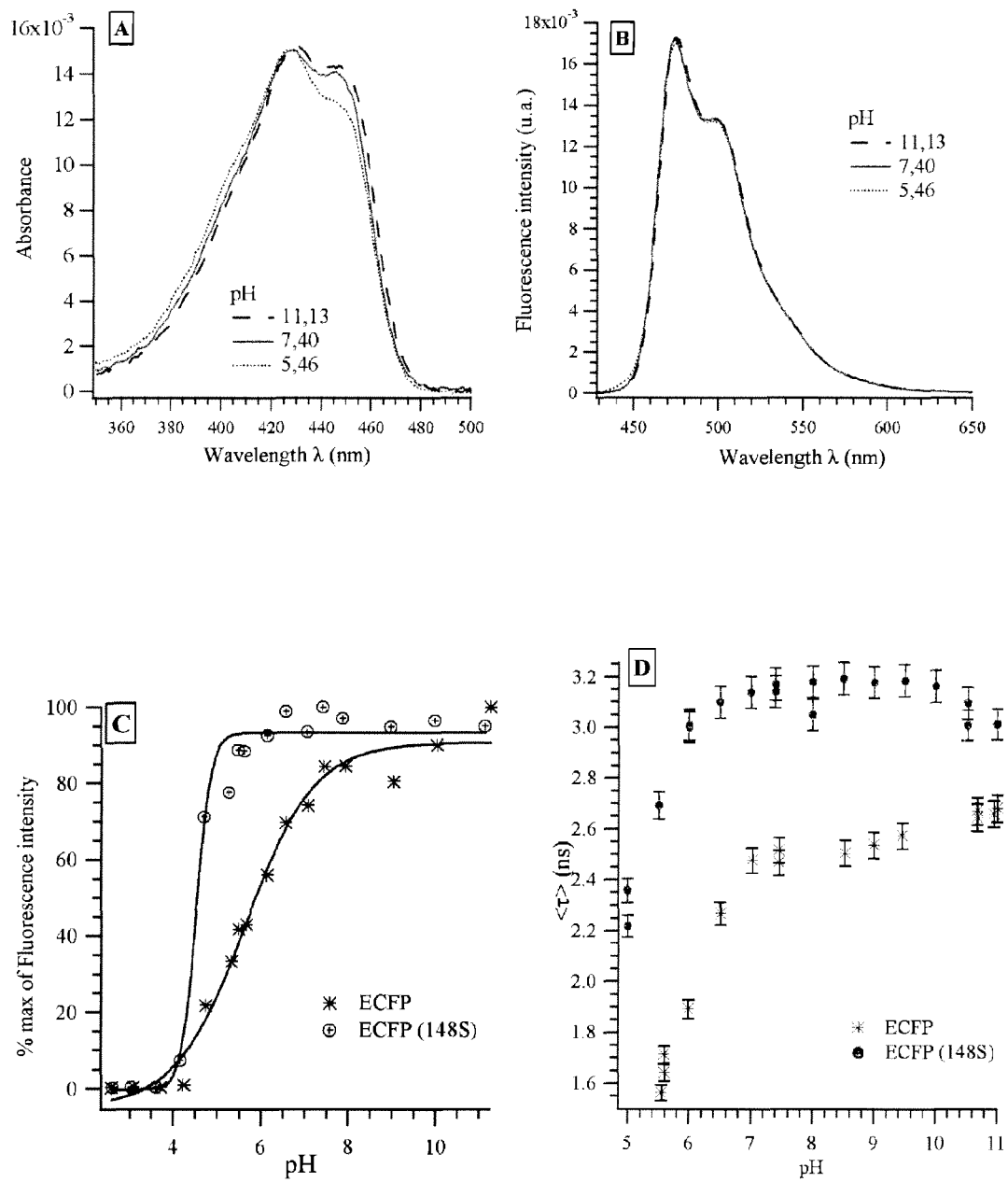

FIG. 3: pH dependence of the fluorescence properties of the purified ECFPr (148S). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value-comparison with ECFPr. Graph D: Fluorescence lifetime—comparison with ECFPr.

Figure 4:
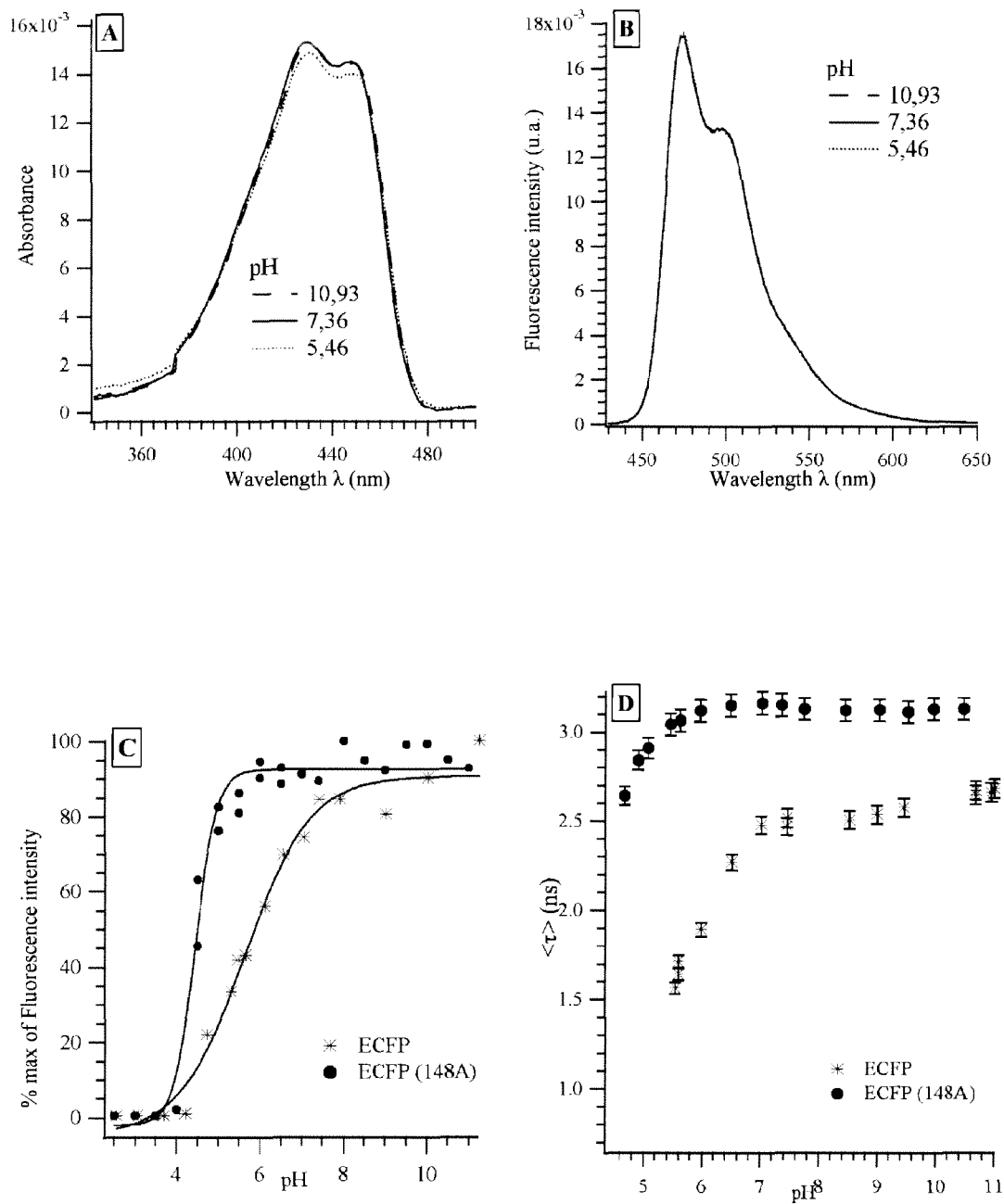

FIG. 4: pH dependence of the fluorescence properties of the purified ECFPr (148A). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value —comparison with ECFP. Graph D: Fluorescence lifetime—comparison with ECFPr.

Figure 5:
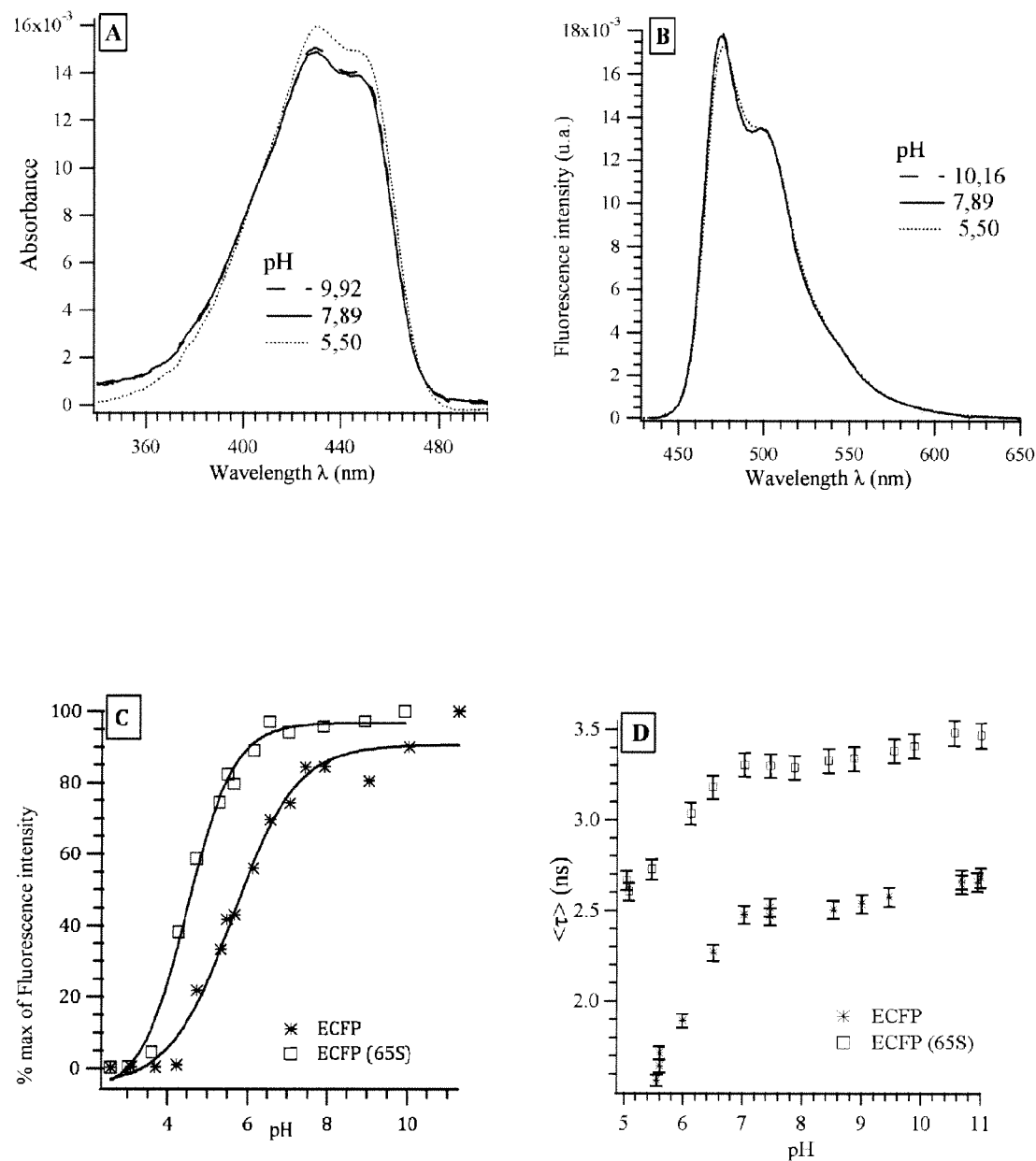

FIG. 5: pH dependence of the fluorescence properties of the purified ECFPr (65S). Graph A: Absorption spectra normalised to the same area. Graph B: Fluorescence emission spectra normalised to the same area u (λex=420 nm). Graph C: Fluorescence intensity emitted at 474 nm (Δλ=6 nm) normalised to the maximum value comparison with ECFPr. Graph D: Fluorescence lifetime-comparison with ECFPr.

Figure 6:
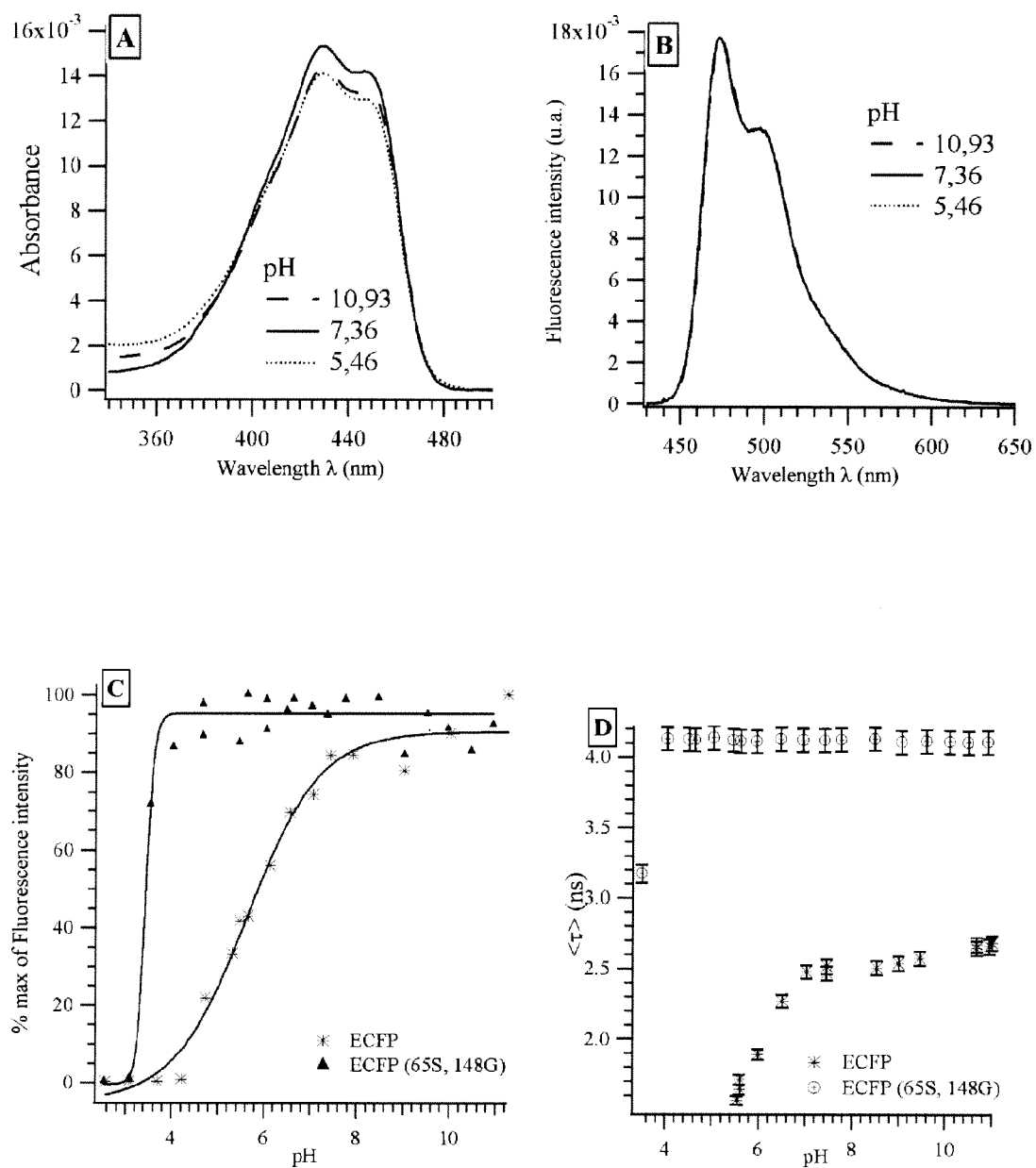

FIG. 6: pH dependence of the fluorescence properties of the purified ECFPr (65S, 148G). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value—comparison with ECFPr. Graph D: Fluorescence lifetime—comparison with ECFPr.

Figure 7:
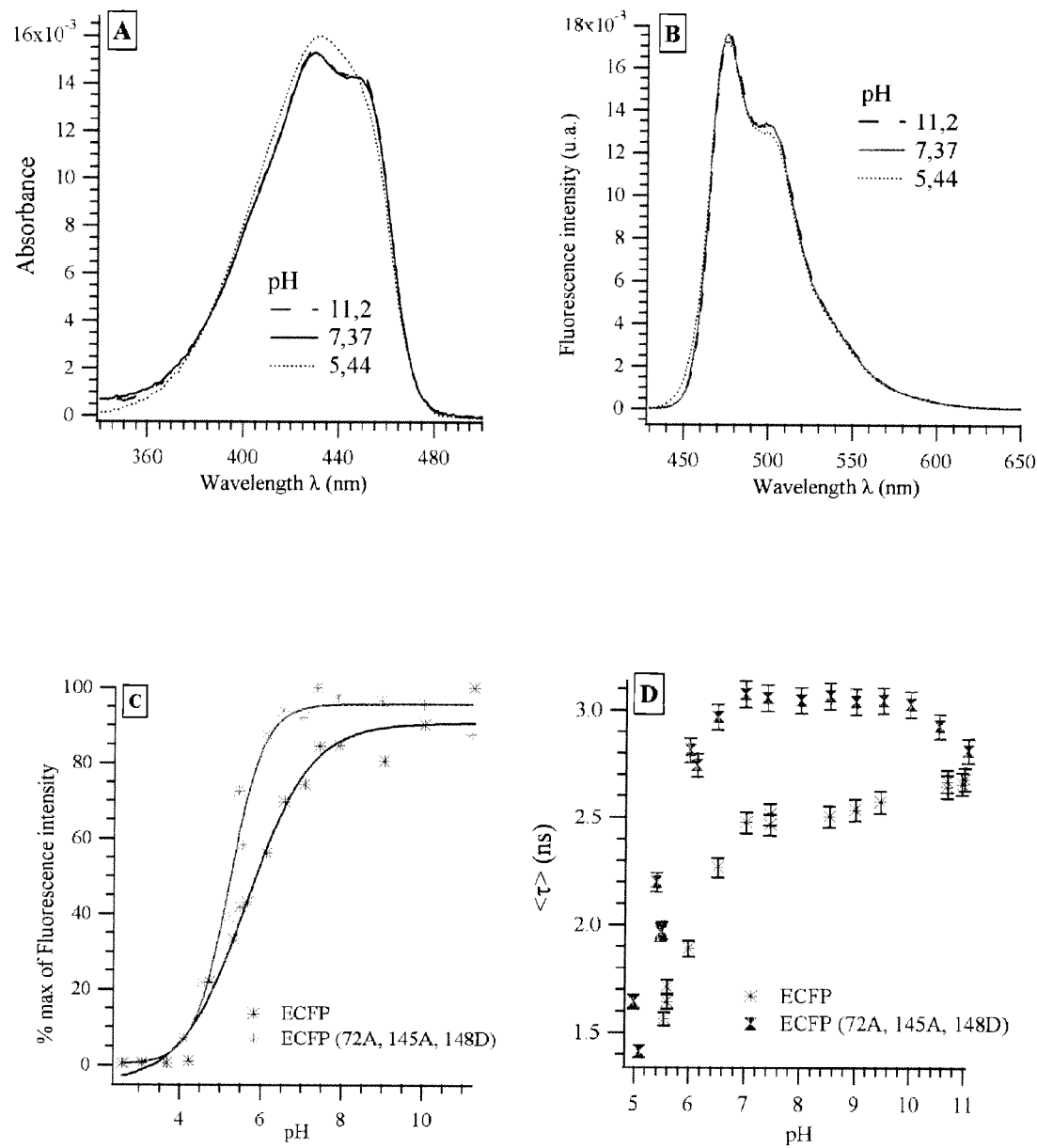

FIG. 7: pH dependence of the fluorescence properties of the purified ECFPr (72A, 145A, 148D). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value, as a function of pH-comparison with ECFPr. Graph D: Fluorescence lifetime <τ> (ns), as a function of pH-comparison with ECFPr.

Figure 8:
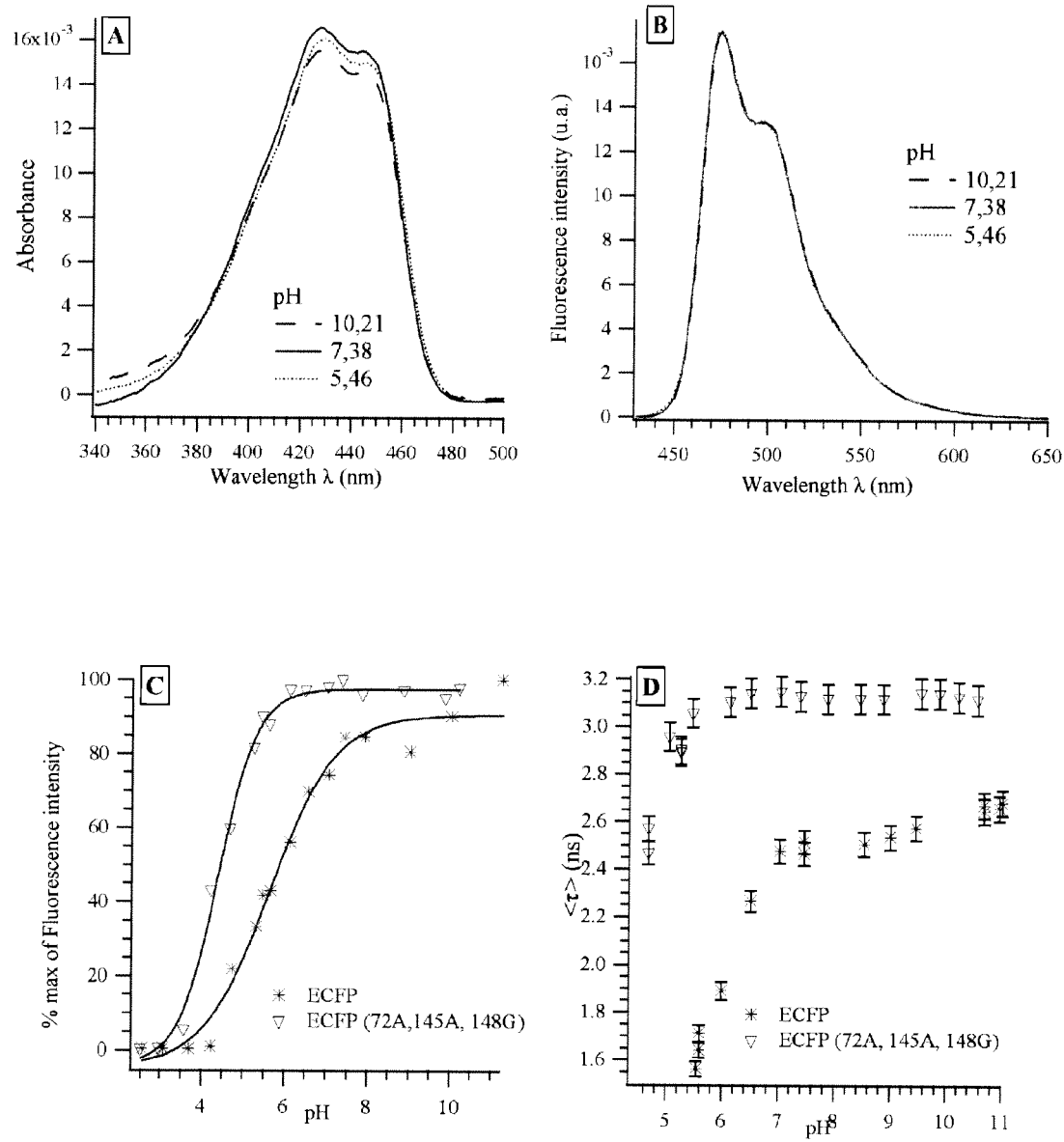

FIG. 8: pH dependence of the fluorescence properties of the purified ECFPr (72A, 145A, 148G). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value-comparison with ECFPr. Graph D: Fluorescence lifetime-comparison with ECFPr.

Figure 9:
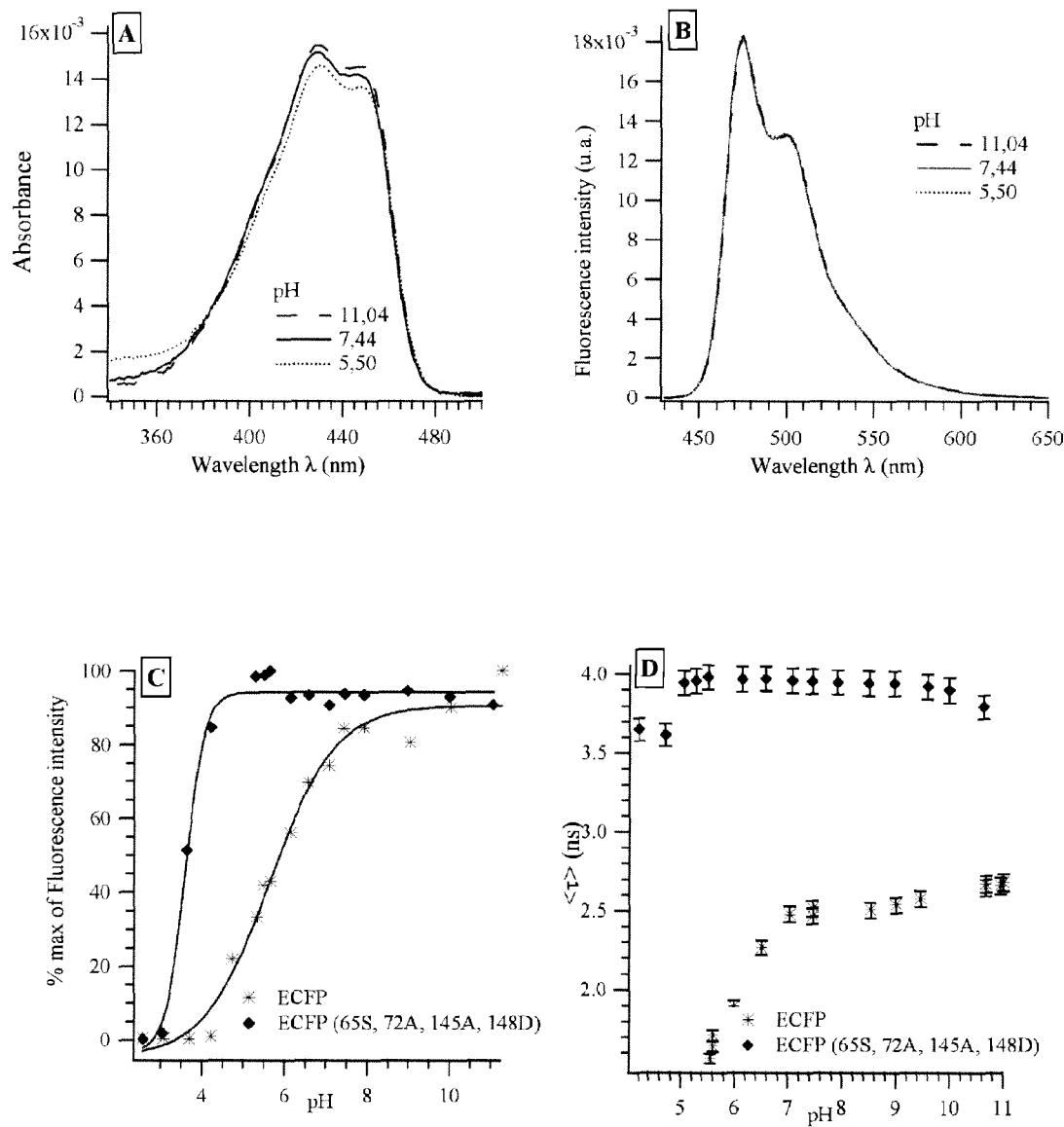

FIG. 9: pH dependence of the fluorescence properties of the purified ECFPr (65S, 72A, 145A, 148D). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value-comparison with ECFPr. Graph D: Fluorescence lifetime-comparison with ECFPr.

Figure 10:
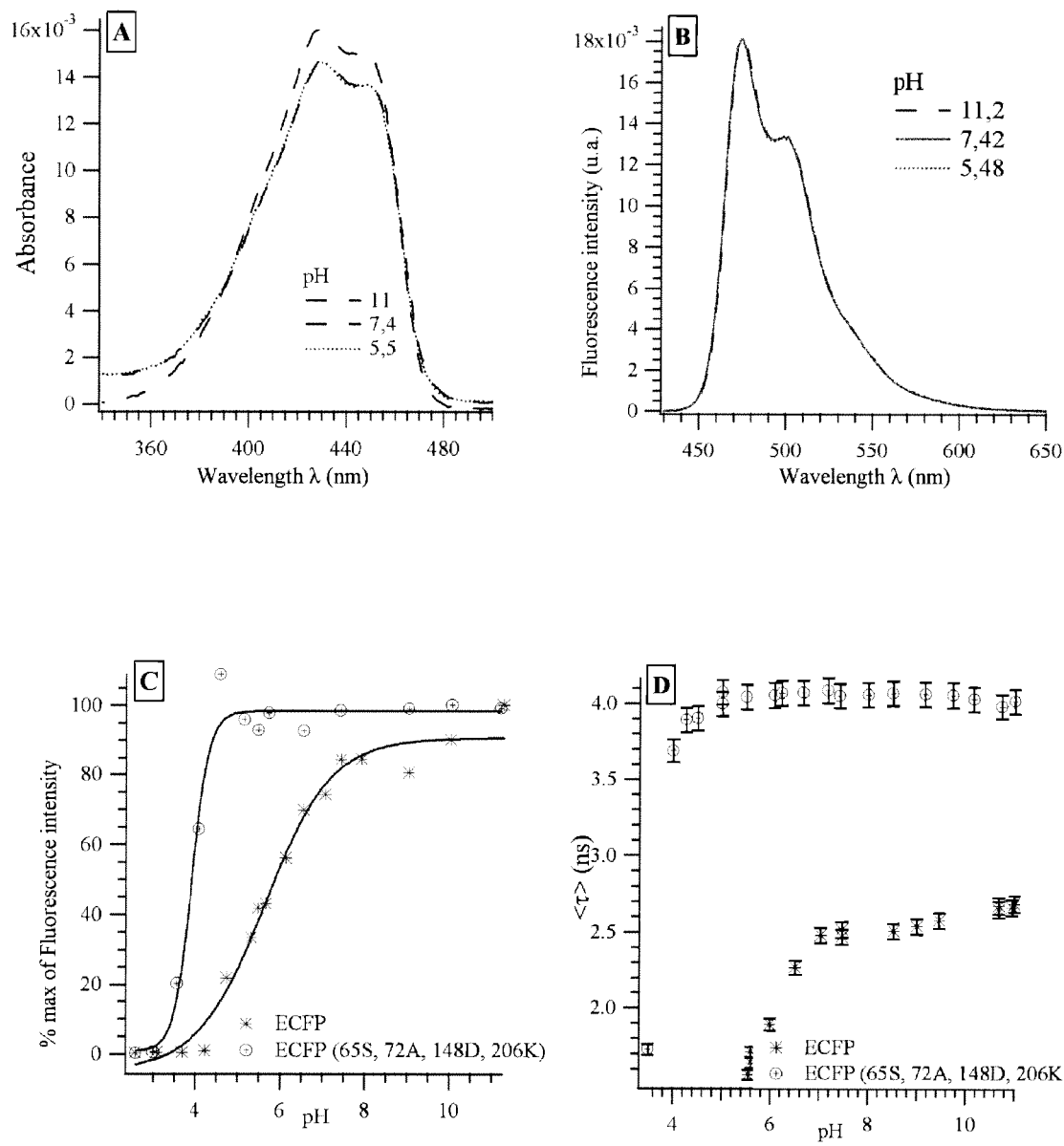

FIG. 10: pH dependence of the fluorescence properties of the purified ECFPr (65S, 72A, 148D, 206K). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value-comparison with ECFPr. Graph D: Fluorescence lifetime-comparison with ECFPr.

Figure 11:
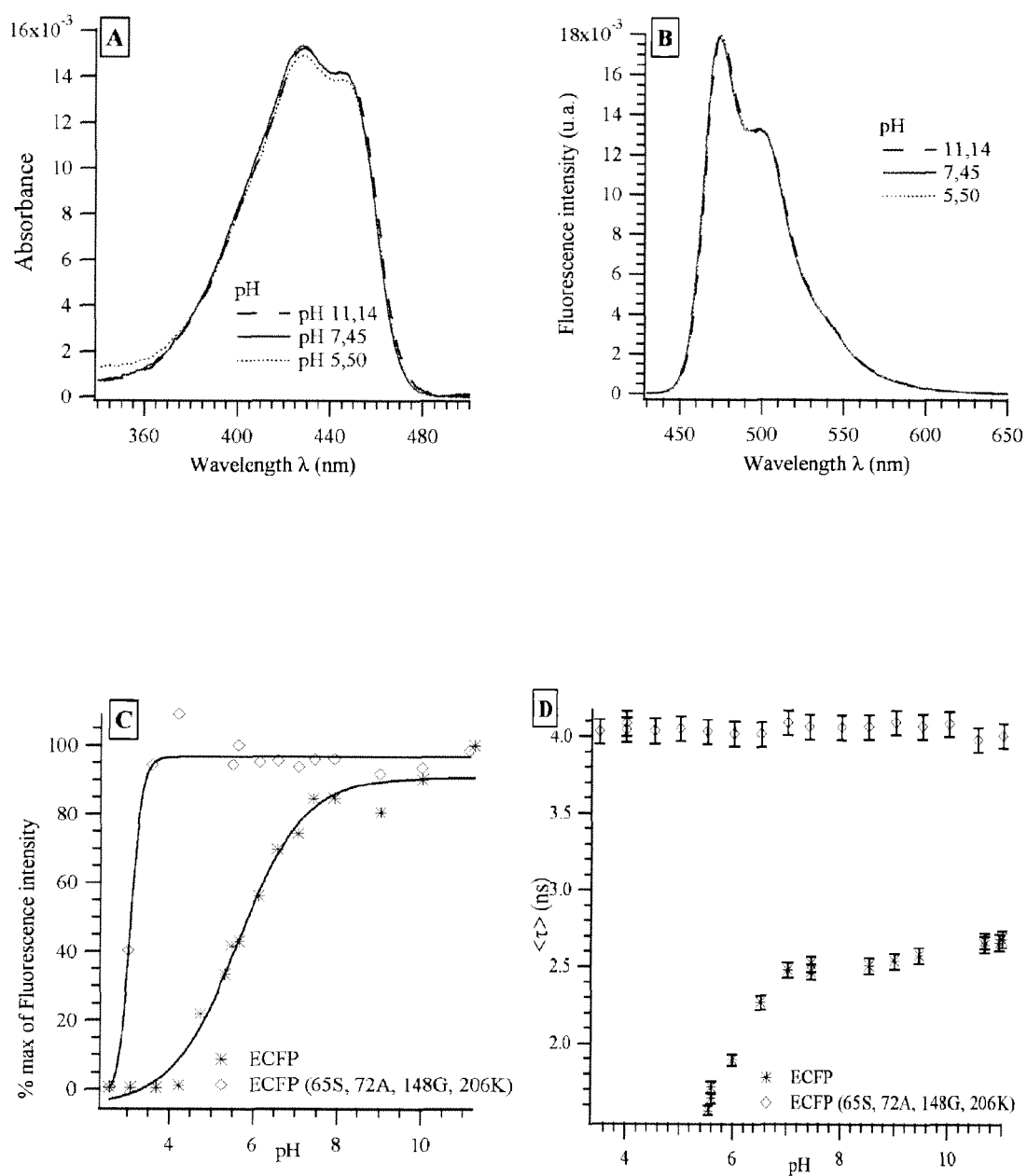

FIG. 11: pH dependence of the fluorescence properties of the purified ECFPr (65S, 72A, 148G, 206K). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value—comparison with ECFPr. Graph D: Fluorescence lifetime-comparison with ECFPr.

Figure 12:
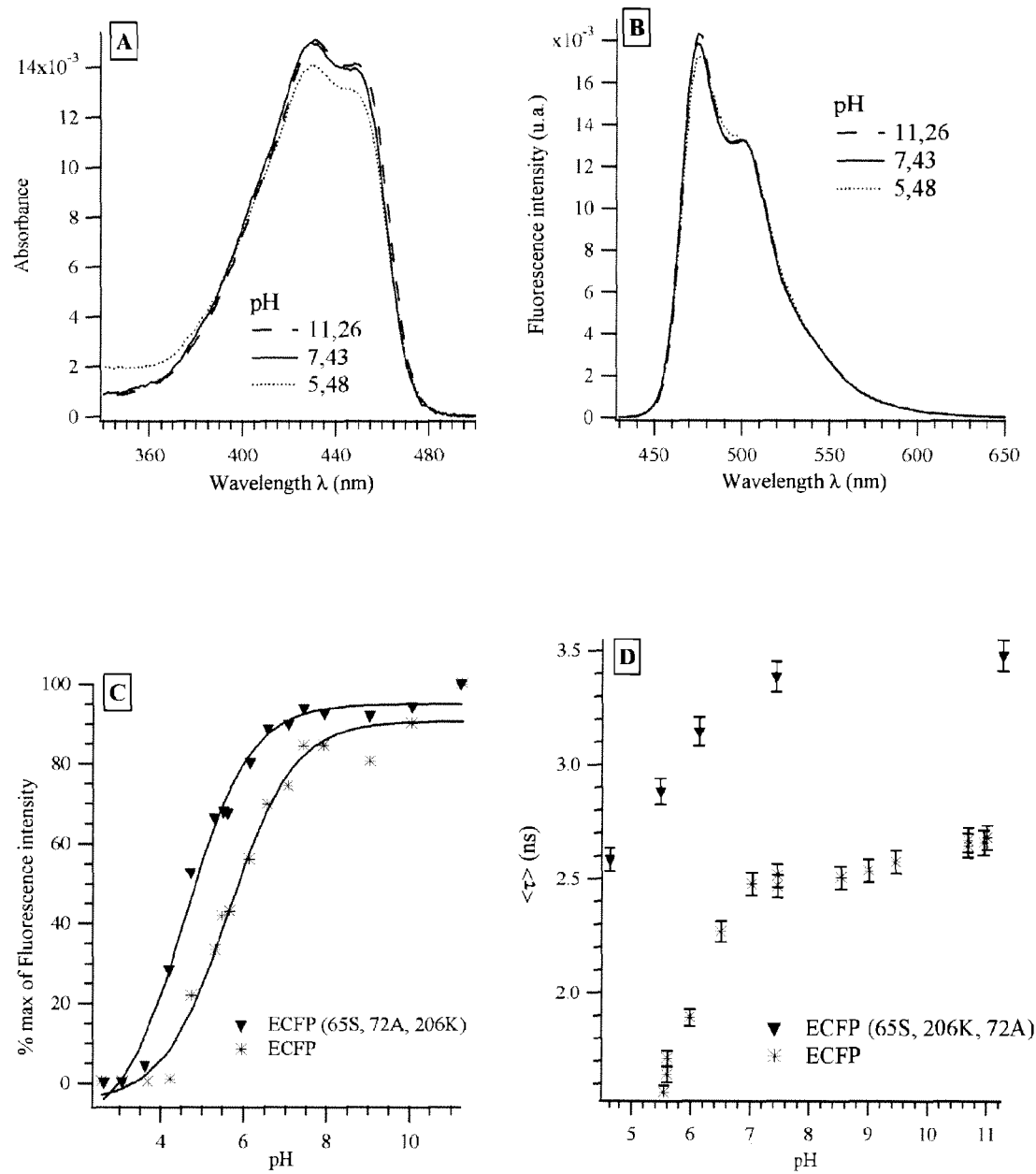

FIG. 12: pH dependence of the fluorescence properties of the purified ECFPr (65S, 72A, 206K). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value, as a function of pH-comparison with ECFPr; Graph D: Fluorescence lifetime <τ> (ns), as a function of pH-comparison with ECFPr.

Figure 13:
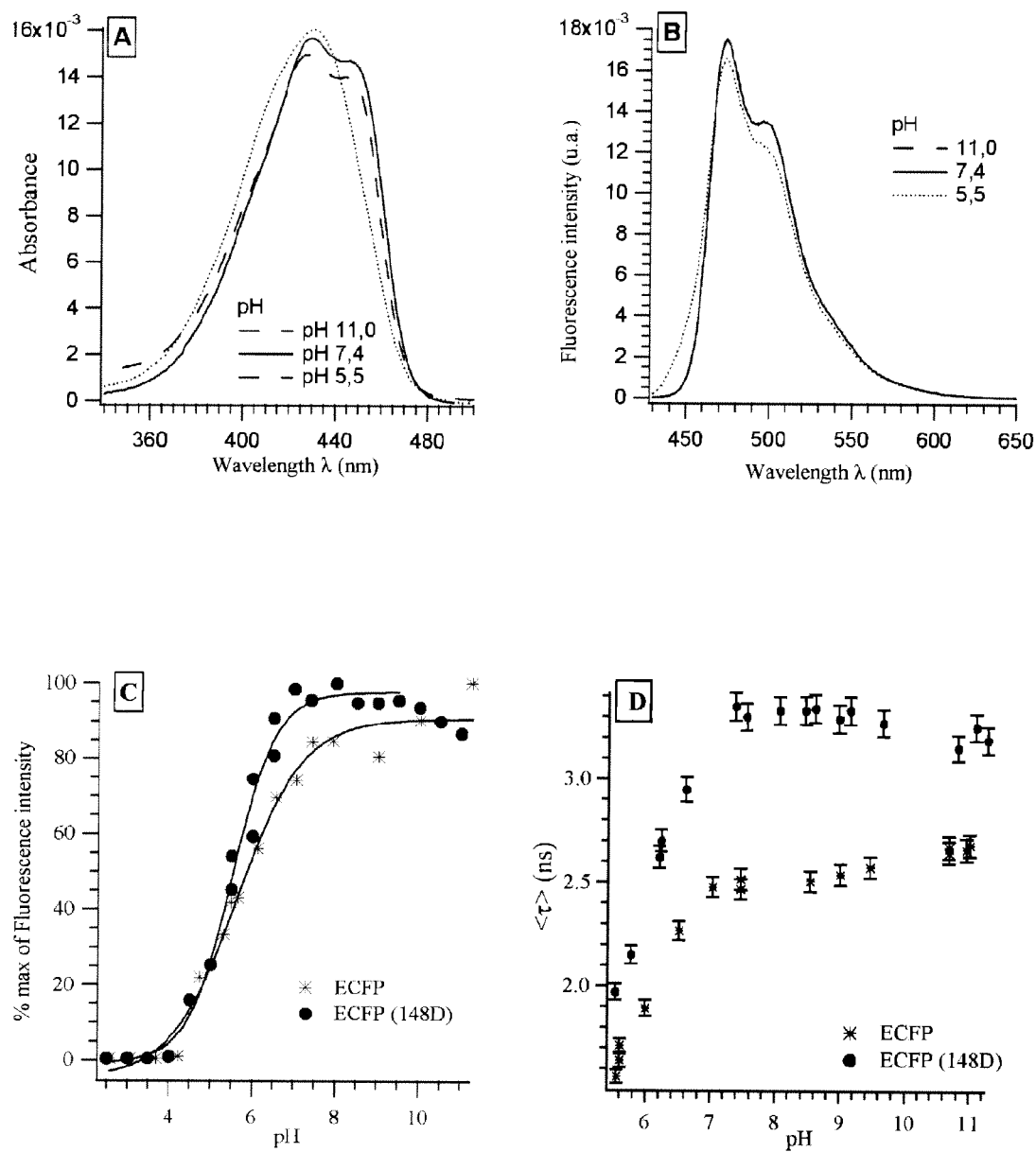

FIG. 13: pH dependence of the fluorescence properties of the purified ECFPr (148D). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value-comparison with ECFPr. Graph D: Fluorescence lifetime-comparison with ECFPr.

Figure 14:
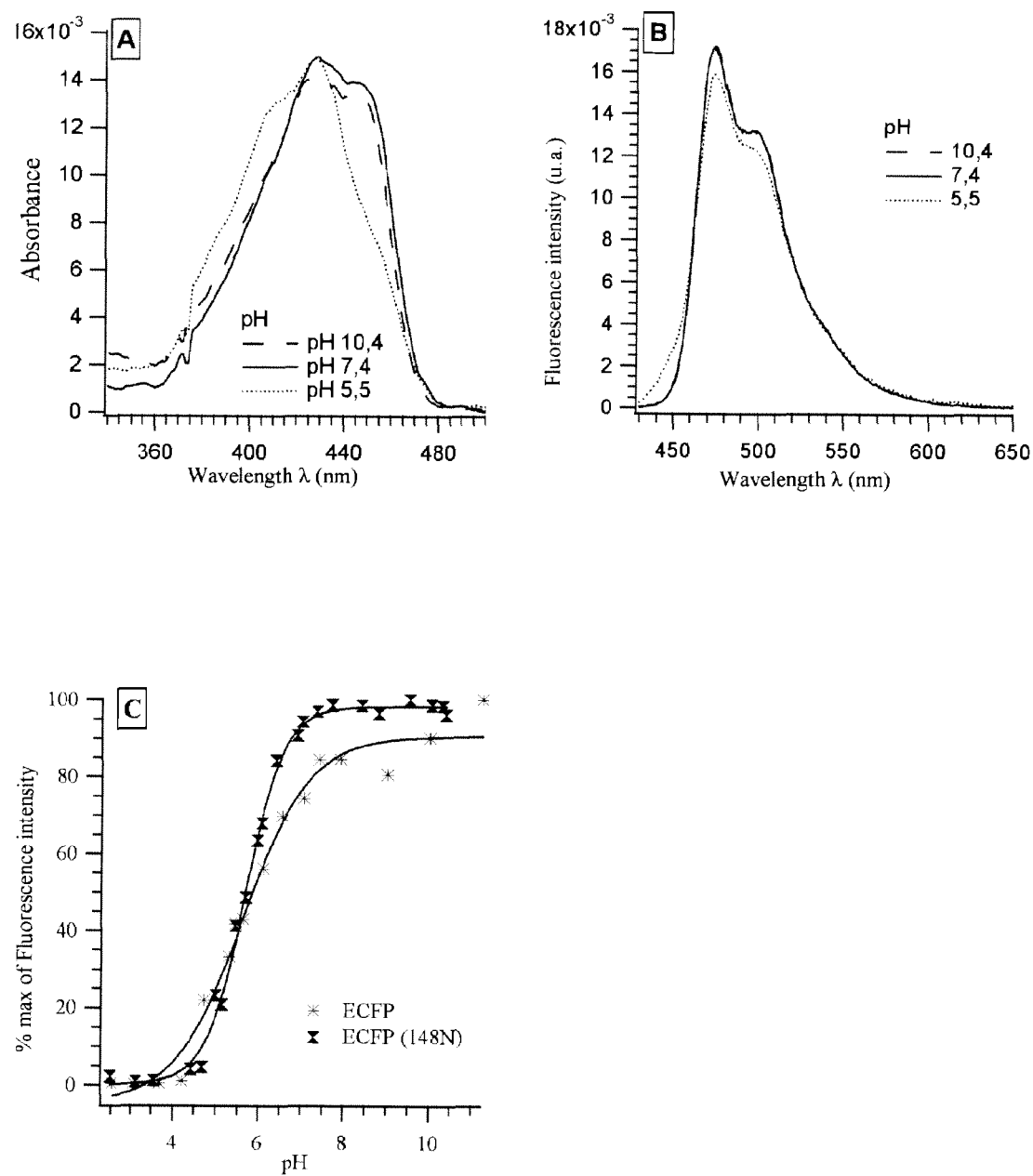

FIG. 14: pH dependence of the fluorescence properties of the purified ECFPr (148N). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value-comparison with ECFPr.

Figure 15:
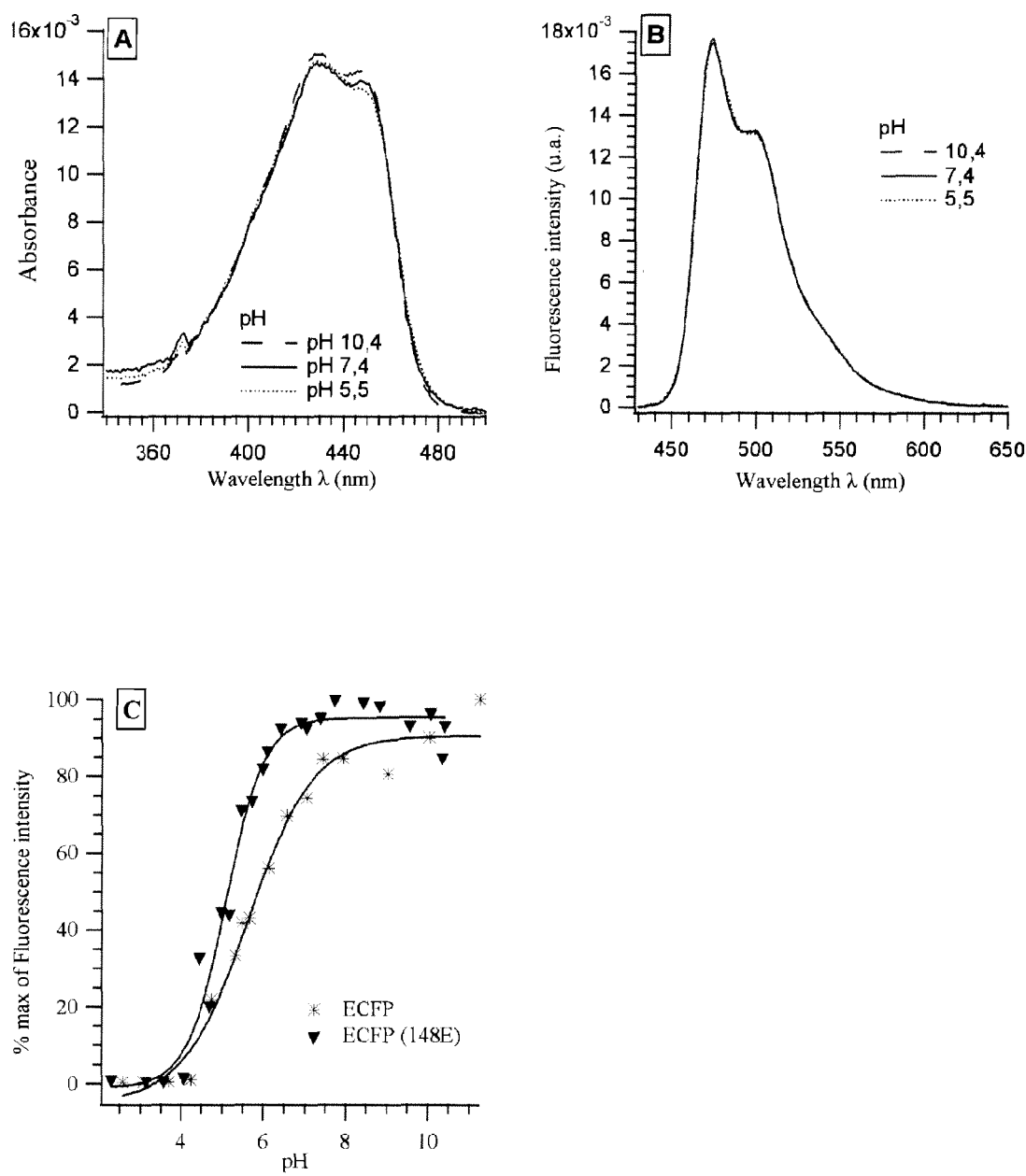

FIG. 15: pH dependence of the fluorescence properties of the purified ECFPr (148E). Graph A: Absorption spectra normalised to the same area Graph B: Fluorescence emission spectra normalised to the same area (λex=420 nm). Graph C: Fluorescence intensity emitted at 474 nm (Δλ=6 nm) normalised to the maximum value-comparison with ECFPr.

Figure 16:
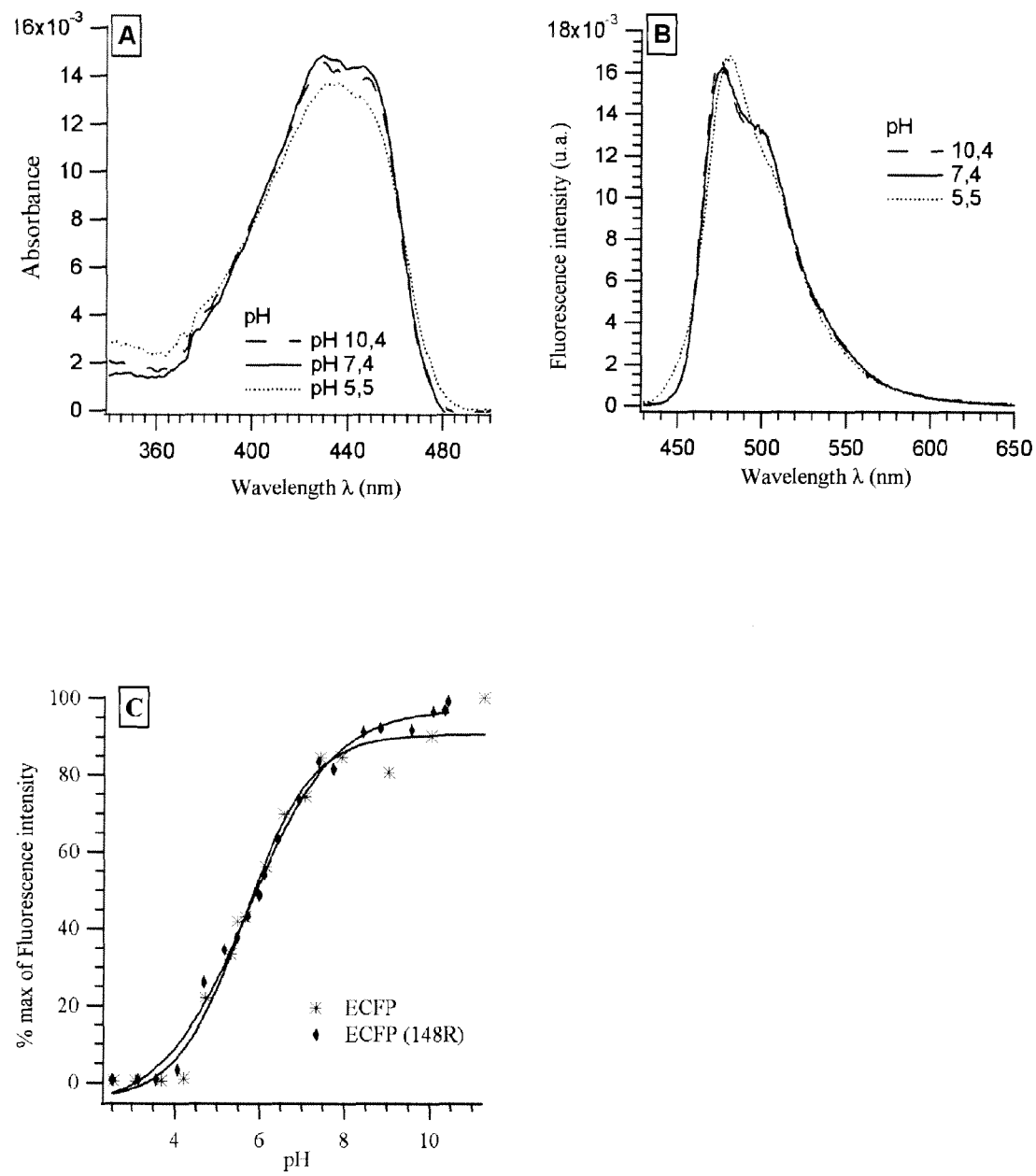

FIG. 16: pH dependence of the fluorescence properties of the purified ECFPr (148R). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value-comparison with ECFPr.

Figure 17:
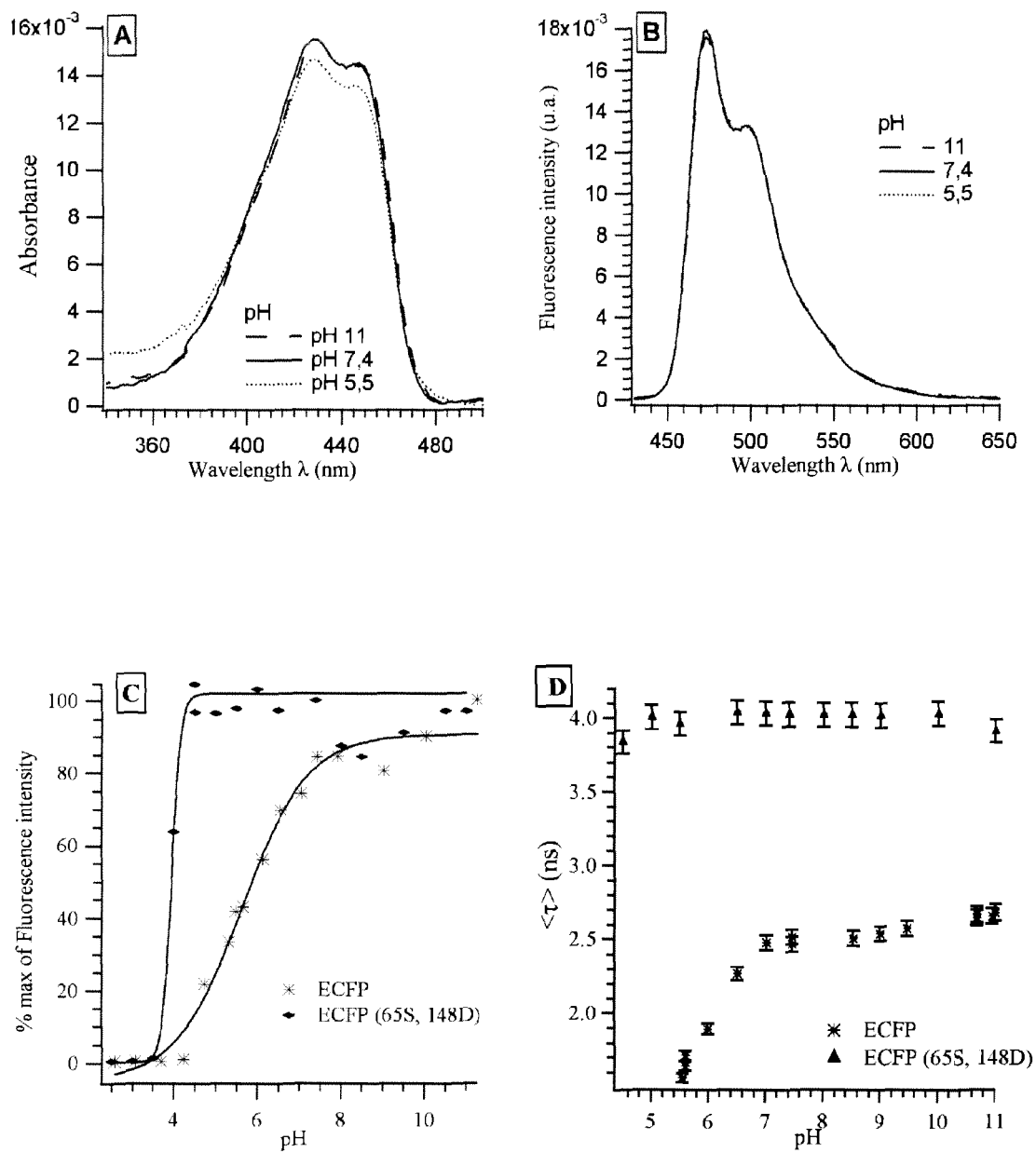

FIG. 17: pH dependence of the fluorescence properties of the purified ECFPr (65S, 148D). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value-comparison with ECFPr. Graph D: Fluorescence lifetime-comparison with ECFPr.

Figure 18:
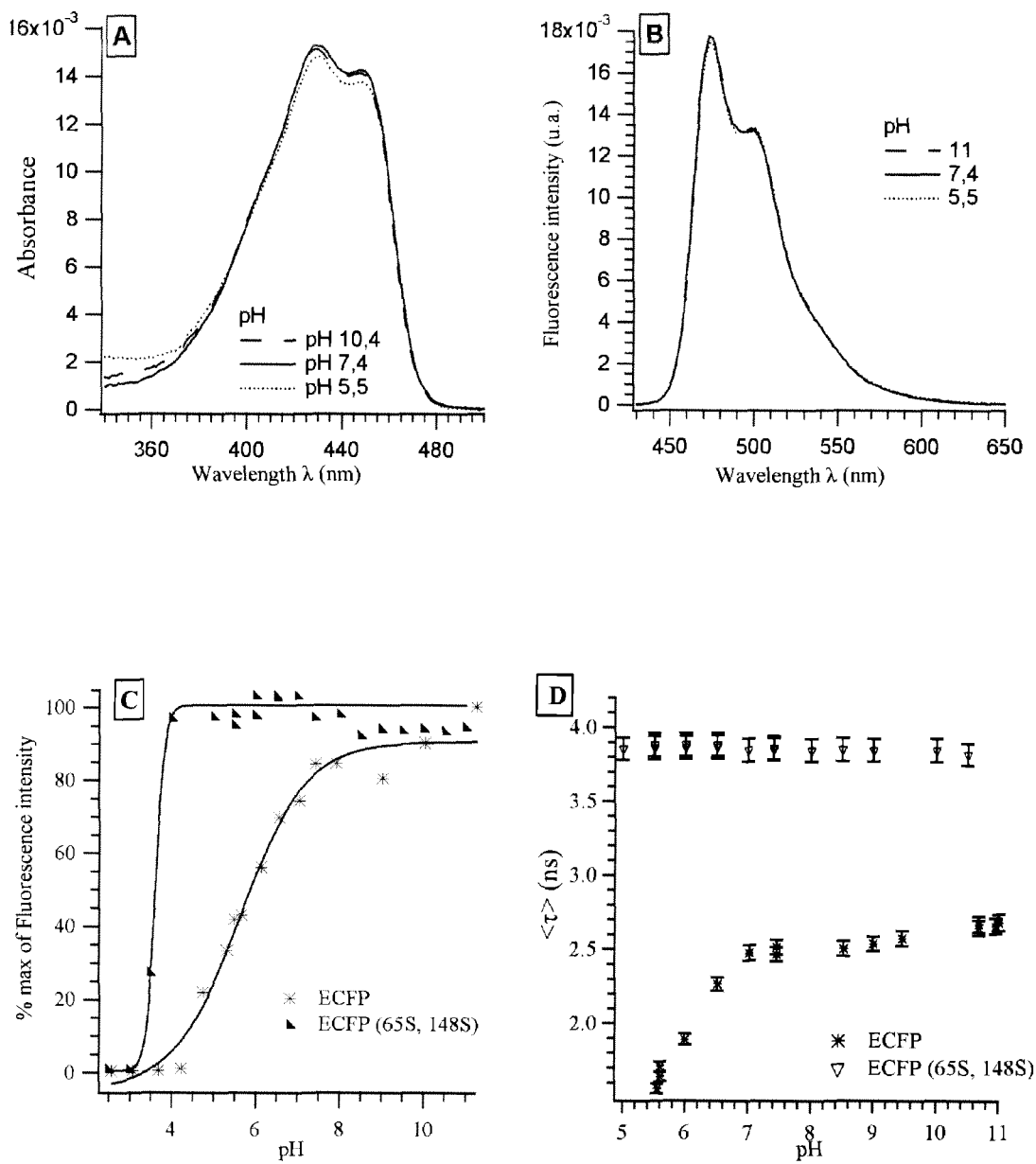

FIG. 18: pH dependence of the fluorescence properties of the purified ECFPr (65S, 148S). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value-comparison with ECFPr. Graph D: Fluorescence lifetime-comparison with ECFPr.

Figure 19:
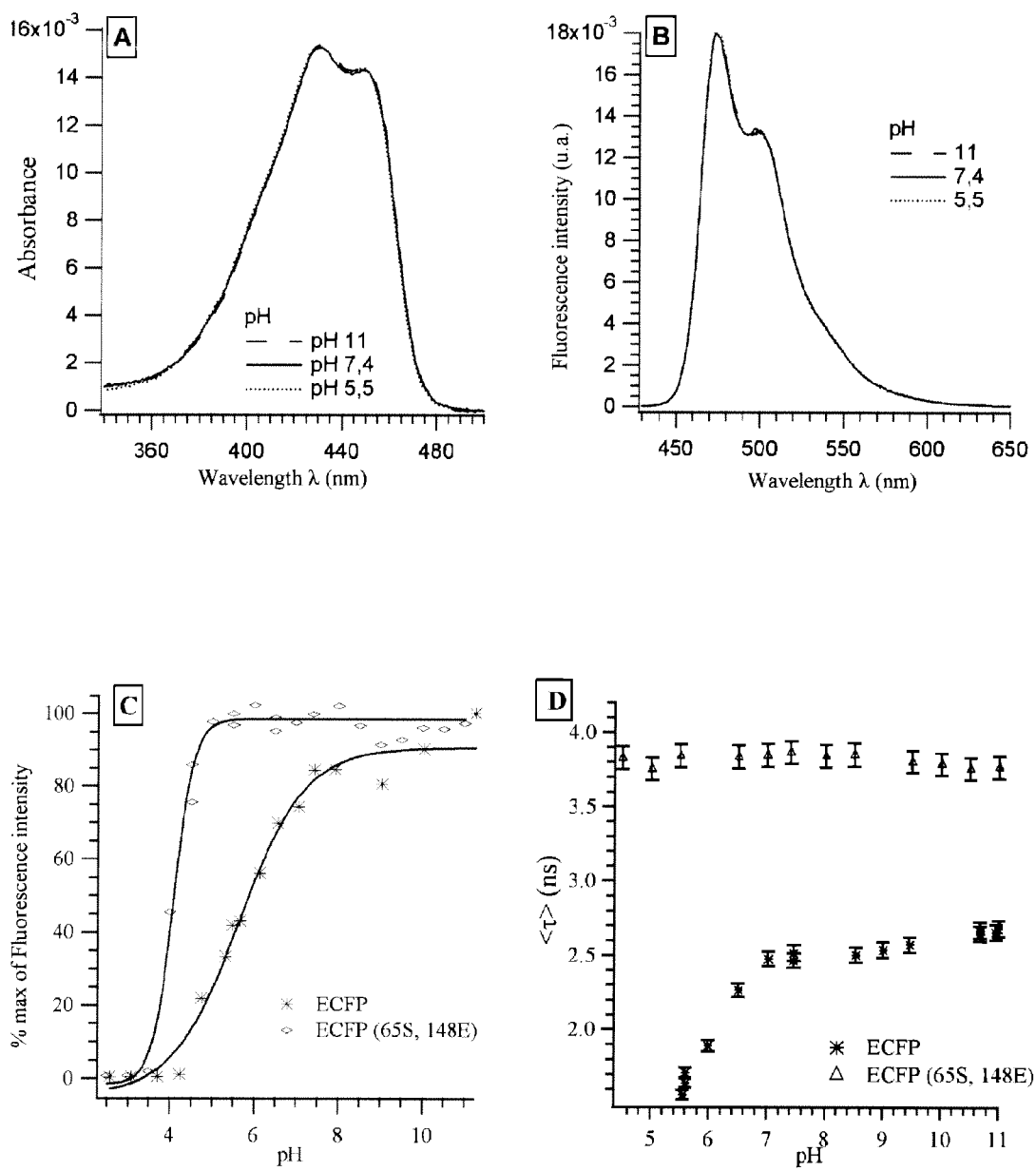

FIG. 19: pH dependence of the fluorescence properties of the purified ECFPr (65S, 148E). Graph A: Absorption spectra normalised to the same area. Graph B: Fluorescence emission spectra normalised to the same area (λex=420 nm). Graph C: Fluorescence intensity emitted at 474 nm (Δλ=6 nm) normalised to the maximum value—comparison with ECFPr. Graph D: Fluorescence lifetime—comparison with ECFPr.

Figure 20:
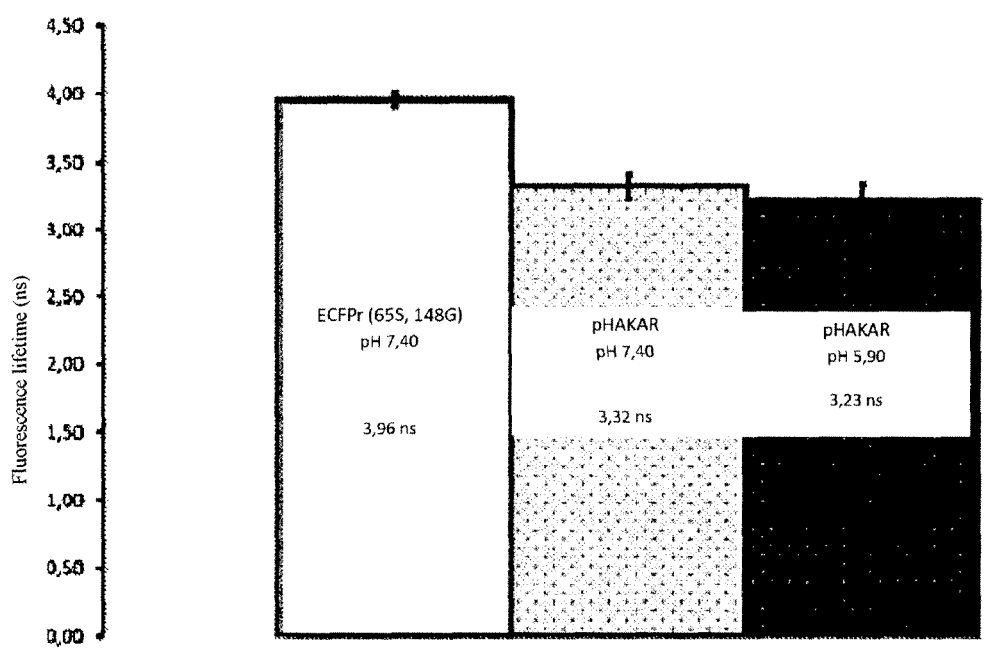

FIG. 20: Average lifetime of fluorescent protein ECFPr comprising at least the 65S and 148G mutations, expressed alone or incorporated into a biosensor—as a function of intracellular pH. BHK (baby hamster kidney) cells were transfected either with a plasmid coding only for ECFPr (65S, 148G) or with the pHAKAR biosensor.

Figure 21:
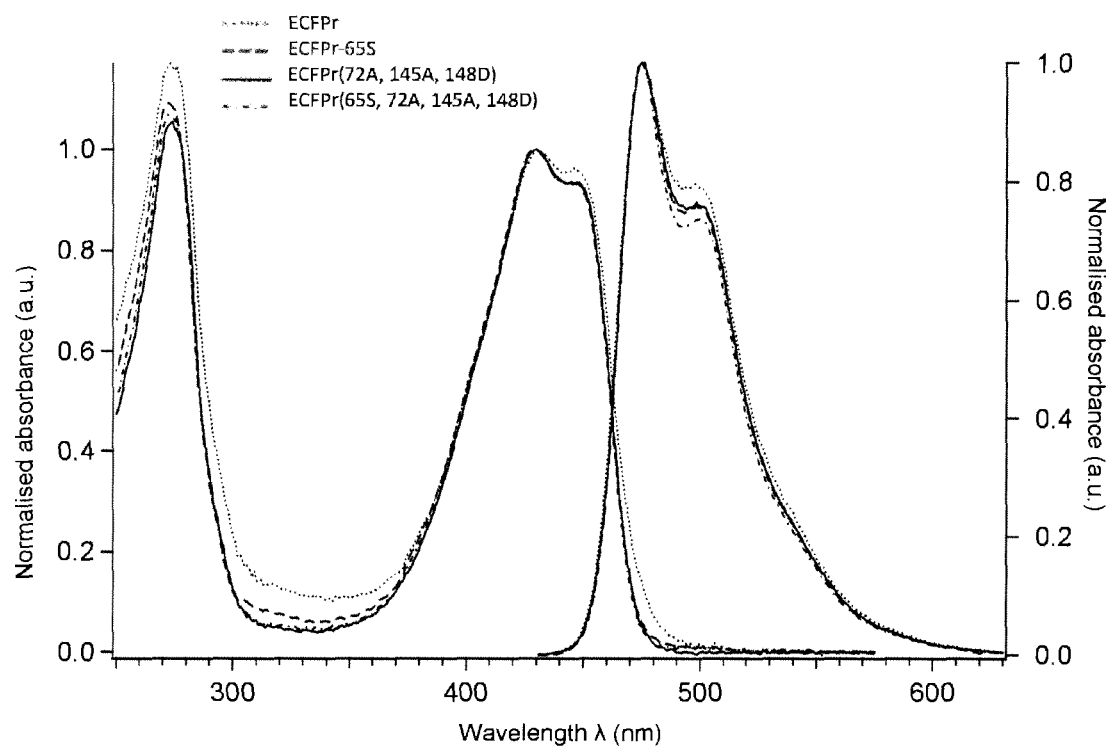

FIG. 21: Spectral properties of the cyan fluorescent proteins ECFPr, ECFPr (65S), ECFPr (72A, 145A, 148D) and ECFPr (65S, 72A, 145A, 148D). The absorption spectra (dotted lines) and emission spectra (solid lines) were normalised to the same area (maximum for the chromophore band). The emission spectra were recorded over an excitation wavelength λex, of 420 nm.

FIG. 22: Photophysical properties of the cyan fluorescent proteins, comprising or not the 65S mutation. ε: molar extinction coefficient; Q. Yield: quantum yield of fluorescent emission; $\tau_L$: value of the longest lifetime in the distribution of fluorescence life; $c_L$: relative amplitude of the time component of the longest fluorescence lifetime in the fluorescence life distribution; % Rev: percentage of loss in initial fluorescence intensity after sudden illumination of a density of 0.2 W/cm²; $\tau_{Rev}$(s): time constant of initial decay of fluorescent intensity; $\tau_{Irrev}$ (s): exponential time constant of the irreversible loss in fluorescence under prolonged illumination of a density of 0.2 W/cm².

Figure 23:
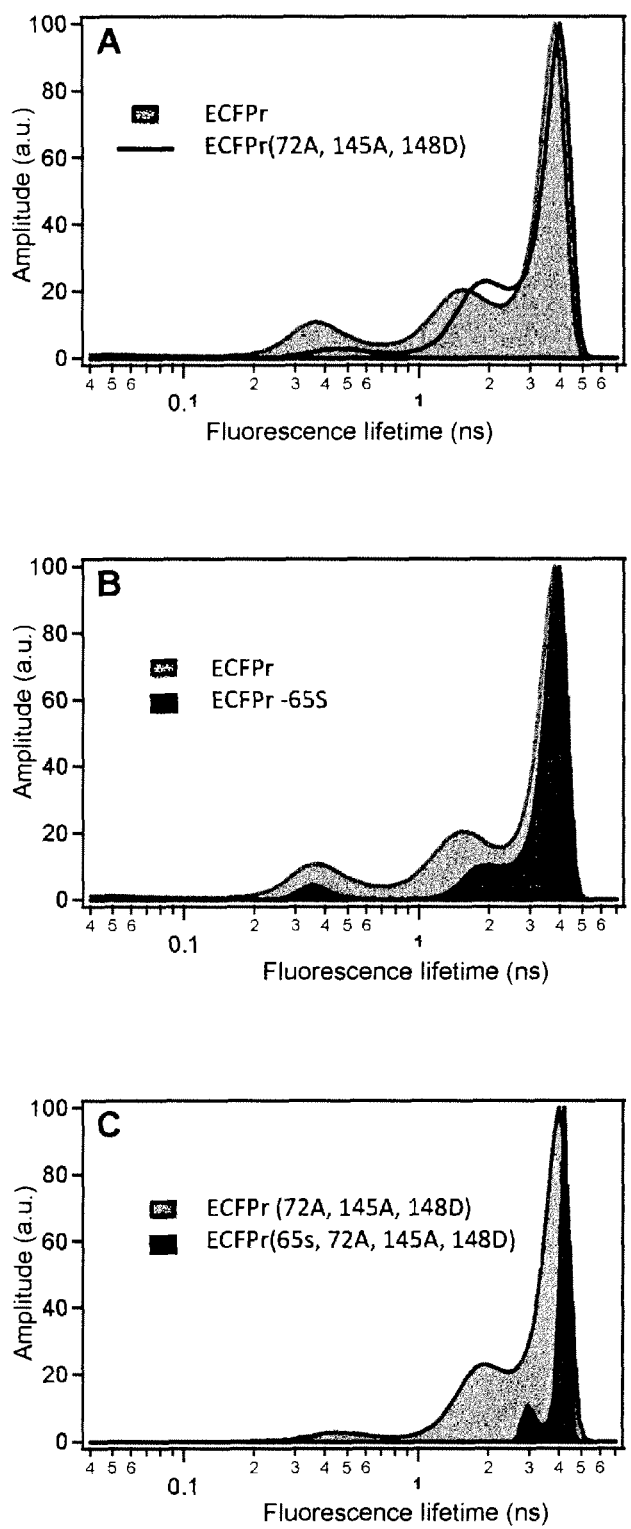

FIG. 23: Fluorescent lifetime distribution of cyan fluorescent proteins, comprising or not the 65S mutation. The distributions were obtained via analysis, by the maximum entropy method, of the fluorescence decay of proteins ECFPr, ECFPr (65S), ECFPr (72A, 145A, 148D) and ECFPr (65S, 72A, 145A, 148D). For each protein, distribution was established from six independent experiments carried out at pH 7.4 and at 20° C.

Figure 24:
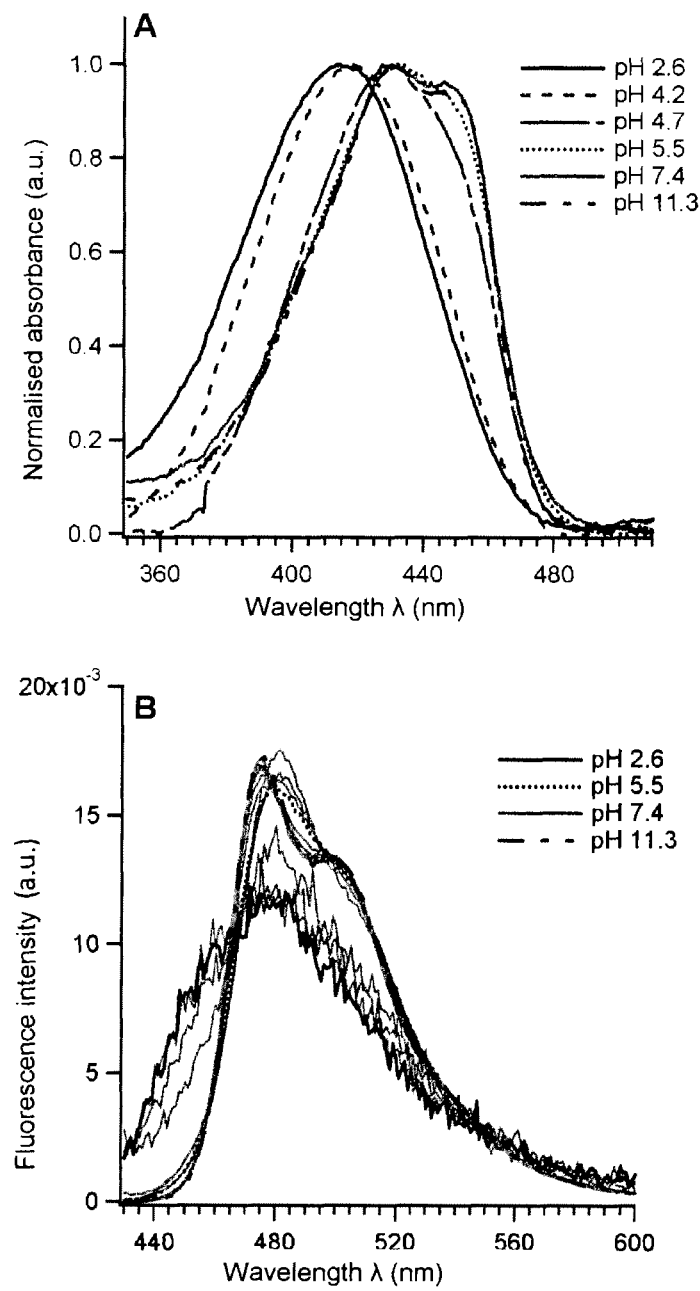

FIG. 24: pH dependence of the ECFPr spectral properties. (A) Absorption spectrum normalised to unit maximum absorbance and (B) Emission spectrum normalised to the same area.

Figure 25:
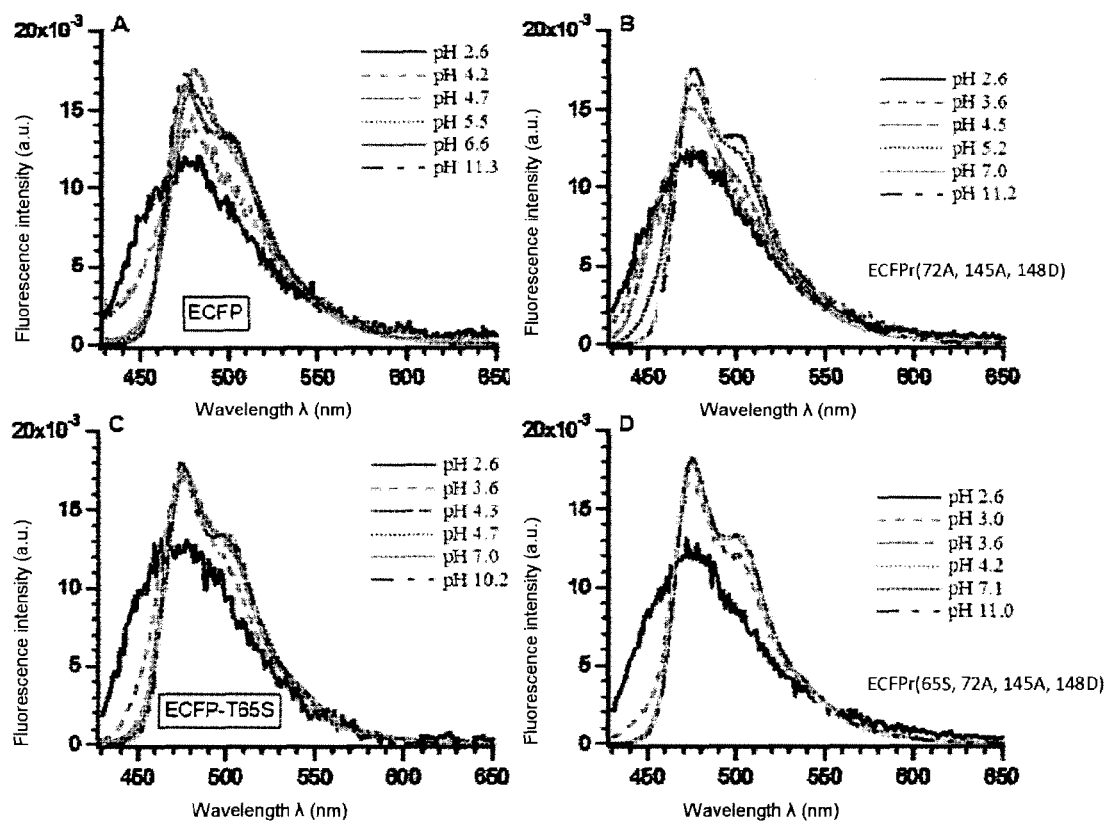

FIG. 25: Emission spectra of the fluorescence of cyan fluorescent proteins, comprising or not the 65S mutation, at acidic neutral and basic pH (A): ECFPr; (B): ECFPr (72A, 145A, 148D); (C): ECFPr (65S); (D) ECFPr (65S, 72A, 145A, 148D).

Figure 26:
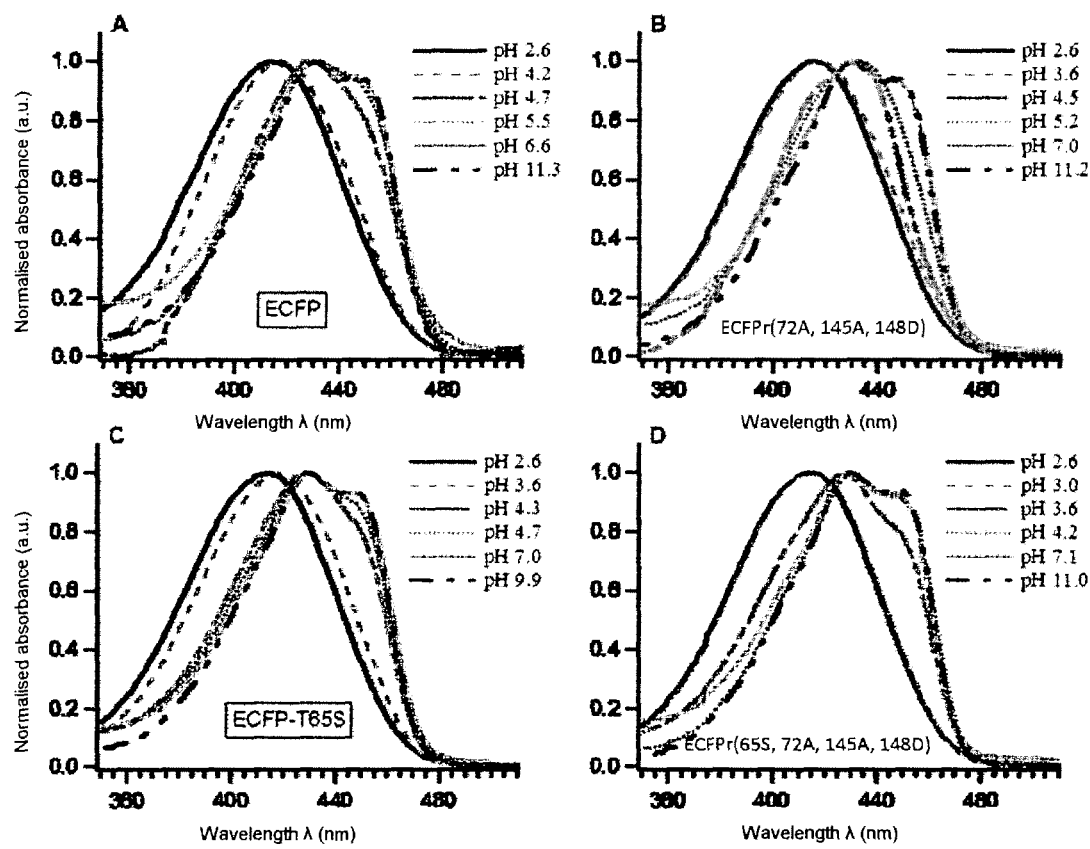

FIG. 26: Absorption spectra of cyan fluorescent proteins comprising or not mutation 65S, at acid, neutral and basic pH. (A): ECFPr; (B): ECFPr (72A, 145A, 148D); (C): ECFPr (65S); (D) ECFPr (65S, 72A, 145A, 148D).

Figure 27:
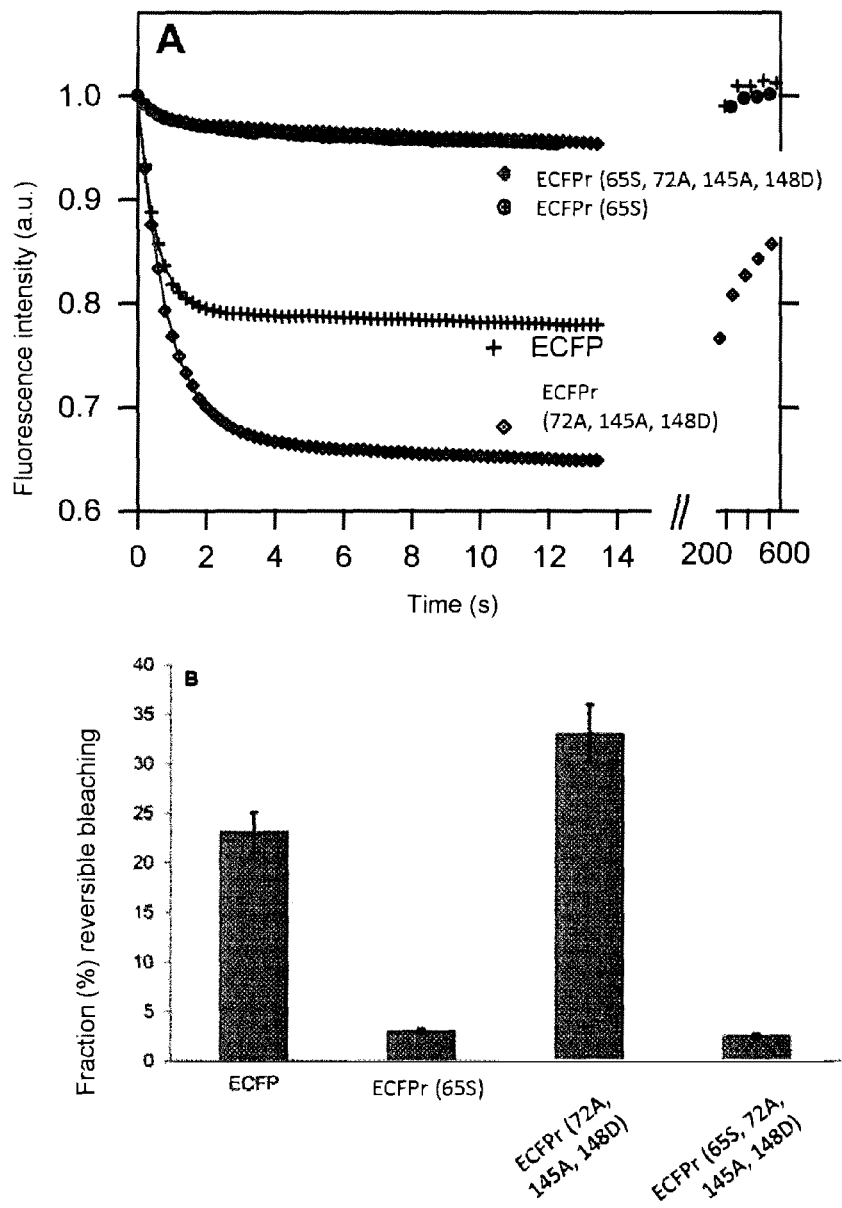

FIG. 27: Reversible photobleaching of cyan fluorescent proteins, comprising or not the 65S mutation. (A) Kinetics of reversible bleaching performed on agarose beads labeled with purified fluorescent proteins. After prior equilibration in the dark, sudden and constant illumination at a power density of 0.2 W/cm² was applied for less than 15 seconds while images were taken every 200 ms. Illumination was then stopped, and, after a minimum of 3 minutes in the dark, a series of fluorescent images was collected to check for reversibility. Continuous lines correspond to the best adjustments on the basis of the model $F^{norm}=y_0+y_1t+y_2\exp(-t/\tau Rev)$. (B) Amplitudes of the reversible photobleaching of cyan fluorescent proteins.

Figure 28:
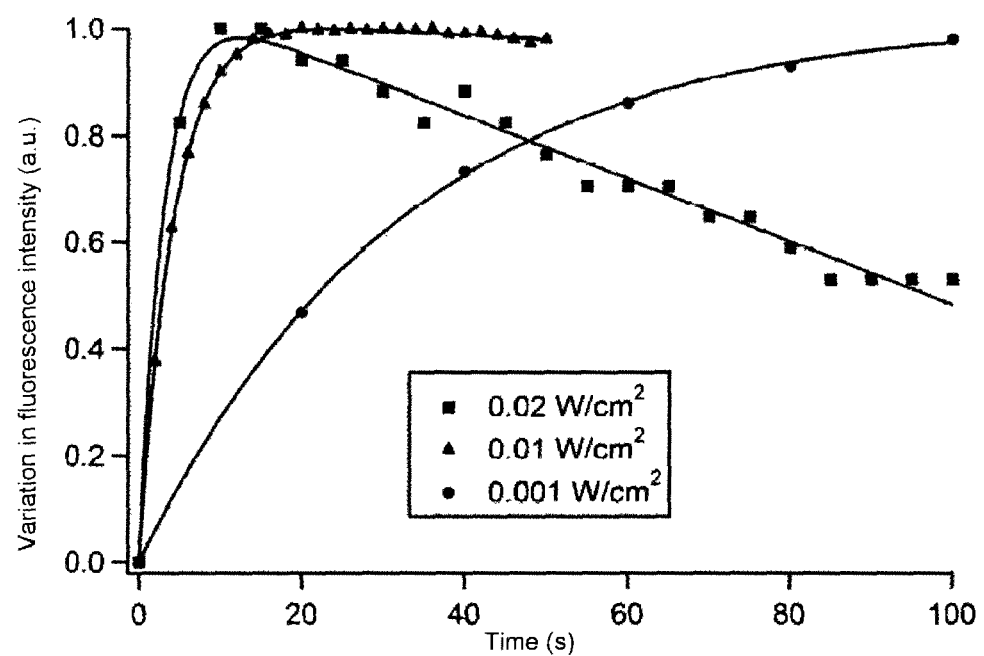

FIG. 28: Photoactivated fluorescence return of cyan fluorescent protein ECFPr after transient photobleaching. The ECFPr protein was initially photobleached using maximum lamp power for less than 1 min. The return of fluorescence intensity after stopping illumination was then evaluated under different lighting regimens: experimental data were normalised (markers) and the best adjustments (continuous lines) were evaluated on the basis of the model $F^{norm}=y_0+y_1t+y_2\exp(-t/\tau_{Back})$.

Figure 29:
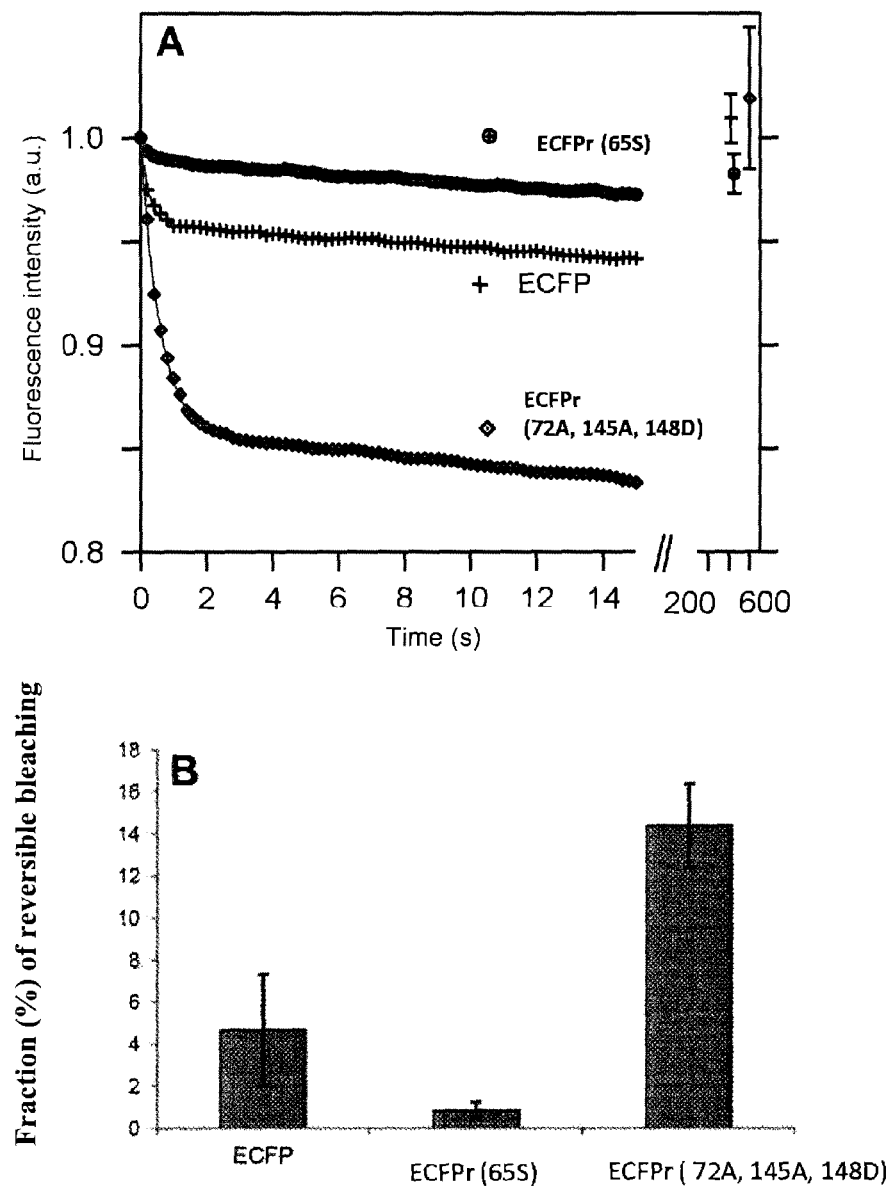

FIG. 29: Reversible photobleaching of cyan fluorescent proteins, comprising or not the 65S mutation, in live MDCK cells. The experimental conditions are identical to those used for the experiments on agarose beads. Each curve represents an average of 4 to 6 decays collected from different individual cells. Continuous lines are the best adjustments on the basis of the model $F^{norm}=y_0+y_1t+y_2\exp(-t/\tau_{Rev})$.

Figure 30:
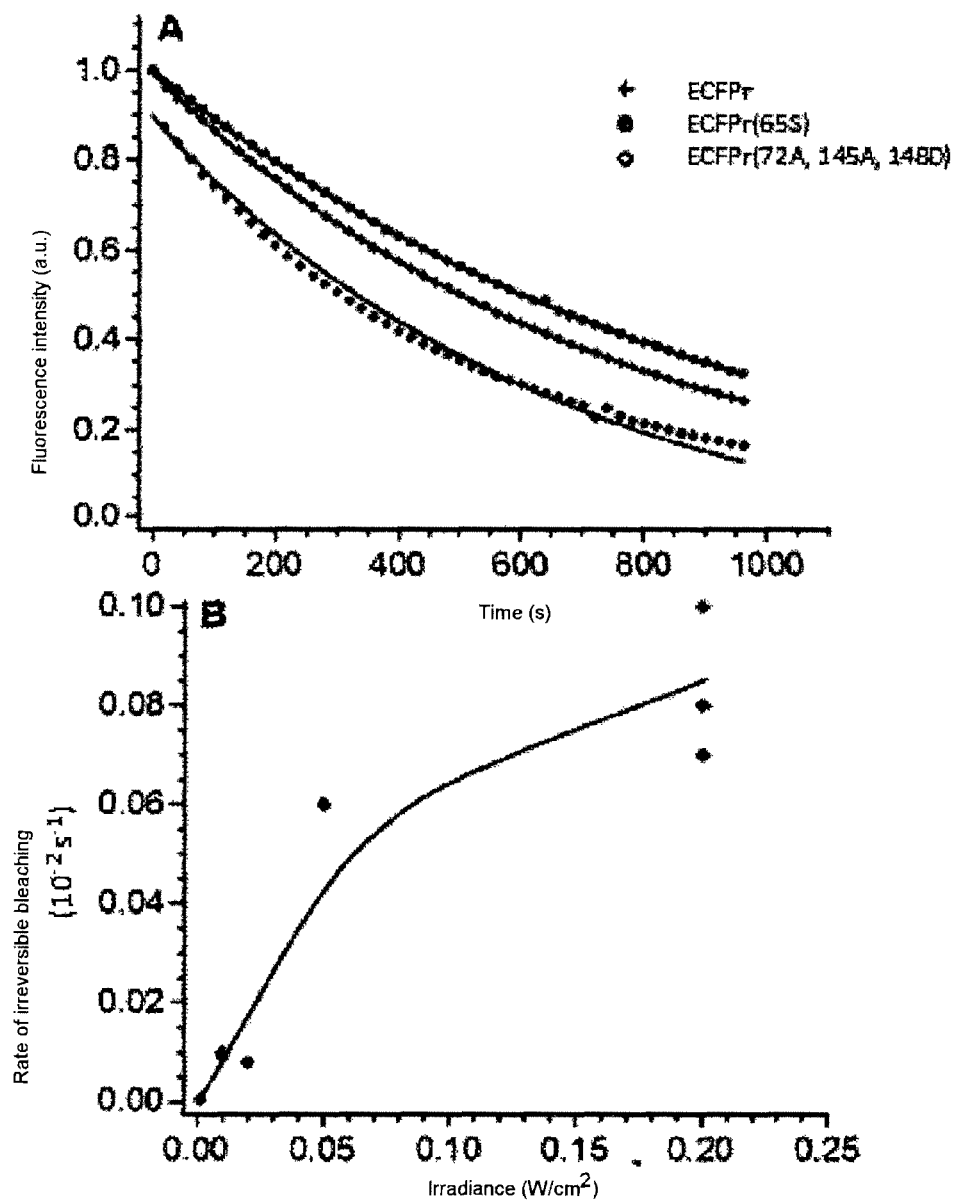

FIG. 30: Irreversible photobleaching of cyan fluorescent proteins, comprising or not the 65S mutation, in live MDCK cells. (A) Constant illumination of a power density of 0.2 W/cm² was applied and images were taken every 20s during this illumination. Each curve is the average of 4 to 6 decays collected from individual cells. Continuous lines are the best adjustments in decay from an exponential model with the time constant $\tau_{Irrev}$. (B) Dependence of the irreversible bleaching rates of ECFPr as a function of power density.

EXAMPLES

A—Materials and Methods

I. Cloning of Cyan Fluorescent Protein

The expression plasmid of ECFP (pHis-ECFP) was constructed from the pECFPN1 vector (Clontech) as follows: the entire ECFP sequence (SEQ ID NO:1) of the pECFPN1 vector was amplified by PCR using the primers 5'-AAGGCGCCGTGAGCAAGGGCGAGGAGCTG-3' (forward primer) of SEQ ID NO:35 sequence and 5'-TTAAGCTTACTTGTACAGCTCGTCCATGCC-3' (reverse primer) of SEQ ID NO:36 sequence.

The PCR product obtained was then digested by HindIII and EheI, ligated in the pPROEX-HTa expression vector (GibcoBRL), then checked by restriction mapping and sequencing. Cloning was carried out such that the sequence MSYYHHHHHHDYDIPTTENLYFQGA (SEQ ID NO:70) (which comprises 6 Histidines and the protease TEV cleavage site) of the pPROEX-HTa vector was inserted in N-Terminal of the ECFP, in order to facilitate purification of the recombinant protein obtained (here SEQ ID NO:4). The fluorescence properties of ECFP are not affected by this sequence.

II. Method Allowing Reduction of the pH Sensitivity of Cyan Fluorescent Protein

II.1. Directed Mutagenesis

Single mutations were introduced into the cyan fluorescent protein by directed mutagenesis according to the <<Quickchange mutagenesis>> protocol from Stratagene. Specific primers were designed for each mutation (see Table 2).

Thus, the 148G monomeric mutation was introduced using the 148Gf (SEQ ID NO:37) and 148Gr (SEQ ID NO:38) primers; the 148S monomeric mutation was introduced using the 148Sf (SEQ ID NO:39) and 148Sr (SEQ ID NO:40) primers; the 65S monomeric mutation was introduced via the 65Sf (SEQ ID NO:49) and 65Sr (SEQ ID NO:50) primers.

Briefly, the reaction conditions employed were as follows: to 39 μL of water were added 1 μL of plasmid vector expressing the cyan fluorescent protein to be mutated (e.g. pHis-ECFP) (10 ng/μL), 1.5 μL of each forward and reverse primer specific to the mutation to be introduced (100 ng/μL), 1 μL of dNTPs (10 mM), 5 μL of reaction buffer 10×, and 1 μL of DNA polymerase Pfu ultra HF (2.5 U/μL). Amplification of the mutated nucleotide sequence was then obtained by subjecting this mixture to the following conditions in a thermocycler: an initial cycle of 2 minutes at 95° C., followed by 18 amplification cycles with each cycle consisting of 30s at 95° C., 30s at 58° C. and 10 minutes at 72° C., ending with a final cycle of 10 minutes at 72° C. Finally the presence of the mutation in the PCR product was checked by digestion with the DpnI enzyme (2.5 U; 1 hour at 37° C.) and DNA sequencing.

with 25 mL of starting culture expressing the vector of interest and previously cultured overnight. Protein production was induced by adding isopropyl-D-thiogalactopyranoside (IPTG, 1 mM) to the transformed cells when the $OD_{600}$ of the cells reached a value of 0.6. After having been cultured for 18 h at 30° C., the induced cells were collected by centrifugation and frozen. The cells were then suspended in 30 mL of lysis buffer (50 mM Tris-HCl, 5 mM of 2-mercaptoethanol, 1 mM PMSF and 0.02 mg/mL of DNase) and sonicated Finally, centrifugation (40,000 rpm, 1h30 at 6° C.) allowed the elimination of cell debris in order to collect only the supernatant.

For the purification of each mutated cyan fluorescent protein, the supernatant was filtered using a 0.22 μm filter and diluted by a factor of 2 in pH 7.5 phosphate buffer (30 mM $NaH_2PO_4$, 700 mM NaCl, 30 mM imidazole). This solution was then deposited in a column containing 5 mL of nitroacetic nickel (Ni-NTA) agarose (15 mL, Sigma) for 1 h. The column was then washed (30 mM $NaH_2PO_4$, 100 mM

TABLE 2 mutations introduced by directed mutagenesis in cyan fluorescent protein in order to assess their respective impact on the pH sensitivity of the protein.

| Mutation | Forward primer (5' to 3') | Reverse primer (5' to 3') |
|---|---|---|
| 148G | 148Gf : SEQ ID NO: 37<br>CAACTACATCAGCGGCAACGTCTATATCACC | 148Gr : SEQ ID NO: 38<br>GGTGATATAGACGTTGCCGCTGATGTAGTTG |
| 148S | 148Sf : SEQ ID NO: 39<br>CAACTACATCAGCTCCAACGTCTATATCACC | 148Sr : SEQ ID NO: 40<br>GGTGATATAGACGTTGGAGCTGATGTAGTTG |
| 148D | 148Df : SEQ ID NO: 41<br>CAACTACATCAGCGACAACGTCTATATCACC | 148Dr : SEQ ID NO: 42<br>GGTGATATAGACGTTGTCGCTGATGTAGTTG |
| 148R | 148Rf : SEQ ID NO: 43<br>CAACTACATCAGCCGCAACGTCTATAT CACC | 148Rr : SEQ ID NO: 44<br>GGTGATATAGACGTTGCGGCTGATGTAGTTG |
| 148N | 148Nf : SEQ ID NO: 45<br>GTACAACTACATCTCCAACAACGTCTATATC | 148Nr : SEQ ID NO: 46<br>GATATAGACGTTGTTGGAGATGTAGTTGTAC |
| 148E | 148Ef : SEQ ID NO: 47<br>CAACTACATCAGCGAGA ACGTCTATATCACC | 148Er : SEQ ID NO: 48<br>GGTGATATAG ACGTTCTCGC TGATGTAGTTG |
| 148A | 148Af : SEQ ID NO: 67<br>CAACTACATCAGCGCCAACGTCTATATCACC | 148Ar : SEQ ID NO: 68<br>GGTGATATAGACGTTGGCGCTGATGTAGTTG |
| 65S | 65Sf : SEQ ID NO: 49<br>CGTGACCACCCTGAGCTGGGGCGTGCAGTGC | 65Sr : SEQ ID NO: 50<br>GCACTGCACGCCCCAGCTCAGGGTGGTCACG |

The following additional mutations were introduced before or after the above-mentioned mutations, according to the same method of directed mutagenesis.

72A, using primers of sequences SEQ ID NO:51 and SEQ ID NO:52;

145A, using primers of sequences SEQ ID NO:53 and SEQ ID NO:54;

206K, using primers of the sequences SEQ ID NO:55 and SEQ ID NO:56.

II.2. Production and Purification of Cyan Fluorescent Protein Mutants

The production and purification of cyan fluorescent protein mutants was carried out according to the protocol described below.

The mutated cyan fluorescent proteins were prepared by transforming TOP10 competent cells (Invitrogen) with the vector of interest (that is to say coding for the mutated fluorescent protein) according to the manufacturer's instructions. A preheated volume of 1.5 L of Luria-Bertani medium (LB) containing 100 μg/mL of ampicillin was inoculated NaCl, 10 mM imidazole, pH 7,5), and the protein of interest eluted (30 mM $NaH_2PO_4$, 100 mM NaCl, 150 mM imidazole, pH 7.5). Before being stored at −20° C., for spectroscopy experiments, the solution of each purified protein was dialysed in a buffer at a concentration of 2 mM and of pH 7.4, consisting of an equimolar concentration of CAPS, 2-(N-morpholino) ethane acid (MES) and Bis-tris propane then concentrated in order to obtain a protein solution with a concentration in the range of 150 μM.

The concentration of the purified proteins was then determined by means of a test using bicinchoninic acid with BSA (bovine serum albumin, 1 mg/mL) as the standard.

The purity of the ECFPr was estimated by means of mass spectrometry, as being superior to 99%. The purity of mutants, purified according to the same protocol, was estimated as being similar (no difference in behaviour was observed in the electrophoresis gels).

II.3. Fluorescence Spectroscopy and Evaluation of pH Sensitivity

All spectroscopic measurements of fluorescence absorption and emission were performed on purified protein solutions of which the concentration did not exceed 10 µM. The protein concentration was generally 10 µM both for stationery spectroscopy measurements (absorption and emission spectra) and for the acquisition in fluorescence emissions decays.

For the pH studies, aliquots of a concentrated solution of the protein of interest were diluted in separate buffers previously adjusted to a suitable pH (accuracy of the measurement: 0.1 pH unit). The nature of the buffer used depends on the pH range studied:

(i) for pH values superior to 5.5 (pH 5.5 to 11), the buffer used is MCBtP 33 mM (equimolar mixture of the usual buffers MES, CAPS and Bis-trispropane) whose pH was adjusted by adding $H_2SO_4$ or NaOH (Aldrich);
(ii) for pH values inferior to 5.5 (pH 2.5 to 5.5), the buffer used is citric acid 50 mM/NaOH, whose pH was also adjusted by adding NaOH.

The addition of concentrated acid directly to the fluorescent protein solution was avoided in order avoid irreversible protein aggregation.

II.3.a. Stationary Fluorescence Spectroscopy

The UV-visible absorption spectra were carried out on a Perkin Elmer Lambda 900 spectrophotometer using quartz cuvettes with a thickness of 1 cm and black side walls (Hellma).

The fluorescence emission spectra of each purified protein were measured on a Fluorolog3 HORIBA Jobin Yvon spectra fluorometer, at a controlled temperature (T=20° C.+/−0.1° C.), using quartz cuvettes with a thickness of 0.3 cm with black walls (Hellma 105-251-QS, Hellma Ltd). The slit width of the excitation and emissions monochromators was set at 1 nm. The spectra were then collected with integration times of 1 s and at increments of 1 nm. The background noise emitted by the buffer was subtracted.

For each purified fluorescent protein, the intensity at 474 nm (maximum of the ECFPr emission spectrum) was measured from the fluorescence emission spectra and its evolution determined as a function of pH. These fluorescent intensities were then corrected for absorbance variations at 420 nm (excitation wavelength) which enables to measure the variation in the quantum yield of fluorescence emission at 474 nm. The half-transition pH, $pH_{1/2}$, was then measured as being the pH value for which the sum of these fluorescence intensities at pH 7.4 and pH 2.5 corresponding to the weakest fluorescence intensity is reduced by half.

II.3.b. Time Resolved Fluorescence Spectroscopy

The fluorescence emission decays were recorded using the time-correlated single photon counting technique (TC-SPC), with as an excitation source a Ti: Sapphire tuneable laser, locked mode (MIRA 900, Coherent, Watford, UK) optically pumped by a laser diode at 532 nm (10W Verdi, Coherent).

The laser repetition rate pulses were reduced from 76 MHz to 3.8 MHz via a pulse picker (crystal SiO2, APE, Berlin, Germany). After the pulse picker, the excitation wavelength of 420 nm was obtained by frequency doubling the 840 nm laser radiation using a BBO crystal doubler. After the frequency doubling, the laser excitation light was sent on the sample placed in a temperature controlled multi-position sample holder. The average laser power at the sample was typically 1 to 1.5 µW (beam waist of about 1-2 mm) The fluorescence decay curves were collected by a rapid electronic device (Ortec, Phillips & Tennelec). The instrumental response function (IRF) obtained by measuring the light scattered by a LUDOX solution (Dupont) typically has a full width at half maximum of 60-70 ps. The excitation was vertically polarised and the sample fluorescence was passed through a polarizer oriented at a magic angle)(54.7° prior to the emission monochromator. The monochromator spectral resolution is 6 nm for most experiments, with the exception of pH studies carried out on ECFPr (H148D), where this resolution was 24 nm. The sample fluorescence and IRF were alternately collected over several tens of cycles in order to obtain sufficient statistics: around $20.10^6$ total counts were collected for each decay curve, at rates of about $10^4$ cts per second.

III. Development of a Biosensor with Reduced pH Sensitivity

III.1. Construction of a pHAKAR Biosensor

The pHAKAR biosensor with reduced pH sensitivity was constructed from the AKAR 2.2 biosensor (Dunn et al., 2006) which consists of Citrine and a cyan fluorescent protein (comprising notably the mutations 26R, 164H and 206K) as the respective energy acceptor and donor, as well as a biosensitive sensor sandwiched between these two proteins, itself consisting of a binding domain to phosphorylated amino acids (FHA) and of a protein kinase A substrate sequence (called PKA). Phosphorylation of threonine in the substrate sequence by PKA leads to recognition of the latter by the FHA binding domain; this leads to a conformational change the biosensor, which results in return with an increase in the FRET signal between the cyan fluorescent protein and Citrine.

The nucleotide sequence coding for the AKAR2.2 biosensor was initially inserted in the pcDNA3 vector (Life Technologies).

The 65S and 148G mutations were then introduced into the pcDNA3-AKAR2.2 plasmid by point mutagenesis via the <<Quickchange>> kit (Stratagene) using primer couples of sequence SEQ ID NO:49 and SEQ ID NO:50, and those of SEQ ID NO:37 and SEQ ID NO:38, respectively. The cyan fluorescent protein of the biosensor thus comprises the 65S and 148G mutations of the invention.

The TagRFP monomeric protein with orange fluorescent emission (Merzlyak et al., 2007) was then cloned in place of Citrine as follows: the nucleotide sequence coding for the mutated cyan fluorescent protein of the biosensor and for the biosensitive sensor were firstly cloned into the pPROEXHTa vector (GibcoBRL) between the HindIII and SacI restriction sites; then the nucleotide sequence for the TagRFP protein was amplified by PCR from the commercial pTagRFP-C vector (Evrogen) using the primers TagRFPf of sequence SEQ ID NO:77 (5'ATTAGAGCTCATGGT-GTCTAAGGGCGAA 3') and TagRFPr of sequence SEQ ID NO:78 (5' ATAATGAATTCTTAATTAAGTTTGTGCC CC 3') and cloned between the SacI and EcoRI sites of the pPROEXHTa vector [ECFPr of sequence SEQ ID NO:82-biosensitive sensor].

The protein kinase A biosensor obtained thereby, named pHAKAR, containing the fluorescent proteins pair ECFPr of sequence SEQ ID NO:82/TagRFP, as well as the biosensitive sensor were then introduced into the HindIII and EcoRI restriction sites of the pCDNA3 plasmid vector. Each cloning was checked by sequencing.

The plasmids coding for the ECFPr (65S, 148G) protein (pECFPN1, Clontech) and for the pHAKAR biosensor (pcDNA3-pHAKAR) were amplified in *E. Coli* and stored at a 1 µg/µL concentration.

III.2. Fluorescence Spectroscopy and Evaluation of the pH Sensitivity of the pHAKAR Biosensor BHK hamster cells were grown in 25 cm² flasks in the presence of DMEM medium supplemented with 10% foetal calf serum (Gibco). During the repicking, the cells were deposited on 25 mm diameter glass coverslips placed at the bottom of a six-well plate, then transfected by lipotransfection at 90% confluency with the pECFPN1 or pcDNA3-pHAKAR plasmid following the manufacturer's protocol (4 µg of plasmid and 10 µL of Lipofectamine2000 per 2 mL of medium; Life Technologies). 24 h after transfection, the coverslips were mounted in an attofluor metal chamber (Life Technologies). The medium used for the measurements contains 140 mM of KCL, 15 mM of MES buffer and 15 mM of Hepes buffer whose pH was adjusted to the desired value (7.4 or 5.9). The intracellular pH was adjusted to the external pH by means of an ionophore, nigericin (final concentration 10 µM). After 5 min of incubation with nigericin at 37° C., the transfected cells were placed at 20° C. on the microscope plate.

The lifetime of the fluorescence emitted by the ECFPr protein comprising at least the 65S and 148G mutations, alone or incorporated into the pHAKAR biosensor, was then observed at different pH values (7.40 and 5.9) using a NIKON TE2000 microscope fitted with a water immersion objective (×60, NA 1,2), a mercury lamp and a fluorescence detection system enabling fluorescent cells to be identified (filters: Omega XF114-2 for ECFPr and TRITC-B-NTE Semrock for TagRFP), as well as an excitation and detection means for measurement of fluorescence lifetimes. The excitation was carried out by means of a pulsed diode at 442 nm (LDH 440 and PDL 800D driver, PicoQuant) which is fibrous and injected into a C1 head scanning type (Nikon) originally used for confocal microscopy. The head scan was guided by the EZ-C1 software and allows spatial control of sample excitation. Under the objective, fluorescence photons were reflected by a retractable dichroic mirror (SWP-500 at 45°, Lambda Research) towards a microchannel plate (Hamamastu) after filtering (Omega 480AF30 filter and two Razor Edge Longpass at 458 nm Semrock). The signals were then collected by a photon counting module PicoHarp300 (Picoquant) which is also synchronised with excitation laser pulses. The data were analysed by the SymPhoTime (Picoquant) software. Each cell was identified as a region of interest, and the histogram of fluorescence lifetimes was calculated from all the pixels in this region. The total number of counts was comprised between 1 and $5.10^6$, and the average lifetime was calculated by SymPhoTime. 5 to 10 cells were measured for each pH condition.

IV. Study of the Influence of the 65S Mutation on Quantum Yield, Fluorescence Decay and Photostability of the ECFP Cyan Fluorescent Protein The ECFPr, ECFPr (65S), ECFPr (72A, 145A and 148D) and ECFPr (65S, 72A, 145A and 148D) proteins were generated, produced and purified according to the protocol described in point II above.

IV.1. Analysis of Spectroscopy Data

Each fluorescence emission decay F(t) with the corresponding device function (IRF) was analysed individually using the maximum entropy method described by Mérola et al. (1989) and Couprie et al. (1994). This analysis assumes that experimental decay F(t) is the product of the following convolution:

$$F(t)=g(t)*I_m(t)$$

where g(t) is the measured IRF, and $I_m(t)$ represents the fluorescence emission law I(t) consecutive to an infinitely brief excitation. The analysis presumes that the fluorescence decay law is composed of a large number of exponential terms. Total decay thus corresponds to the following equation:

$$I_m(t)=I_0\int_0^\infty \alpha(\tau)\exp^{-t/\tau}d\tau$$

where α(t) is the distribution of normalised pre-exponential amplitudes (i.e. $\int\alpha(\tau)d\tau=1$) and $I_o$ is an arbitrary factor incorporating the experimental conditions of measurement. A time shift between F(t) and g(t) was also optimised, and the reduced $\chi^2$ value is found in the range 0.97 to 1.05, with residues and autocorrelation functions distributed in a random manner.

From the distribution of fluorescence lifetime α(t) recovered by this method, a small number of individual components ($\tau_i$) and their corresponding pre-exponential amplitudes ($c_i$) were obtained by integration of each separate peak observed in the distribution. The distribution a(t) was used to calculate the average fluorescence lifetime $<\tau_f>$ which should be proportional to the fluorescence quantum yield (Value B., 2006):

$$<\tau_f>\sum_i c_i \cdot \tau_i = \int_0^\infty \alpha(\tau)\tau\, d\tau$$

The measurement uncertainties on $c_i$, $\tau_i$ and $<\tau_f>$ were determined from the standard deviations from several repeated identical experiments.

IV.2. Synchrotron Radiation Circular Dichroism

Measurements were carried out on the DISCO beamline at the Soleil synchrotron (Gif sur Yvette, France) (Giuliani et al., 2009), using 11 µm calcium fluoride circular cuvettes (Wien et al., 2005) (Hellma).

Protein concentrations were typically 8 mg/L at pH 2.5 and 18 mg/L at pH 7.4. All samples were prepared the day before in their buffer (30 mM CAPS, 30 mM MES and 30 mM of Bis-tris propane at pH 7.4 and 30 mM citric acid at pH 2.5). For each protein, three scans from 170 to 280 nm, at intervals of 1 nm per second, were recorded then averaged. Three consecutive scans of the baseline (using the buffer) were obtained in the same way and averaged. For all proteins, the experiments were recorded at 25° C. The buffer spectrum was subtracted from that of the corresponding samples. The 260-270 nm region was set to zero, and the resulting spectra were calibrated with CSA (D-10-camphosulfonic acid) using the CDtool software (Lees et al., 2004). The average circular dichroism per residue is expressed as $M^{-1}\cdot cm^{-1}$ (Kelly et al., 2005). Determination of secondary structure was performed by DICHROWEB (Whitmore et al., 2004) using the CDSSTR and CONTINLL algorithms as well as the SP175 database (Lees et al., 2006). The two algorithms provide similar results. The results were obtained using the CDSSTR algorithm. The NRMSD adjustment parameter ranges from 0.030 to 0.050 for all proteins.

IV.3. Photobleaching Experiments

IV.3.a. Labelling of Agarose Beads with Cyan Fluorescent Proteins

Nickel loaded agarose beads (Sigma) were labelled with the abovementioned mutated recombinant proteins. 100 µL of sedimented beads, previously washed and equilibrated with phosphate buffer (pH 7.5) were incubated with 1 to 5 µM of purified protein in a total volume of 1 mL for 1 h under gentle stirring in the cold. The beads were then centrifuged for 5 min at 5000 rpm, washed twice and resuspended in PBS. A few microlitres of the bead suspension were deposited on a 25 mm diameter microscope coverslip for photobleaching.

IV.3.b. Expression of Cytosolic Cyan Fluorescent Proteins

MDCK cells cultured on 25 mm diameter coverslips were transiently transfected with eukaryotic expression plasmids coding for the cyan fluorescent protein of interest using Lipofectamine2000, in accordance with the manufacturer's recommendations (Invitrogen). These cells were studied 24 to 48 hours after their transfection.

IV.3.c. Illumination and Imaging Conditions

The fluorescence photobleaching experiments on cyan fluorescent proteins were performed at 20° C.+/−0.5° C. using an epifluorescence microscope equipped with a water immersion objective (×60, NA 1.2; Nikon), an HBO 100W Hg lamp, and using an ECFP dichroic filter to detect fluorescence (Omega XF114-2). The illumination power was adjusted with neutral density filters, the maximum power measured on the sample without any attenuation was approximately 200 µW (FieldMaster 13M41 detector, Coherent), and the radius of the illuminated field was estimated at 185 µm, leading to an average illumination on the sample of about 0.2 W/cm2. Single beads or groups of MDCK cells were placed at the centre of the imaging field and the fluorescence intensity was measured via a cooled CCD camera (ORCA-AG Hamamatsu) and quantified using the NIH ImageJ software. No significant dependence of the photobleaching rates measured as a function of bead size, or of the density of the bead labelling, could be observed.

IV.3.d. Modelling and Analysis of Photobleaching Experiments

Kinetic Model

It is assumed that the cyan fluorescence protein ECFP undergoes a photoactivated reversible reaction between two states, a fluorescent state and a non-fluorescent state, characterized by rate constants $k_{off}$ and $k_{on}$.

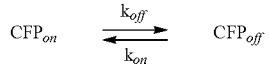

This model neglects the thermal relaxation between these two states, as well as irreversible photobleaching (these taking place on slower time scales, according to the experimental conditions tested here), and assumes identical absorption of the two forms. This results in the following equations:

$$\frac{d[CFP_{on}]}{dt} = -k_{off}[CFP_{on}] + k_{on}[CFP_{off}]$$

$$\frac{d[CFP_{off}]}{dt} = -k_{on}[CFP_{off}] + k_{off}[CFP_{on}],$$

setting x, the relative fraction of the fluorescent state $$x = \frac{[CFP_{on}]}{[CFP_{on}] + [CFP_{off}]}$$

and taking $x_0 = 1$ (no non-fluorescent state at time zero when the system is at thermal equilibrium in the dark), we obtain:

$$x = \left(1 - \frac{k_{on}}{k_{on} + k_{off}}\right) \exp(-(k_{on} + k_{off})t) + \frac{k_{on}}{k_{on} + k_{off}}$$

that is to say, upon sudden illumination, the molar fraction of the fluorescent state decreases monoexponentially with a time constant $\tau_{Rev} = 1/(k_{on} + k_{off})$, and towards a stationary level $y_0 = k_{on}/(k_{on} + k_{off})$.

Adjustment of Reversible Photobleaching Experiments

After normalisation of initial intensity to 1, the transient photobleaching curves were adjusted by the model $$F^{Norm} = y_0 + y_1 t + y_2 \exp(-t/\tau_{Rev})$$

where $y_0$ stands for the stationary fluorescence level, $y_L$ for the irreversible photobleaching rate constant assuming a linear law (the $y_1$ values are generally $\approx -1 \ast 10^{-3} s^{-1}$, in agreement with the irreversible photobleaching rate constants obtained (see FIG. 22), while $y_2$ and $\tau_{Rev}$ are respectively the relative amplitude and time constant of the reversible bleaching.

Fluorescence Recovery after Transient Photobleaching is Accelerated Under Illumination.

After normalisation of the initial intensity to zero and maximum intensity to 1, the fluorescence intensity recovery curves were adjusted according to the same analytical model:

$$F^{Norm} = y_0 + y_1 t + y_2 \exp(-t/\tau_{Back})$$

The relaxation time for fluorescence recovery $\tau_{Back}$ is in excellent agreement with the relaxation times for loss of fluorescence $\tau_{Rev}$ (FIG. 28).

All Rate Constants $k_{on}$ and $k_{off}$ Depend on the Illumination Intensity

The rate constants $k_{on}$ and $k_{off}$ are directly obtained from $y_0$ and $\tau_{Rev}$:

$$k_{on} = \frac{y_0}{\tau_{Rev}}$$

$$k_{off} = \frac{1 - y_0}{\tau_{Rev}}$$

According to the two state kinetic model, assuming a linear dependence of $k_{on}$ and $k_{off}$ towards illumination power, the relaxation time $\tau_{Rev}$ should also linearly depend on the excitation power (or irradiation, in W/cm2) which should not be the case for the fraction of reversible fluorescence loss $(1 - y_0)$, (this is approximately verified for low excitation power: see particularly FIG. 28).

Quantum Yields of Cyan Fluorescent Protein Photoconversion

The quantum yields $\phi_{off}$ and $\phi_{on}$ of the photoconversion reactions of the cyan fluorescent protein ECFPr are given by the following equations:

$$\Phi_{on} = \frac{k_{on}}{k_{exc}}$$

$$\Phi_{off} = \frac{k_{off}}{k_{exc}}$$

where $k_{exc}$ is the excitation rate per molecule, given by the product of the effective absorption section $\sigma_{exc}$ by the photon flux $N_{exc}$ at the excitation wavelength $\lambda_{exc}$:

$$k_{exc} = \sigma_{exc}(cm^2) \times N_{exc}(Photons/s/cm^2)$$

For the ECFPr cyan fluorescent protein, with $I_{exc} = 0.05$ W/cm2, and assuming that $\epsilon_{on} = \epsilon_{off} \approx 30000$ $M^{-1}$ $cm^{-1}$ at $\lambda_{exc} = 440$ nm, we obtain $k_{exc} = 13$ $s^{-1}$, with $k_{off} = 0.18$ $s^{-1}$ and $k_{on} = 0.77$ $s^{-1}$, giving $\phi_{off} = 1.4\%$ and $\phi_{on} = 6.1\%$.

B—Results

I. Comparison of the pH Sensitivity of ECPF, and Mutated Cyan Fluorescent Proteins According to the Invention as a Function of pH The inventors wanted to study the impact of various mutations on the pH sensitivity of ECFP, with the aim of generating cyan fluorescent proteins with reduced pH sensitivity, especially to acidic pH.

They thus introduced various single mutations into ECFP in a recombinant form (ECFPr), and studied their effect on loss of fluorescence intensity and reduced fluorescence lifetime usually observed in this protein when the pH goes from a basic pH to an acidic pH. The results of this study are listed in Table 3 hereafter.

Indeed, as seen in FIG. 1 and Table 3 (below), the ECFPr shows a 50% loss in fluorescence intensity and a 33% decrease in fluorescence lifetime when the pH decreases from 7.4 to 5.5. Spectral modifications are also visible when the pH becomes acidic. These properties strongly limit the reliability of use of ECFPr in quantitative imaging methods in living cells, such as FRET, as these are particularly sensitive to the slightest variation in the fluorescence signal. Actually, the intracellular pH varies depending on the cell compartments in which the ECFPr is solubilised and depending on the experimental conditions tested.

Moreover, the half-transition pH ($pH_{1/2}$) of ECFPr measured by the inventors is 5.6, and its fluorescence lifetime at neutral pH is 2.5 ns. It should be noted that the $pH_{1/2}$ value of ECFPr determined by the inventors differs from that mentioned in the literature, which is around 4.6-4.7. Only objective analysis such as reported herein enables to properly study the real differences in $pH_{1/2}$ between the proteins of the invention and those of the prior art.

In order to resolve the problem of pH sensitivity of the ECFP, the inventors therefore firstly introduced a single mutation at position 148 of ECFPr.

The introduction of the 148D mutation generated a cyan fluorescent protein displaying approximately a 50% loss in fluorescence intensity and a 40% decrease in fluorescence lifetime when the pH goes from 7.4 to 5.5. Its fluorescence lifetime at neutral pH is therefore higher than that of ECFPr because it reaches 3.3 ns whereas that of ECFPr is 2.5 ns (Table 3). This mutation therefore did not allow a reduction in the loss of fluorescence intensity and lifetime at acidic pH by comparison to ECFPr but it significantly improves the lifetime at neutral pH.

The inventors then introduced the 148G mutation into ECFPr, thereby generating the ECFPr (148G) protein. This protein displays only a 18% loss in fluorescence intensity and a 6% decrease in fluorescence lifetime at acidic pH. Its $pH_{1/2}$ is 4.9 and its fluorescence lifetime at neutral pH is 3.37 ns (FIG. 2 and Table 3). The 148G mutation therefore enables to reduce the pH sensitivity of ECFP.

The inventors then tested other mutations at position 148 of ECFP, especially mutations 148E, 148S and 148A.

The ECFPr (148E) protein shows a 27% loss in fluorescence intensity and an 18% decrease in fluorescence lifetime between pH 7.4 and pH 5.5. Its $pH_{1/2}$ is 5.1 and its fluorescence lifetime at neutral pH is 3.15 ns (FIG. 15 and Table 3).

The ECFPr (148S) protein generated in this way shows only a 9% loss in fluorescence intensity and a 15% decrease in fluorescence lifetime between pH 7.4 and pH 5.5. Moreover, the $pH_{1/2}$ of this protein is 4.5 and its fluorescence lifetime at neutral pH is 3.17 ns (FIG. 3 and Table 3). Introduction of the 148S mutation into ECFP therefore allows the obtention of cyan fluorescent proteins with reduced pH sensitivity.

The ECFPr (148A) protein shows only a 7% loss in fluorescence intensity and a 4% decrease in fluorescence lifetime between pH 7.4 and pH 5.5. Moreover, the $pH_{1/2}$ of this protein is 4.5 and its fluorescence lifetime at neutral pH is 3.15 ns (FIG. 4 and Table 3). The introduction of the 148A mutation into ECFP therefore enables to obtain cyan fluorescent proteins with reduced pH sensitivity.

The amino acid at position 148 of ECFP therefore appears to play an important role in the pH sensitivity of this protein.

Subsequently, the inventors focused on the amino acid at position 65 of ECFP. They introduced the 65S mutation by directed mutagenesis, thereby generating the ECFPr (65S) protein. This protein displays advantageous properties since its loss in fluorescence intensity is only 15% and the decrease in fluorescence lifetime is 16% when the pH goes from 7.4 to 5.5. The $pH_{1/2}$ for this protein is 4.5 and its fluorescence lifetime is 3.3 (FIG. 5 and Table 3). The amino acid at position 65 therefore appears also to influence the pH sensitivity properties of ECFP.

Other mutations in addition to those introduced at position 148 or 65 were also evaluated. These were chosen from among mutations 72A, 145A, and 206K.

Thus, the ECFPr (72A, 145A, 148D) cyan fluorescent protein displays spectral modifications, as the ECFPr. Its loss in fluorescence intensity and lifetime are respectively 33% and 32% when the pH goes from 7.4 to 5.5, and is therefore less than the ones of ECFPr. Its half-transition pH ($pH_{1/2}$) is 5.2 (FIG. 7 and Table 3). Nevertheless, the reduction in pH sensitivity conferred by the combination of these mutations is less advantageous than that conferred by the single mutations 148G, 148S, 148A, or 65S.

The inventors therefore replaced mutation 148D by mutation 148G, thereby generating ECFPr (72A, 145A, 148G). This combination of mutations enables to reduce pH sensitivity because the loss in fluorescence intensity and lifetime are only 13% and 3% respectively when the pH goes from 7.4 to 5.5. Moreover the $pH_{1/2}$ of this protein is less than that of ECFPr, and its fluorescence lifetime at neutral pH is increased (Tau=3.13 ns) (FIG. 8 and Table 3).

The combination of the 65S mutation with the 72A and 206K mutations also enables to reduce pH sensitivity (see FIG. 12 and Table 3) compared to ECFP. However, the loss in fluorescence intensity and lifetime observed in this protein (ECFPr (65S, 72A, 206K)) is greater than that observed with the single mutation 65S.

The inventors thus tested double mutations at position 148 and 65 in the presence or not of additional mutations which are in this case mutations 72A and 206K.

The introduction of these double mutations in the presence or not of additional mutations enables to drastically reduce pH sensitivity of the ECFP, and even to abolish it (see Table 3).

Actually, the loss in fluorescence intensity and lifetime are close to 0%, if not completely null, when the pH goes from a basic pH to an acidic pH for the proteins ECFPr (65S, 72A, 145A, 148D), ECFPr (65S, 72A, 148D, 206K) and ECFPr (65S, 72A, 148G, 206K), ECFPr (65S, 148G), ECFPr (65S, 148D), and ECFPr (65S, 148S).

Amongst these proteins, ECFPr displaying only double mutations (65S, 148G) and (65S, 148S) as well as ECFPr (65S, 72A, 148G, 206K) show the best properties of all the mutated cyan fluorescent proteins produced by the inventors: indeed, the loss in fluorescence intensity and lifetime observed are null when the pH goes from 7.4 to 5.5, their respective $pH_{1/2}$ are 3.4; 3.6 and 3.1, and their respective mean fluorescence lifetime at neutral pH is 4.12; 3.86 and 4.06 ns.

ECFPr (65S, 148G) is moreover the best of all the cyan fluorescent proteins produced by the inventors in terms of fluorescence lifetime.

In conclusion, the introduction of a single mutation(s) at position 148 and/or 65 in the ECFP, and more particularly of 148G/A and/or 65S mutations, enables to generate cyan fluorescent proteins whose pH sensitivity is reduced, if not abolished. The use of such proteins in quantitative imaging applications will allow a more reliable quantification of the fluorescence signals they emit.

TABLE 3

Comparison of the pH dependence of different mutants of the cyan fluorescent protein.

| Proteins studied | $<\tau>$ (ns) at pH 7.4 | $pH_{1/2}$ | Percentage of loss in intensity (If) between pH 7.4 to 5.5 | Percentage loss in $<\tau>$ pH 7.4 and 5.5 |
|---|---|---|---|---|
| ECFPr (SEQ ID NO: 4) | 2.5 | 5.6 | 50% | 33% |
| ECFPr (148G) | 3.37 | 4.9 | 18% | 6% |
| ECFPr (148S) | 3.17 | 4.5 | 9% | 15% |
| ECFPr (148A) | 3.15 | 4.5 | 7% | 4% |
| ECFPr (148D) | 3.3 | 5.5 | 50% | 40% |
| ECFPr (148N) | 2.93 | 5.7- | 59%- | — |
| ECFPr (148E) | 3.15 | 5.1- | 27%- | 18% |
| ECFPr (148R) | 2.04 | 5.7 | 45% | — |
| ECFPr (65S) | 3.3 | 4.5 | 15% | 16% |
| ECFPr (72A, 145A, 148D) | 3.06 | 5.2 | 33% | 32% |
| ECFPr (72A, 145A, 148G) | 3.13 | 4.4 | 13% | 3% |
| ECFPr (65S, 72A, 145A, 148D) | 3.95 | 3.6 | 0% | 0% |
| ECFPr (65S, 72A, 148D, 206K) | 4.05 | 3.9 | 0% | 0% |
| ECFPr (65S, 72A, 148G, 206K) | 4.06 | 3.1 | 0% | 0% |
| ECFPr (65S, 72A, 206K) | 3.38 | 4.8 | 23% | 15% |
| ECFPr (65S, 148G) | 4.12 | 3.4 | 0% | 0% |
| ECFPr (65S, 148D) | 4.02 | 4 | 0% | 0% |
| ECFPr (65S, 148E) | 3.86 | 4.1 | 0% | 0% |
| ECFPr (65S, 148S) | 3.86 | 3.6 | 0% | 0% |

($<\tau>$ = mean fluorescence lifetime in nanoseconds (ns); If = fluorescence intensity).

II. Study of the pH Sensitivity of a New Biosensor

At physiological pH (7.4), the inventors found that the average lifetime of fluorescence emitted by the cyan fluorescent protein ECFPr incorporated into the pHAKAR biosensor and whose sequence comprises, among others, the 65S and 148G mutations, is reduced by 16% compared to the ECFPr (65S, 148G) protein expressed on its own (3.32 ns versus 3.96 ns). This drop in fluorescence lifetime is linked to energy transfer between the cyan fluorescent protein and the TagRFP, and not to the presence of the additional mutations 26R, 164H and 206K which are silent mutations from the point of view of photophysical properties of cyan fluorescent protein.

Nevertheless when the intracellular pH is reduced to 5.9, the average lifetime of the fluorescence of the mutated protein ECFPr of the pHAKAR biosensor is altered only very slightly, going from 3.32 ns to 3.23 ns, emphasizing the lack of pH sensitivity of the pHAKAR biosensor.

In view of these results, the pair of fluorescent proteins ECFPr (65S, 148G), which can moreover include additional mutations which do not affect its photophysical properties, and TagRFP therefore seems to constitute a performing FRET pair with reduced pH sensitivity.

III. Study of the Impact of the 65S Mutation on Quantum Yield, Fluorescence Decay and Photosensitivity of Cyan Fluorescent Proteins As discussed above, the introduction of the 65S mutation has the effect of reducing the pH sensitivity of the ECFP cyan fluorescent protein. The inventors have also discovered that the introduction of this mutation also increases the quantum yield, simplifies the kinetics of fluorescence emission and improves the photostability of this protein to photobleaching.

III.1. The 65S Mutation Improves the Homogeneity and Quantum Yield of Cyan Fluorescent Proteins The fluorescence absorption and emission properties of purified proteins ECFPr and ECFPr (72A, 145A, 148D) were compared, at neutral pH and room temperature, with those of proteins including the 65S mutation, that is proteins ECFPr-65S and ECFPr (65S, 72A, 145A, 148D). The inventors found that the absorption and fluorescence spectra of these cyan proteins are actually very similar, and display bimodal absorption and emission spectra typical of indole type chromophores, with two absorption maxima at 430 nm and 445 nm, and two emission maxima at 474 nm and 500 nm (FIG. 21). Taking into account experimental uncertainties, very close absorption coefficients were found for all studied proteins in the range $32000 \pm 4000$ $M^{-1} \cdot cm^{-1}$ at 430 nm (Table in FIG. 22). Despite close spectral similarity, these proteins markedly differ in their quantum yield (FIG. 22), as well as in their fluorescence lifetime distribution as calculated from their fluorescence emission decay (FIG. 23). These lifetime distributions comprise in all cases a major, long fluorescence lifetime, associated with variable amounts of short components (FIG. 22). The ECFPr (72A, 145A, 148D) protein has an enhanced quantum yield as compared to that of the ECFPr protein, but retains a heterogeneous fluorescence emission, its longest lifetime contributing to only 64% of the amplitude of the total amplitude decay (FIGS. 22 and 23).

The 65S single mutation introduced according to the method of the invention considerably improves the performances of the ECFPr and ECFPr (72A, 145A, 148D) proteins. The fluorescence quantum yield of the ECFPr-65S protein is increased by 48% compared to ECFPr, while that of ECFPr (65S, 72A, 145A, 148D) increases by 25% compared to ECFPr (72A, 145A, 148D) (FIG. 22). The 65S mutation also results in a considerable simplification in the fluorescence lifetime distribution (FIG. 23). In the case of the ECFPr (72A, 145A, 148D) protein, the 65S mutation leads to high fluorescence quantum yield and average lifetime, and the fluorescence decay follows a near-monoexponential kinetics with a lifetime amplitude of 83% (FIG. 22).

III.2. The 65S Mutation Suppresses Intermediate Forms of Cyan Fluorescent Proteins Detected During Acid Transition The detailed analysis of the fluorescence absorption and emission spectra of ECFPr and its mutants in the course of acid transition provides a great deal of evidence in favour of the existence of intermediate forms. In particular, in the case of ECFPr, a shift towards red at the maximum of fluorescence emission spectrum is observed following acidification of the medium, and this up to pH 4.7 (FIG. 24). When the pH is further decreased, the emission maximum shifts again back to the blue. This behaviour cannot be accounted for by a simple transition between two states, and provides evidence of the existence of an intermediate state whose fluorescence emission shifted towards the red is clearly distinct from the two neutral and denatured states at highly acidic pH. This <<red>> intermediate disappears when the 65S mutation is introduced into ECFPr (FIG. 25C). Similarly, in the case of protein ECFPr (72A, 145A, 148D), there is an intermediate below $pK_{1/2}$, which is absorbed and emits in the blue (FIGS. 25B and 26B); this isomerized intermediate state (better known under the name cis-trans isomer) becomes undetectable following the introduction of the 65S mutation (FIGS. 25D and 26D). Indeed, the fluorescence absorption and emission spectra of the ECFPr (65S, 72A, 145A, 148D) protein display mixtures of both neutral and acidic form without any intermediate spectral disruption. The loss of fluorescence intensity and of the fine structure of the absorption and emissions spectra, as well as the shifting of spectra, towards blue, take place practically simultaneously within a very narrow pH range.

III.3. The 65S Mutation Reduces the Rate and Amplitude of the Reversible Photobleaching of Cyan Fluorescent Proteins Many natural or genetically modified fluorescent proteins undergo reversible conversion triggered by light between two optically distinct states (also called reversible photoswitching proteins or RSFP). It is moreover recognised that such reversible photoreactions are, to varying degrees, common to the majority of fluorescent proteins, and that this can have major consequences for their use in biological imaging: thus, in standard FRET applications, fluorophores should, as far as possible, be devoid of such photoreactions. Nevertheless, quantitative data on the reversible photoconversion properties of cyan and yellow fluorescent proteins are fairly rare. These reactions are generally easier to observe in purified and immobilised fluorescent proteins, in order to eliminate interference by Brownian diffusion or interference related to movements of living cells expressing these proteins.

The inventors were able to observe that purified protein ECFPr bound to agarose beads undergoes a transient and marked reversible photobleaching under illumination in its chromophore absorption band. Thus, under sudden widefield illumination using the maximum power of a mercury lamp, the fluorescence intensity decreases by 23% following a monoexponential time constant of less than one second (FIGS. 22 and 27). Following this transient response, there is a slower decrease in fluorescence intensity of about 0.1% per second, most likely due to irreversible photobleaching (see below). If the illumination time is kept sufficiently short, and after several minutes in complete dark, the fluorescence intensity reverts back to its initial level (FIG. 27A).

The inventors furthermore observed that the recovery of ECFPr fluorescence after transient bleaching is accelerated by moderate illumination at the same wavelengths (FIG. 28). This shows that the return of ECFPr to its fluorescent state is also activated by light. Consequently, the stationary level of fluorescence achieved after a few seconds of illumination must correspond to a steady state regime, where both "off" (non fluorescent state) and "on" (fluorescent state) photoreactions take place at equivalent rates. A kinetic model involving the two minimum states can be used to describe this system: this model is characterized by two rate constants $k_{off}$ and $k_{on}$, which describe the elementary reactions of reversible bleaching and photoactivated return, respectively. According to this model, the apparent relaxation time $\tau_{rev}$ in the bleaching experiments is the inverse sum of the two rate constants $(k_{on}+k_{off})^{-1}$, while the stationary level of fluorescence intensity reached after a few seconds is given by $k_{on}/(k_{on}+k_{off})$, from which the rate constants $k_{on}$ and $k_{off}$ can be obtained (Table 4). From these two rate constants, we can also estimate the photoconversion quantum yields in both directions: the values obtained, $\phi_{off}=1\%$ and $\phi_{on}=6\%$, show that ECFPr is a highly effective reversible photoswitching protein (RSFP).

Transient bleaching of other cyan fluorescent proteins comprising or not the 65S mutation was also studied according to the same experimental protocol. Upon sudden illumination, all fluorescent proteins undergo a reversible decrease in fluorescence intensity on similar time scales of a few seconds but with very different amplitudes (FIG. 27). Therefore, it is noted that the ECFPr (72A, 145A, 148D) protein shows a marked decrease of 33%. Even more notably the 65S mutation introduced into ECFPr or ECFPr (72A, 145A, 148D) clearly reduces the amplitude of the transient decrease, to less than 3% in both cases (FIG. 27B). Comparing the rate constants $k_{on}$ and $k_{off}$ of each of these proteins (Table 4), it is noted that the proteins comprising the 65S mutation display a reversible bleaching rate $k_{off}$ that is 10 times lower than that of proteins devoid of this mutation, with only moderate changes to the photoactivated return (Table 4). Consequently, the principle effect of the 65S mutation is to considerably slow down the elementary rate of reversible bleaching $k_{off}$, which leads to a reduction in the amplitude of transient bleaching.

Cyan fluorescent protein photoreactions are also observable in MDCK cells expressing these proteins in their cytosol (FIG. 29). However, by using identical wide-field illumination conditions, the amplitudes of the responses seem to be considerably reduced as compared to those obtained in vitro, and the relaxation times are considerably shorter (Table 4), this may originate from the conditions of acquisition. Nevertheless, comparison of the different cyan fluorescent proteins reveals tendencies that are very similar to those observed in vitro, that is that the 65S mutation strongly reduces transient responses (FIG. 29).

TABLE 4

Reversible bleaching parameters of cyan fluorescent protein comprising or not the 65S mutation on agarose beads or in cells.

| | Agarose beads | | | | Living cells | | |
|---|---|---|---|---|---|---|---|
| Proteins studied | % Rev ± 2% | $\tau_{Rev}$ (s) ±0.1 | $k_{off}$ (s$^{-1}$) | $k_{on}$ (s$^{-1}$) | % Rev ± Std Dev | $\tau_{Rev} \pm$ Std Dev (s) | N |
| ECFPr | 23.1 | 0.6 | 0.404 | 1.35 | 5 ± 3 | 0.28 ± 0.04 | 21 |
| ECFPr-65S | 3 | 1.0 | 0.029 | 0.94 | 0.8 ± 0.4 | 0.6 ± 0.3 | 15 |
| ECFPr (72A, 145A, 148D) | 33 | 1.0 | 0.337 | 0.68 | 14 ± 2 | 0.6 ± 0.1 | 21 |
| ECFPr (65S, 72A, 145A, 148D) | 2.5 | 0.8 | 0.033 | 1.30 | — | — | — |

% Rev: percentage of loss of initial fluorescence intensity after sudden illumination of a power density of 0.2 W/cm$^2$;
$\tau_{Rev}$: time constant of initial decay in fluorescence intensity;
$k_{off}$: rate constant for the formation of a non fluorescent state of the protein;
$k_{on}$: rate constant for the formation of a fluorescent state of the protein.

III.4. The 65S Mutation Slows Down Irreversible Photobleaching of Cyan Fluorescent Proteins The irreversible bleaching reactions of the cyan fluorescent proteins, comprising or not the 65S mutation were also studied. To do so, identical but prolonged wide-field illumination conditions were used both on immobilised agarose beads and in the cytosol of cells. All the cyan fluorescent proteins studied display between 85% and 95% irreversible fluorescence loss after 30 min of illumination at maximum power under a mercury lamp. The decay in fluorescence intensity is approximately exponential (FIG. 30), with less than 1% intensity recovery in the dark and no detectable photoactivated recovery, and this up to 10 minutes after stopping illumination. The experiments conducted on immobilised agarose beads and on cells gave fairly similar irreversible bleaching time constants (FIG. 22): thus, in all cases, the single mutation 65S considerably slows down irreversible bleaching of proteins ECFPr and ECFPr (72A, 145A, 148D) (Table 1). The ECFPr (72A, 145A, 148D) protein undergoes a slightly faster bleaching than ECFPr, thereby demonstrating that this protein has a decreased photostability for both reversible and irreversible reactions.

The effect of the 65S mutation is therefore to improve the photo stability of cyan fluorescent proteins in response to irradiation.

CONCLUSION

The inventors were thus able to observe the considerable impact of the 65S mutation on the photophysical properties of cyan fluorescent proteins. This specific mutation allows, in addition to the reduction in pH sensitivity of these proteins, the improvement of their quantum yield, the decrease in the complexity of their fluorescence kinetics, alongside the inhibition of reversible photoreactions and slowing down of irreversible photobleaching.

Thus, the cyan fluorescent proteins comprising the 65S mutation can be used more particularly in imaging studies by Förster resonance energy transfer (FRET) or fluorescence lifetime imaging microscopy (FLIM) in living cells as they allow a more accurate and more sensitive quantitative analysis, and consequently a more reliable analysis, of the fluorescence signals.

BIBLIOGRAPHY

Prasher D. C. et al. (1992). Gene, 111: 229-33.
Day R. N., Davidson M. W. (2009). Chemical society reviews, 38: 2887-2921.
Cubitt A. B., Heim R., Adams S. R., Boyd A. E., Gross L. A., Tsien R. Y. (1995). Trends Biochem Sci., 20(11): 448-55.
Llopis J., McCaffery J. M., Miyawaki A., Farquhar M. G., Tsien R. Y. (1998). Proc Natl Acad Sci USA, 95(12): 6803-8.
Cubitt A. B., Woollenweber L. A., Heim R. (1999). Methods Cell Biol., 58:19-30.
Miyawaki A., Griesbeck 0., Heim R., Tsien, R. Y. (1999). Proc Natl Acad Sci USA, 96(5):2135-40.
Shaner N. C., Patterson G. H., Davidson M. W. (2007). J. Cell. Sci., 120: 4247-4260.
Patterson G. H., Day R. N., Piston D. (2001). J. Cell Sci., 114: 837-838.
Tramier M., Gautier I., Piolot T., Ravalet S., Kemnitz K., Coppey J., Durieux C., Mignotte V., Coppey-Moisan M. (2002). Biophys J., 83(6):3570-7.
Miyawaki A., Tsien R. Y. (2000). Methods Enzymol., 327: 472-499.
Rizzo M. A., Springer G. H., Granada B., Piston D. W. (2004). Nat. Biotechnol., 22(4): 445-449, 2004.
Malo G. D., Pouwels L. J., Wang M T., Weichsel A., Montfort W. R., Rizzo M. A., Piston, D. W., Wachter R. M. (2007). Biochemistry, 46(35): 9865-9873.
Nguyen A. W., Daugerthy P. S. (2005). Nature Biotechnology, 23(3): 355-360.
Shaner N. C., Steinbach P. A., Tsien R. Y. (2005). Nat. Methods, 2: 905-909.
Goedhart J., van Weeren L., Hink M. A., Vischer N. O., Jalink K., Gadella T. W. Jr. (2010). Nat. Methods, 7(2): 137-9.
Sawano A., Miyawaki A. (2000). Nucleic Acids Res., 28(16): E78.
Espagne A., Erard M., Madiona K., Derrien V., Jonasson G., Lévy B., Pasquier H., Melki R., and Mérola F. (2011). Biochemistry, 50(4): 437-9.
Valeur, B. (2006). Molecular Fluorescence Principles and Applications., 3ème éd., Wiley-VCH.
O'Connor, D. V., and Philipps, D. (1984). Time-correlated single photon counting, Academic Press, London.
Needleman S. B., and Wunsch C. D. (1970). J. Mol. Biol., 48: 443-453.
Griesbeck O., Baird G. S., Campbell R. E., Zacharias D. A., Tsien R. Y. (2001). The journal of biological chemistry, 276 (31): 29188-29194.
Nagai T., Ibata K., Park E. S., Kubota M., Mikoshiba K, Miyawaki, A. (2002). Nature Biotechnology, 20: 87-90.
Sambrook et al. (2001). Molecular Cloning: A laboratory Manual, 3ème édition, Cold Spring Harbor Laboratory Press.
Ausubel et al. (2011). Current Protocols in Molecular Biology, John Wiley & Sons.
Merzlyak E. M., Goedhart J., Shcherbo D., Bulina M. E., Shcheglov A. S., Fradkov A. F., Gaintzeva A., Lukyanov K. A., Lukyanov S., Gadella T. W., Chudakov D. M. (2007). Nat Methods; 4(7): 555-7.
Zhang J., Ma Y., Taylor S. S., Tsien R. Y. (2001). Proc Natl Acad Sci USA; 98:14997-15002.
Zhang J., Hupfeld C. J., Taylor S. S., Olefsky J. M., Tsien R. Y. (2005). Nature, 437 (7058): 569-573.
Dunn T. A., Wang C. T., Colicos M. A., Zaccolo M., DiPilato L. M., Zhang J., Tsien R. Y., and Feller M. B. (2006). The Journal of Neuroscience; 26(49):12807-12815.
Morris M. C. (2010). Cell Biochem Biophys., 56:19-37.
Frommer W. B., Davidson M. W., and Campbell R. E. (2009). Chem Soc Rev; 38: 2833-41.
Heyduk (2002). Curr Opin Biotechnol., 13 (4): 292-6
Truong et al. (2001). Curr Opin Struct Biol, 11(5):573-8.
Issad et al. (2003). Diabetes Metab., 29 (2 Pt 1): 111-7.
Boute et al. (2002). Pharmacol Sci., 23 (8):351-4. Trugnan G., Fontanges P., Delautier D., Ait-Slimane T. (2004). Medecine/Science, 20: 1027-34.
Kumar S., Alibhai D., Margineanu A., Laine R., Kennedy G., et al. (2011). Chem Phys Chem., 12: 209-626. Mérola F., Rigler R., Holmgren A., Brochon J. C. (1989). Biochemistry; 28: 3383-3398.
Couprie M. E., Mérola F., Tauc P., Garzella D., Delboulbé A., Hara, T., Billardon, M. (1994). Review of Scientific Instruments; 65: 1485-1495.
Giuliani A., Jamme F., Rouam V., Wien F., Giorgetta J. L., Lagarde B., Chubar 0., Bac S., Yao I., Rey S., Herbeaux C., Marlats J.-L., Zerbib D., Polack F. and Réfrégiers M. (2009). *J Synchrotron Radiat;* 16(6): 835-841.

Wien F., Wallace B. A. (2005). *Appl Spectrosc;* 59: 1109-1113.

Lees J. G., Smith B. R., Wien F., Miles A. J., Wallace B. A. (2004). *Anal Biochem;* 332: 285-289.

Kelly S. M., Jess T. J., Price N. C. (2005). *Biochim Biophys Acta;* 1751: 119-139.

Whitmore L., Wallace B. A. (2004). *Nucleic Acids Res;* 32: W668-673.

Lees J. G., Miles A. J., Wien F., Wallace B. A. (2006). *Bioinformatics;* 22: 1955-1962.

---

The invention claimed is:

1. A method for generating cyan fluorescent proteins displaying reduced pH sensitivity, consisting of:
   a) introducing a single or double mutation into a protein sequence comprising SEQ ID NO:2, wherein:
      said mutation is introduced at position 148 or at positions 65 and 148 of SEQ ID NO:2, and
      the amino acid at position 65 is substituted by a serine and/or the amino acid at position 148 is substituted by a glycine, an alanine, or a serine; and
   b) optionally, introducing into SEQ ID NO:2 a mutation selected from the group consisting of 9G, 11I, 19E, 26R, 68L, 87V, 164H, 167A, 172T, 175G, 194I, 206K, and combinations thereof, wherein said step b) may occur before or after step a).

2. A cyan fluorescent protein obtained by the method according to claim 1.

3. A biosensor, comprising the cyan fluorescent protein according to claim 2.

4. The biosensor according to claim 3, wherein the sequence of said cyan fluorescent protein comprises at least the 65S and 148G mutations.

5. The biosensor according to claim 3, further comprising a fluorescent protein whose absorption spectrum partially overlaps with the emission spectrum of the protein according to claim 2.

6. The biosensor according to claim 5, wherein said fluorescent protein whose absorbtion spectrum partially overlaps with the emission spectrum of the protein according to claim 2 is selected among the fluorescent proteins YFP, Topaz, EYFP, YPET, SYFP2, Citrine, Venus, cp-Venus, Kusabira Orange, Kusabira Orange2, mOrange, mOrange2, dTomato, dTomato-Tandem, DsRed and its variants, TagRFP, TagRFP-T, mRuby, mApple, mStrawberry, AsRed2, mRFP1, JRed, mCherry, eqFP611, HcRed1, mRasberry, tDRFP639, mKate, mKate2, Katushka, tdKatushka, HcRed-Tandem, mPlum and AQ143.

7. The biosensor according to claim 6, wherein said fluorescent protein whose absorption spectrum partially overlaps with the emission spectrum of the protein according to claim 2 is TagRFP.

8. The biosensor according to claim 3, wherein said cyan fluorescent protein is directly linked to the biosensor.

9. The biosensor according to claim 3, wherein said cyan fluorescent protein is indirectly linked to the biosensor.

10. The method according to claim 1, wherein a mutation selected from the group consisting of 9G, 11I, 19E, 26R, 68L, 87V, 164H, 167A, 172T, 175G, 194I, 206K, and combinations thereof, is introduced into SEQ ID NO:2.

11. The biosensor according to claim 6, wherein said fluorescent protein whose absorption spectrum partially overlaps with the emission spectrum of the protein according to claim 2 is DsRed2, DsRed-Express (T1), DsRed-Express2, DsRed-Max or DsRed-Monomer.

* * * * *

SEQUENCE LISTING

```
<160> NUMBER OF SEQ ID NOS: 82

<210> SEQ ID NO 1
<211> LENGTH: 714
<212> TYPE: DNA
<213> ORGANISM: artificial
<220> FEATURE:
<223> OTHER INFORMATION: ECFP nucleotide sequence

<400> SEQUENCE: 1
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgacctgggg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacatcag ccacaacgtc tatatcaccg ccgacaagca gaagaacggc     480
atcaaggcca acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga agcgcgatca catggtcctg     660
ctggagttcg tgaccgccgc cgggatcact ctcggcatgg acgagctgta caag           714

<210> SEQ ID NO 2
<211> LENGTH: 238
<212> TYPE: PRT
<213> ORGANISM: artificial
<220> FEATURE:
<223> OTHER INFORMATION: ECFP amino acid sequence

<400> SEQUENCE: 2

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
```

```
                  130                 135                 140
Tyr Ile Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 3
<211> LENGTH: 789
<212> TYPE: DNA
<213> ORGANISM: artificial
<220> FEATURE:
<223> OTHER INFORMATION: recombinant ECFP (EFCPr) nucleotide sequence

<400> SEQUENCE: 3
atgtcgtact accatcacca tcaccatcac gattacgata tcccaacgac cgaaaacctg      60
tattttcagg gcgccgtgag caagggcgag gagctgttca ccggggtggt gcccatcctg     120
gtcgagctgg acggcgacgt aaacggccac aagttcagcg tgtccggcga gggcgagggc     180
gatgccacct acggcaagct gaccctgaag ttcatctgca ccaccggcaa gctgcccgtg     240
ccctggccca ccctcgtgac caccctgacc tggggcgtgc agtgcttcag ccgctacccc     300
gaccacatga agcagcacga cttcttcaag tccgccatgc ccgaaggcta cgtccaggag     360
cgcaccatct tcttcaagga cgacggcaac tacaagaccc gcgccgaggt gaagttcgag     420
ggcgacaccc tggtgaaccg catcgagctg aagggcatcg acttcaagga ggacggcaac     480
atcctggggc acaagctgga gtacaactac atcagccaca cgtctatat caccgccgac     540 aagcagaaga acggcatcaa ggccaacttc aagatccgcc acaacatcga ggacggcagc     600
gtgcagctcg ccgaccacta ccagcagaac ccccccatcg gcgacggccc cgtgctgctg     660
cccgacaacc actacctgag cacccagtcc gccctgagca agacccccaa cgagaagcgc     720
gatcacatgg tcctgctgga gttcgtgacc gccgccggga tcactctcgg catggacgag     780
ctgtacaag                                                             789

<210> SEQ ID NO 4
<211> LENGTH: 263
<212> TYPE: PRT
<213> ORGANISM: artificial
<220> FEATURE:
<223> OTHER INFORMATION: recombinant ECFP (ECFPr) amino acid sequence

<400> SEQUENCE: 4

Met Ser Tyr Tyr His His His His His His Asp Tyr Asp Ile Pro Thr
1               5                   10                  15

Thr Glu Asn Leu Tyr Phe Gln Gly Ala Val Ser Lys Gly Glu Glu Leu
            20                  25                  30

Phe Thr Gly Val Val Pro Ile Leu Val Glu Leu Asp Gly Asp Val Asn
        35                  40                  45

Gly His Lys Phe Ser Val Ser Gly Glu Gly Glu Gly Asp Ala Thr Tyr
    50                  55                  60
```

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Trp Gly Val Gln Cys Phe
            85                  90                  95

Ser Arg Tyr Pro Asp His Met Lys Gln His Asp Phe Phe Lys Ser Ala
            100                 105                 110

Met Pro Glu Gly Tyr Val Gln Glu Arg Thr Ile Phe Phe Lys Asp Asp
            115                 120                 125

Gly Asn Tyr Lys Thr Arg Ala Glu Val Lys Phe Glu Gly Asp Thr Leu
            130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Ile Ser His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Asp Gly Ser Val Gln Leu Ala Asp His Tyr Gln
            195                 200                 205

Gln Asn Thr Pro Ile Gly Asp Gly Pro Val Leu Leu Pro Asp Asn His
            210                 215                 220

Tyr Leu Ser Thr Gln Ser Ala Leu Ser Lys Asp Pro Asn Glu Lys Arg
225                 230                 235                 240

Asp His Met Val Leu Leu Glu Phe Val Thr Ala Ala Gly Ile Thr Leu
                245                 250                 255

Gly Met Asp Glu Leu Tyr Lys
            260

<210> SEQ ID NO 5
<211> LENGTH: 714
<212> TYPE: DNA
<213> ORGANISM: artificial
<220> FEATURE:
<223> OTHER INFORMATION: ECFP (148G) nucleotide sequence

<400> SEQUENCE: 5

```
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgacctgggg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacatcag cggcaacgtc tatatcaccg ccgacaagca gaagaacggc     480
atcaaggcca acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga agcgcgatca catggtcctg     660
ctggagttcg tgaccgccgc cgggatcact ctcggcatgg acgagctgta caag           714
```

<210> SEQ ID NO 6
<211> LENGTH: 238
<212> TYPE: PRT
<213> ORGANISM: artificial

<220> FEATURE:
<223> OTHER INFORMATION: ECFP (148G) amino acid sequence

<400> SEQUENCE: 6

| | | | | | | | | | | | | | | |
|---|---|---|---|---|---|---|---|---|---|---|---|---|---|---|
| Val | Ser | Lys | Gly | Glu | Glu | Leu | Phe | Thr | Gly | Val | Val | Pro | Ile | Leu | Val |
| 1 | | | | 5 | | | | | 10 | | | | | 15 | |
| Glu | Leu | Asp | Gly | Asp | Val | Asn | Gly | His | Lys | Phe | Ser | Val | Ser | Gly | Glu |
| | | | 20 | | | | | 25 | | | | | 30 | | |
| Gly | Glu | Gly | Asp | Ala | Thr | Tyr | Gly | Lys | Leu | Thr | Leu | Lys | Phe | Ile | Cys |
| | | 35 | | | | | 40 | | | | | 45 | | | |
| Thr | Thr | Gly | Lys | Leu | Pro | Val | Pro | Trp | Pro | Thr | Leu | Val | Thr | Thr | Leu |
| | 50 | | | | | 55 | | | | | 60 | | | | |
| Thr | Trp | Gly | Val | Gln | Cys | Phe | Ser | Arg | Tyr | Pro | Asp | His | Met | Lys | Gln |
| 65 | | | | | 70 | | | | | 75 | | | | | 80 |
| His | Asp | Phe | Phe | Lys | Ser | Ala | Met | Pro | Glu | Gly | Tyr | Val | Gln | Glu | Arg |
| | | | | 85 | | | | | 90 | | | | | 95 | |
| Thr | Ile | Phe | Phe | Lys | Asp | Asp | Gly | Asn | Tyr | Lys | Thr | Arg | Ala | Glu | Val |
| | | | 100 | | | | | 105 | | | | | 110 | | |
| Lys | Phe | Glu | Gly | Asp | Thr | Leu | Val | Asn | Arg | Ile | Glu | Leu | Lys | Gly | Ile |
| | | 115 | | | | | 120 | | | | | 125 | | | |
| Asp | Phe | Lys | Glu | Asp | Gly | Asn | Ile | Leu | Gly | His | Lys | Leu | Glu | Tyr | Asn |
| | 130 | | | | | 135 | | | | | 140 | | | | |
| Tyr | Ile | Ser | Gly | Asn | Val | Tyr | Ile | Thr | Ala | Asp | Lys | Gln | Lys | Asn | Gly |
| 145 | | | | | 150 | | | | | 155 | | | | | 160 |
| Ile | Lys | Ala | Asn | Phe | Lys | Ile | Arg | His | Asn | Ile | Glu | Asp | Gly | Ser | Val |
| | | | | 165 | | | | | 170 | | | | | 175 | |
| Gln | Leu | Ala | Asp | His | Tyr | Gln | Gln | Asn | Thr | Pro | Ile | Gly | Asp | Gly | Pro |
| | | | 180 | | | | | 185 | | | | | 190 | | |
| Val | Leu | Leu | Pro | Asp | Asn | His | Tyr | Leu | Ser | Thr | Gln | Ser | Ala | Leu | Ser |
| | | 195 | | | | | 200 | | | | | 205 | | | |
| Lys | Asp | Pro | Asn | Glu | Lys | Arg | Asp | His | Met | Val | Leu | Leu | Glu | Phe | Val |
| | 210 | | | | | 215 | | | | | 220 | | | | |
| Thr | Ala | Ala | Gly | Ile | Thr | Leu | Gly | Met | Asp | Glu | Leu | Tyr | Lys | | |
| 225 | | | | | 230 | | | | | 235 | | | | | |

<210> SEQ ID NO 7
<211> LENGTH: 714
<212> TYPE: DNA
<213> ORGANISM: artificial
<220> FEATURE:
<223> OTHER INFORMATION: ECFP (148S) nucleotide sequence

<400> SEQUENCE: 7

```
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacctgggg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga cacccttggtg  360
aaccgcatcg agctgaaggg catcgacttc aaggaggacg gcaacatcct ggggcacaag   420
ctggagtaca actacatcag ctccaacgtc tatatcaccg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
```

```
ctgagcaccc agtccgccct gagcaaagac cccaacgaga agcgcgatca catggtcctg      660
ctggagttcg tgaccgccgc cgggatcact ctcggcatgg acgagctgta caag            714
```

<210> SEQ ID NO 8
<211> LENGTH: 238
<212> TYPE: PRT
<213> ORGANISM: artificial
<220> FEATURE:
<223> OTHER INFORMATION: ECFP (148S) amino acid sequence

<400> SEQUENCE: 8

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser Ser Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 9
<211> LENGTH: 714
<212> TYPE: DNA
<213> ORGANISM: artificial
<220> FEATURE:
<223> OTHER INFORMATION: ECFP (65S) nucleotide sequence

<400> SEQUENCE: 9

```
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgagctgggg cgtgcagtgc ttcagccgct accccgacca catgaagcag     240
cacgacttct tcaagtccgc catgcccgaa ggctacgtcc aggagcgcac catcttcttc     300
```

```
aaggacgacg gcaactacaa gacccgcgcc gaggtgaagt tcgagggcga caccctggtg    360
aaccgcatcg agctgaaggg catcgacttc aaggaggacg gcaacatcct ggggcacaag    420
ctggagtaca actacatcag ccacaacgtc tatatcaccg ccgacaagca gaagaacggc    480
atcaaggcca acttcaagat ccgccacaac atcgaggacg gcagcgtgca gctcgccgac    540
cactaccagc agaacacccc catcggcgac ggccccgtgc tgctgcccga caaccactac    600
ctgagcaccc agtccgccct gagcaaagac cccaacgaga gcgcgatca catggtcctg    660 ctggagttcg tgaccgccgc cgggatcact ctcggcatgg acgagctgta caag          714
```

<210> SEQ ID NO 10
<211> LENGTH: 238
<212> TYPE: PRT
<213> ORGANISM: artificial
<220> FEATURE:
<223> OTHER INFORMATION: ECFP (65S) amino acid sequence

<400> SEQUENCE: 10

```
Val Ser Lys Gly Glu Glu Leu Phe Thr Gly Val Val Pro Ile Leu Val
1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 11
<211> LENGTH: 714
<212> TYPE: DNA
<213> ORGANISM: artificial
<220> FEATURE:
<223> OTHER INFORMATION: ECFP (65S, 148G) nucleotide sequence

<400> SEQUENCE: 11

```
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg cccacccctc   180
gtgaccaccc tgagctgggg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacatcag cggcaacgtc tatatcaccg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca tggtcctg     660
ctggagttcg tgaccgccgc cgggatcact ctcggcatgg acgagctgta caag          714
```

<210> SEQ ID NO 12
<211> LENGTH: 238
<212> TYPE: PRT
<213> ORGANISM: artificial
<220> FEATURE:
<223> OTHER INFORMATION: ECFP (65S, 148G) amino acid sequence

<400> SEQUENCE: 12

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser Gly Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 13
<211> LENGTH: 714
<212> TYPE: DNA
<213> ORGANISM: artificial
<220> FEATURE:
<223> OTHER INFORMATION: ECFP (65S, 148S) nucleotide sequence

<400> SEQUENCE: 13

```
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg cccaccctc    180
gtgaccaccc tgagctgggg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacatcag ctccaacgtc tatatcaccg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca  catggtcctg   660
ctggagttcg tgaccgccgc cgggatcact ctcggcatgg acgagctgta caag          714
```

<210> SEQ ID NO 14
<211> LENGTH: 238
<212> TYPE: PRT
<213> ORGANISM: artificial
<220> FEATURE:
<223> OTHER INFORMATION: ECFP (65S, 148S) amino acid sequence

<400> SEQUENCE: 14

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser Ser Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
```

```
                    180                 185                 190
Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
        210                 215                 220

Thr Ala Ala Gly Ile Thr Leu Gly Met Asp Glu Leu Tyr Lys
225                 230                 235

<210> SEQ ID NO 15
<211> LENGTH: 714
<212> TYPE: DNA
<213> ORGANISM: artificial
<220> FEATURE:
<223> OTHER INFORMATION: ECFP (72A, 145A, 148D) nucleotide sequence

<400> SEQUENCE: 15
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg cccacccctc     180
gtgaccaccc tgacctgggg cgtgcagtgc ttcgcccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga cacccttggtg     360 aaccgcatcg agctgaaggg catcgacttc aaggaggacg gcaacatcct ggggcacaag     420
ctggagtaca cagccatcag cgacaacgtc tatatcaccg ccgacaagca gaagaacggc     480
atcaaggcca acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga agcgcgatca catggtcctg     660
ctggagttcg tgaccgccgc cgggatcact ctcggcatgg acgagctgta caag           714

<210> SEQ ID NO 16
<211> LENGTH: 238
<212> TYPE: PRT
<213> ORGANISM: artificial
<220> FEATURE:
<223> OTHER INFORMATION: ECFP (72A, 145A, 148D) amino acid sequence

<400> SEQUENCE: 16

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125
```

```
Asp Phe Lys Glu Asp Gly Asn Ile Leu Gly His Lys Leu Glu Tyr Asn
    130                 135                 140

Ala Ile Ser Asp Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
                195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 17
<211> LENGTH: 714
<212> TYPE: DNA
<213> ORGANISM: artificial
<220> FEATURE:
<223> OTHER INFORMATION: ECFP (72A, 145A, 148G) nucleotide sequence

<400> SEQUENCE: 17

```
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacctgggg cgtgcagtgc ttcgcccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca acgccatcag cggcaacgtc tatatcaccg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca catggtcctg   660
ctggagttcg tgaccgccgc cgggatcact ctcggcatgg acgagctgta caag          714
```

<210> SEQ ID NO 18
<211> LENGTH: 238
<212> TYPE: PRT
<213> ORGANISM: artificial
<220> FEATURE:
<223> OTHER INFORMATION: ECFP (72A, 145A, 148G) amino acid sequence

<400> SEQUENCE: 18

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ala Arg Tyr Pro Asp His Met Lys Gln
65                  70                  75                  80
```

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Ala Ile Ser Gly Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 19
<211> LENGTH: 714
<212> TYPE: DNA
<213> ORGANISM: artificial
<220> FEATURE:
<223> OTHER INFORMATION: ECFP (72A, 145A, 148S) nucleotide sequence

<400> SEQUENCE: 19
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgacctgggg cgtgcagtgc ttcgcccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca acgccatcag ctccaacgtc tatatcaccg ccgacaagca gaagaacggc     480
atcaaggcca acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg     660 ctggagttcg tgaccgccgc cgggatcact ctcggcatgg acgagctgta caag           714

<210> SEQ ID NO 20
<211> LENGTH: 238
<212> TYPE: PRT
<213> ORGANISM: artificial
<220> FEATURE:
<223> OTHER INFORMATION: ECFP (72A, 145A, 148S) amino acid sequence

<400> SEQUENCE: 20

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu

```
                  20                  25                  30
Gly Glu Gly Asp Ala Thr Tyr Gly Lys Leu Thr Leu Lys Phe Ile Cys
                35                  40                  45
Thr Thr Gly Lys Leu Pro Val Pro Trp Pro Thr Leu Val Thr Thr Leu
         50                  55                  60
Thr Trp Gly Val Gln Cys Phe Ala Arg Tyr Pro Asp His Met Lys Gln
 65                  70                  75                  80
His Asp Phe Phe Lys Ser Ala Met Pro Glu Gly Tyr Val Gln Glu Arg
                 85                  90                  95
Thr Ile Phe Phe Lys Asp Asp Gly Asn Tyr Lys Thr Arg Ala Glu Val
                100                 105                 110
Lys Phe Glu Gly Asp Thr Leu Val Asn Arg Ile Glu Leu Lys Gly Ile
            115                 120                 125
Asp Phe Lys Glu Asp Gly Asn Ile Leu Gly His Lys Leu Glu Tyr Asn
        130                 135                 140
Ala Ile Ser Ser Asn Val Tyr Ile Thr Ala Asp Lys Gln Lys Asn Gly
145                 150                 155                 160
Ile Lys Ala Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Val Leu Leu Glu Phe Val
    210                 215                 220
Thr Ala Ala Gly Ile Thr Leu Gly Met Asp Glu Leu Tyr Lys
225                 230                 235
```

```
<210> SEQ ID NO 21
<211> LENGTH: 714
<212> TYPE: DNA
<213> ORGANISM: artificial
<220> FEATURE:
<223> OTHER INFORMATION: ECFP (65S, 72A, 145A, 148D) nucleotide sequence

<400> SEQUENCE: 21
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgagctgggg cgtgcagtgc ttcgcccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca acgccatcag cagcaacgtc tatatcaccg ccgacaagca gaagaacggc     480
atcaaggcca acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg     660
ctggagttcg tgaccgccgc cgggatcact ctcggcatgg acgagctgta caag           714

<210> SEQ ID NO 22
<211> LENGTH: 238
<212> TYPE: PRT
```

```
<213> ORGANISM: artificial
<220> FEATURE:
<223> OTHER INFORMATION: ECFP (65S, 72A, 145A, 148D) amino acid sequence

<400> SEQUENCE: 22
```

| | | | | | | | | | | | | | | |
|---|---|---|---|---|---|---|---|---|---|---|---|---|---|---|
| Val | Ser | Lys | Gly | Glu | Glu | Leu | Phe | Thr | Gly | Val | Val | Pro | Ile | Leu | Val |
| 1 | | | | 5 | | | | | 10 | | | | | 15 |
| Glu | Leu | Asp | Gly | Asp | Val | Asn | Gly | His | Lys | Phe | Ser | Val | Ser | Gly | Glu |
| | | | 20 | | | | | 25 | | | | | 30 | |
| Gly | Glu | Gly | Asp | Ala | Thr | Tyr | Gly | Lys | Leu | Thr | Leu | Lys | Phe | Ile | Cys |
| | | 35 | | | | | 40 | | | | | 45 | | |
| Thr | Thr | Gly | Lys | Leu | Pro | Val | Pro | Trp | Pro | Thr | Leu | Val | Thr | Thr | Leu |
| | 50 | | | | | 55 | | | | | 60 | | | | |
| Ser | Trp | Gly | Val | Gln | Cys | Phe | Ala | Arg | Tyr | Pro | Asp | His | Met | Lys | Gln |
| 65 | | | | | 70 | | | | | 75 | | | | | 80 |
| His | Asp | Phe | Phe | Lys | Ser | Ala | Met | Pro | Glu | Gly | Tyr | Val | Gln | Glu | Arg |
| | | | | 85 | | | | | 90 | | | | | 95 | |
| Thr | Ile | Phe | Phe | Lys | Asp | Asp | Gly | Asn | Tyr | Lys | Thr | Arg | Ala | Glu | Val |
| | | | 100 | | | | | 105 | | | | | 110 | | |
| Lys | Phe | Glu | Gly | Asp | Thr | Leu | Val | Asn | Arg | Ile | Glu | Leu | Lys | Gly | Ile |
| | | | | 115 | | | | | 120 | | | | | 125 | |
| Asp | Phe | Lys | Glu | Asp | Gly | Asn | Ile | Leu | Gly | His | Lys | Leu | Glu | Tyr | Asn |
| | | 130 | | | | | 135 | | | | | 140 | | | |
| Ala | Ile | Ser | Asp | Asn | Val | Tyr | Ile | Thr | Ala | Asp | Lys | Gln | Lys | Asn | Gly |
| 145 | | | | | 150 | | | | | 155 | | | | | 160 |
| Ile | Lys | Ala | Asn | Phe | Lys | Ile | Arg | His | Asn | Ile | Glu | Asp | Gly | Ser | Val |
| | | | | 165 | | | | | 170 | | | | | 175 | |
| Gln | Leu | Ala | Asp | His | Tyr | Gln | Gln | Asn | Thr | Pro | Ile | Gly | Asp | Gly | Pro |
| | | | 180 | | | | | 185 | | | | | 190 | | |
| Val | Leu | Leu | Pro | Asp | Asn | His | Tyr | Leu | Ser | Thr | Gln | Ser | Ala | Leu | Ser |
| | | | | 195 | | | | | 200 | | | | | 205 | |
| Lys | Asp | Pro | Asn | Glu | Lys | Arg | Asp | His | Met | Val | Leu | Leu | Glu | Phe | Val |
| | | 210 | | | | | 215 | | | | | 220 | | | |
| Thr | Ala | Ala | Gly | Ile | Thr | Leu | Gly | Met | Asp | Glu | Leu | Tyr | Lys | | |
| 225 | | | | | 230 | | | | | 235 | | | | | |

```
<210> SEQ ID NO 23
<211> LENGTH: 714
<212> TYPE: DNA
<213> ORGANISM: artificial
<220> FEATURE:
<223> OTHER INFORMATION: ECFP (65S, 72A, 145A, 148G) nucleotide sequence

<400> SEQUENCE: 23
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgagctgggg cgtgcagtgc ttcgcccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca acgccatcag cggcaacgtc tatatcaccg ccgacaagca gaagaacggc     480
atcaaggcca acttcaagat ccgccacaac atcgaggacg gcagcgtgca gctcgccgac     540
```

```
cactaccagc agaacacccc catcggcgac ggccccgtgc tgctgcccga caaccactac    600
ctgagcaccc agtccgccct gagcaaagac cccaacgaga agcgcgatca catggtcctg    660
ctggagttcg tgaccgccgc cgggatcact ctcggcatgg acgagctgta caag           714
```

```
<210> SEQ ID NO 24
<211> LENGTH: 238
<212> TYPE: PRT
<213> ORGANISM: artificial
<220> FEATURE:
<223> OTHER INFORMATION: ECFP (65S, 72A, 145A, 148G) amino acid sequence

<400> SEQUENCE: 24
```

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Ala Ile Ser Gly Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

```
<210> SEQ ID NO 25
<211> LENGTH: 714
<212> TYPE: DNA
<213> ORGANISM: artificial
<220> FEATURE:
<223> OTHER INFORMATION: ECFP (65S, 72A, 145A, 148S) nucleotide sequence

<400> SEQUENCE: 25
```

```
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc    120
aagctgaccc tgaagttcat ctgcaccacc ggcaagctgc ccgtgccctg gcccaccctc    180
gtgaccaccc tgagctgggg cgtgcagtgc ttcgcccgct accccgacca catgaagcag    240
```

```
cacgacttct tcaagtccgc catgcccgaa ggctacgtcc aggagcgcac catcttcttc      300
aaggacgacg gcaactacaa gacccgcgcc gaggtgaagt tcgagggcga cacccttggtg      360 aaccgcatcg agctgaaggg catcgacttc aaggaggacg gcaacatcct ggggcacaag      420
ctggagtaca cgccatcag ctccaacgtc tatatcaccg ccgacaagca gaagaacggc       480
atcaaggcca acttcaagat ccgccacaac atcgaggacg gcagcgtgca gctcgccgac      540
cactaccagc agaacacccc catcggcgac ggccccgtgc tgctgcccga caaccactac      600
ctgagcaccc agtccgccct gagcaaagac cccaacgaga gcgcgatca catggtcctg      660 ctggagttcg tgaccgccgc cgggatcact ctcggcatgg acgagctgta caag            714
```

```
<210> SEQ ID NO 26
<211> LENGTH: 238
<212> TYPE: PRT
<213> ORGANISM: artificial
<220> FEATURE:
<223> OTHER INFORMATION: ECFP (65S, 72A, 145A, 148S) amino acid sequence

<400> SEQUENCE: 26
```

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Ala Ile Ser Ser Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

```
<210> SEQ ID NO 27
<211> LENGTH: 714
<212> TYPE: DNA
<213> ORGANISM: artificial
<220> FEATURE:
<223> OTHER INFORMATION: ECFP (65S, 72A, 148D, 206K) nucleotide sequence
```

-continued

<400> SEQUENCE: 27

```
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg cccacccctc     180
gtgaccaccc tgagctgggg cgtgcagtgc ttcgcccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacatcag cgacaacgtc tatatcaccg ccgacaagca gaagaacggc     480
atcaaggcca acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccaagct gagcaaagac cccaacgaga gcgcgatca catggtcctg      660 ctggagttcg tgaccgccgc cgggatcact ctcggcatgg acgagctgta caag            714
```

<210> SEQ ID NO 28
<211> LENGTH: 238
<212> TYPE: PRT
<213> ORGANISM: artificial
<220> FEATURE:
<223> OTHER INFORMATION: ECFP (65S, 72A, 148D, 206K) amino acid sequence

<400> SEQUENCE: 28

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser Asp Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Lys Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
```

<210> SEQ ID NO 29
<211> LENGTH: 714
<212> TYPE: DNA
<213> ORGANISM: artificial
<220> FEATURE:
<223> OTHER INFORMATION: ECFP (65S, 72A, 148G, 206K) nucleotide sequence

<400> SEQUENCE: 29

```
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg cccaccctc    180
gtgaccaccc tgagctgggg cgtgcagtgc ttcgcccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacatcag cggcaacgtc tatatcaccg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccaagct gagcaaagac cccaacgaga gcgcgatca catggtcctg   660
ctggagttcg tgaccgccgc cgggatcact ctcggcatgg acgagctgta caag         714
```

<210> SEQ ID NO 30
<211> LENGTH: 238
<212> TYPE: PRT
<213> ORGANISM: artificial
<220> FEATURE:
<223> OTHER INFORMATION: ECFP (65S, 72A, 148G, 206K) amino acid sequence

<400> SEQUENCE: 30

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser Gly Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

```
Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Lys Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 31
<211> LENGTH: 714
<212> TYPE: DNA
<213> ORGANISM: artificial
<220> FEATURE:
<223> OTHER INFORMATION: ECFP (65S, 72A, 148S, 206K) nucleotide sequence

<400> SEQUENCE: 31
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgagctgggg cgtgcagtgc ttcgcccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacatcag ctccaacgtc tatatcaccg ccgacaagca gaagaacggc     480
atcaaggcca acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccaagct gagcaaagac cccaacgaga gcgcgatca catggtcctg     660 ctggagttcg tgaccgccgc cgggatcact ctcggcatgg acgagctgta caag            714

<210> SEQ ID NO 32
<211> LENGTH: 238
<212> TYPE: PRT
<213> ORGANISM: artificial
<220> FEATURE:
<223> OTHER INFORMATION: ECFP (65S, 72A, 148S, 206K) amino acid sequence

<400> SEQUENCE: 32

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125
```

```
Asp Phe Lys Glu Asp Gly Asn Ile Leu Gly His Lys Leu Glu Tyr Asn
            130                 135                 140

Tyr Ile Ser Ser Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Lys Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 33
<211> LENGTH: 714
<212> TYPE: DNA
<213> ORGANISM: artificial
<220> FEATURE:
<223> OTHER INFORMATION: ECFP (65S, 72A, 206K) nucleotide sequence

<400> SEQUENCE: 33

| | | |
|---|---|---|
| gtgagcaagg gcgaggagct gttcaccggg gtggtgccca tcctggtcga gctggacggc | 60 |
| gacgtaaacg gccacaagtt cagcgtgtcc ggcgagggcg agggcgatgc cacctacggc | 120 |
| aagctgaccc tgaagttcat ctgcaccacc ggcaagctgc ccgtgccctg gcccaccctc | 180 |
| gtgaccaccc tgagctgggg cgtgcagtgc ttcgcccgct accccgacca catgaagcag | 240 |
| cacgacttct tcaagtccgc catgcccgaa ggctacgtcc aggagcgcac catcttcttc | 300 |
| aaggacgacg gcaactacaa gacccgcgcc gaggtgaagt tcgagggcga caccctggtg | 360 |
| aaccgcatcg agctgaaggg catcgacttc aaggaggacg gcaacatcct ggggcacaag | 420 |
| ctggagtaca actacatcag ccacaacgtc tatatcaccg ccgacaagca gaagaacggc | 480 |
| atcaaggcca acttcaagat ccgccacaac atcgaggacg gcagcgtgca gctcgccgac | 540 |
| cactaccagc agaacacccc catcggcgac ggccccgtgc tgctgcccga caaccactac | 600 |
| ctgagcaccc agtccaagct gagcaaagac cccaacgaga gcgcgatca catggtcctg | 660 |
| ctggagttcg tgaccgccgc cgggatcact ctcggcatgg acgagctgta caag | 714 |

<210> SEQ ID NO 34
<211> LENGTH: 238
<212> TYPE: PRT
<213> ORGANISM: artificial
<220> FEATURE:
<223> OTHER INFORMATION: ECFP (65S, 72A, 206K) amino acid sequence

<400> SEQUENCE: 34

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ala Arg Tyr Pro Asp His Met Lys Gln
```

```
                65                  70                  75                  80
His Asp Phe Phe Lys Ser Ala Met Pro Glu Gly Tyr Val Gln Glu Arg
                    85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Ile Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Lys Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 35
<211> LENGTH: 29
<212> TYPE: DNA
<213> ORGANISM: artificial
<220> FEATURE:
<223> OTHER INFORMATION: forward primer

<400> SEQUENCE: 35
aaggcgccgt gagcaagggc gaggagctg                                       29

<210> SEQ ID NO 36
<211> LENGTH: 30
<212> TYPE: DNA
<213> ORGANISM: artificial
<220> FEATURE:
<223> OTHER INFORMATION: reverse primer

<400> SEQUENCE: 36
ttaagcttac ttgtacagct cgtccatgcc                                      30

<210> SEQ ID NO 37
<211> LENGTH: 31
<212> TYPE: DNA
<213> ORGANISM: artificial
<220> FEATURE:
<223> OTHER INFORMATION: 148Gf nucleotide sequence

<400> SEQUENCE: 37
caactacatc agcggcaacg tctatatcac c                                    31

<210> SEQ ID NO 38
<211> LENGTH: 31
<212> TYPE: DNA
<213> ORGANISM: artificial
<220> FEATURE:
<223> OTHER INFORMATION: 148Gr nucleotide sequence

<400> SEQUENCE: 38
ggtgatatag acgttgccgc tgatgtagtt g                                    31

```
<210> SEQ ID NO 39
<211> LENGTH: 31
<212> TYPE: DNA
<213> ORGANISM: artificial
<220> FEATURE:
<223> OTHER INFORMATION: 148Sf nucleotide sequence

<400> SEQUENCE: 39
caactacatc agctccaacg tctatatcac c                              31

<210> SEQ ID NO 40
<211> LENGTH: 31
<212> TYPE: DNA
<213> ORGANISM: artificial
<220> FEATURE:
<223> OTHER INFORMATION: 148Sr nucleotide sequence

<400> SEQUENCE: 40
ggtgatatag acgttggagc tgatgtagtt g                              31

<210> SEQ ID NO 41
<211> LENGTH: 31
<212> TYPE: DNA
<213> ORGANISM: artificial
<220> FEATURE:
<223> OTHER INFORMATION: 148Df nucleotide sequence

<400> SEQUENCE: 41
caactacatc agcgacaacg tctatatcac c                              31

<210> SEQ ID NO 42
<211> LENGTH: 31
<212> TYPE: DNA
<213> ORGANISM: artificial
<220> FEATURE:
<223> OTHER INFORMATION: 148Dr nucleotide sequence

<400> SEQUENCE: 42
ggtgatatag acgttgtcgc tgatgtagtt g                              31

<210> SEQ ID NO 43
<211> LENGTH: 31
<212> TYPE: DNA
<213> ORGANISM: artificial
<220> FEATURE:
<223> OTHER INFORMATION: 148Rf nucleotide sequence

<400> SEQUENCE: 43
caactacatc agccgcaacg tctatatcac c                              31

<210> SEQ ID NO 44
<211> LENGTH: 31
<212> TYPE: DNA
<213> ORGANISM: artificial
<220> FEATURE:
<223> OTHER INFORMATION: 148Rr nucleotide sequence

<400> SEQUENCE: 44
ggtgatatag acgttgcggc tgatgtagtt g                              31

<210> SEQ ID NO 45
<211> LENGTH: 31
<212> TYPE: DNA
<213> ORGANISM: artificial
<220> FEATURE:
```

```
<223> OTHER INFORMATION: 148Nf nucleotide sequence

<400> SEQUENCE: 45
gtacaactac atctccaaca acgtctatat c                                31

<210> SEQ ID NO 46
<211> LENGTH: 31
<212> TYPE: DNA
<213> ORGANISM: artificial
<220> FEATURE:
<223> OTHER INFORMATION: 148Nr nucleotide sequence

<400> SEQUENCE: 46
gatatagacg ttgttggaga tgtagttgta c                                31

<210> SEQ ID NO 47
<211> LENGTH: 31
<212> TYPE: DNA
<213> ORGANISM: artificial
<220> FEATURE:
<223> OTHER INFORMATION: 148Ef nucleotide sequence

<400> SEQUENCE: 47
caactacatc agcgagaacg tctatatcac c                                31

<210> SEQ ID NO 48
<211> LENGTH: 31
<212> TYPE: DNA
<213> ORGANISM: artificial
<220> FEATURE:
<223> OTHER INFORMATION: 148Er nucleotide sequence

<400> SEQUENCE: 48
ggtgatatag acgttctcgc tgatgtagtt g                                31

<210> SEQ ID NO 49
<211> LENGTH: 31
<212> TYPE: DNA
<213> ORGANISM: artificial
<220> FEATURE:
<223> OTHER INFORMATION: 65Sf nucleotide sequence

<400> SEQUENCE: 49
cgtgaccacc ctgagctggg gcgtgcagtg c                                31

<210> SEQ ID NO 50
<211> LENGTH: 31
<212> TYPE: DNA
<213> ORGANISM: artificial
<220> FEATURE:
<223> OTHER INFORMATION: 65Sr nucleotide sequence

<400> SEQUENCE: 50
gcactgcacg ccccagctca gggtggtcac g                                31

<210> SEQ ID NO 51
<211> LENGTH: 31
<212> TYPE: DNA
<213> ORGANISM: artificial
<220> FEATURE:
<223> OTHER INFORMATION: 72Af nucleotide sequence

<400> SEQUENCE: 51
cgtgcagtgc ttcgcccgct accccgacca c                                31
```

<210> SEQ ID NO 52
<211> LENGTH: 31
<212> TYPE: DNA
<213> ORGANISM: artificial
<220> FEATURE:
<223> OTHER INFORMATION: 72Ar nucleotide sequence

<400> SEQUENCE: 52
gtggtcgggg tagcgggcga agcactgcac g                           31

<210> SEQ ID NO 53
<211> LENGTH: 31
<212> TYPE: DNA
<213> ORGANISM: artificial
<220> FEATURE:
<223> OTHER INFORMATION: 145Af nucleotide sequence

<400> SEQUENCE: 53
gctggagtac aacgccatca gcgacaacgt c                           31

<210> SEQ ID NO 54
<211> LENGTH: 31
<212> TYPE: DNA
<213> ORGANISM: artificial
<220> FEATURE:
<223> OTHER INFORMATION: 145Ar nucleotide sequence

<400> SEQUENCE: 54
gacgttgtcg ctgatggcgt tgtactccag c                           31

<210> SEQ ID NO 55
<211> LENGTH: 34
<212> TYPE: DNA
<213> ORGANISM: artificial
<220> FEATURE:
<223> OTHER INFORMATION: 206Kf nucleotide sequence

<400> SEQUENCE: 55
cctgagcacc cagtccaagc tgagcaaaga cccc                        34

<210> SEQ ID NO 56
<211> LENGTH: 34
<212> TYPE: DNA
<213> ORGANISM: artificial
<220> FEATURE:
<223> OTHER INFORMATION: 206Kr nucleotide sequence

<400> SEQUENCE: 56
ggggtctttg ctcagcttgg actgggtgct cagg                        34

<210> SEQ ID NO 57
<211> LENGTH: 714
<212> TYPE: DNA
<213> ORGANISM: artificial
<220> FEATURE:
<223> OTHER INFORMATION: ECFP (148A) nucleotide sequence

<400> SEQUENCE: 57
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgacctgggg cgtgcagtgc ttcagccgct accccgacca catgaagcag     240
cacgacttct tcaagtccgc catgcccgaa ggctacgtcc aggagcgcac catcttcttc     300

-continued

```
aaggacgacg gcaactacaa gacccgcgcc gaggtgaagt tcgagggcga cacccTggtg    360
aaccgcatcg agctgaaggg catcgacttc aaggaggacg gcaacatcct ggggcacaag    420
ctggagtaca actacatcag cgccaacgtc tatatcaccg ccgacaagca gaagaacggc    480
atcaaggcca acttcaagat ccgccacaac atcgaggacg gcagcgtgca gctcgccgac    540
cactaccagc agaacacccc catcggcgac ggccccgtgc tgctgcccga caaccactac    600
ctgagcaccc agtccgccct gagcaaagac cccaacgaga gcgcgatca catggtcctg     660 ctggagttcg tgaccgccgc cgggatcact ctcggcatgg acgagctgta caag          714
```

<210> SEQ ID NO 58
<211> LENGTH: 238
<212> TYPE: PRT
<213> ORGANISM: artificial
<220> FEATURE:
<223> OTHER INFORMATION: ECFP (148A) amino acid sequence

<400> SEQUENCE: 58

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser Ala Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 59
<211> LENGTH: 714
<212> TYPE: DNA
<213> ORGANISM: artificial
<220> FEATURE:
<223> OTHER INFORMATION: ECFP (65S, 148A) nucleotide sequence

<400> SEQUENCE: 59

```
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg cccacccctc   180
gtgaccaccc tgagctgggg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga cacccctggtg   360 aaccgcatcg agctgaaggg catcgacttc aaggaggacg gcaacatcct ggggcacaag   420
ctggagtaca actacatcag cgccaacgtc tatatcaccg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca catggtcctg   660 ctggagttcg tgaccgccgc cgggatcact ctcggcatgg acgagctgta caag          714
```

<210> SEQ ID NO 60
<211> LENGTH: 238
<212> TYPE: PRT
<213> ORGANISM: artificial
<220> FEATURE:
<223> OTHER INFORMATION: ECFP (65S, 148A) amino acid sequence

<400> SEQUENCE: 60

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser Ala Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 61
<211> LENGTH: 714
<212> TYPE: DNA
<213> ORGANISM: artificial
<220> FEATURE:
<223> OTHER INFORMATION: ECFP (72A, 145A, 148A) nucleotide sequence

<400> SEQUENCE: 61

```
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg cccaccctc      180
gtgaccaccc tgacctgggg cgtgcagtgc ttcgcccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca acgccatcag cgccaacgtc tatatcaccg ccgacaagca gaagaacggc     480
atcaaggcca acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg      660
ctggagttcg tgaccgccgc cgggatcact ctcggcatgg acgagctgta caag           714
```

<210> SEQ ID NO 62
<211> LENGTH: 238
<212> TYPE: PRT
<213> ORGANISM: artificial
<220> FEATURE:
<223> OTHER INFORMATION: ECFP (72A, 145A, 148A) amino acid sequence

<400> SEQUENCE: 62

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Ala Ile Ser Ala Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190
```

Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
        210                 215                 220

Thr Ala Ala Gly Ile Thr Leu Gly Met Asp Glu Leu Tyr Lys
225                 230                 235

<210> SEQ ID NO 63
<211> LENGTH: 714
<212> TYPE: DNA
<213> ORGANISM: artificial
<220> FEATURE:
<223> OTHER INFORMATION: ECFP (65S, 72A, 145A, 148A) nucleotide sequence

<400> SEQUENCE: 63
gtgagcaagg gcgaggagct gttcaccggg gtggtgccca tcctggtcga gctggacggc      60
gacgtaaacg ccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgagctgggg cgtgcagtgc ttcgcccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca acgccatcag cgccaacgtc tatatcaccg ccgacaagca gaagaacggc     480
atcaaggcca acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg     660 ctggagttcg tgaccgccgc cgggatcact ctcggcatgg acgagctgta caag           714

<210> SEQ ID NO 64
<211> LENGTH: 238
<212> TYPE: PRT
<213> ORGANISM: artificial
<220> FEATURE:
<223> OTHER INFORMATION: ECFP (65S, 72A, 145A, 148A) amino acid sequence

<400> SEQUENCE: 64

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn

```
                130              135              140
Ala Ile Ser Ala Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 65
<211> LENGTH: 714
<212> TYPE: DNA
<213> ORGANISM: artificial
<220> FEATURE:
<223> OTHER INFORMATION: ECFP (65S, 72A, 148A, 206K) nucleotide sequence

<400> SEQUENCE: 65
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgagctgggg cgtgcagtgc ttcgcccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacatcag cgccaacgtc tatatcaccg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccaagct gagcaaagac cccaacgaga gcgcgatca  catggtcctg   660 ctggagttcg tgaccgccgc cgggatcact ctcggcatgg acgagctgta caag          714

<210> SEQ ID NO 66
<211> LENGTH: 238
<212> TYPE: PRT
<213> ORGANISM: artificial
<220> FEATURE:
<223> OTHER INFORMATION: ECFP (65S, 72A, 148A, 206K) amino acid sequence

<400> SEQUENCE: 66

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Leu
        50                  55                  60

Ser Trp Gly Val Gln Cys Phe Ala Arg Tyr Pro Asp His Met Lys Gln
65                  70                  75                  80
```

```
His Asp Phe Phe Lys Ser Ala Met Pro Glu Gly Tyr Val Gln Glu Arg
            85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
            130                 135                 140

Tyr Ile Ser Ala Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
            165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Lys Leu Ser
            195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235

<210> SEQ ID NO 67
<211> LENGTH: 31
<212> TYPE: DNA
<213> ORGANISM: artificial
<220> FEATURE:
<223> OTHER INFORMATION: 148Af nucleotide sequence

<400> SEQUENCE: 67
caactacatc agcgccaacg tctatatcac c                              31

<210> SEQ ID NO 68
<211> LENGTH: 31
<212> TYPE: DNA
<213> ORGANISM: artificial
<220> FEATURE:
<223> OTHER INFORMATION: 148Ar nucleotide sequence

<400> SEQUENCE: 68
ggtgatatag acgttggcgc tgatgtagtt g                              31

<210> SEQ ID NO 69
<211> LENGTH: 75
<212> TYPE: DNA
<213> ORGANISM: artificial
<220> FEATURE:
<223> OTHER INFORMATION: polyhistidine sequence and a TEV protease
      clivage site sequence

<400> SEQUENCE: 69
atgtcgtact accatcacca tcaccatcac gattacgata tcccaacgac cgaaaacctg   60
tattttcagg gcgcc                                                    75

<210> SEQ ID NO 70
<211> LENGTH: 25
<212> TYPE: PRT
<213> ORGANISM: artificial
<220> FEATURE:
<223> OTHER INFORMATION: polyhistidine sequence and a TEV protease
      clivage site sequence

<400> SEQUENCE: 70
```

```
Met Ser Tyr Tyr His His His His His Asp Tyr Asp Ile Pro Thr
1               5                   10                  15

Thr Glu Asn Leu Tyr Phe Gln Gly Ala
            20              25
```

<210> SEQ ID NO 71
<211> LENGTH: 714
<212> TYPE: DNA
<213> ORGANISM: artificial
<220> FEATURE:
<223> OTHER INFORMATION: ECFP (148E) nucleotide sequence

<400> SEQUENCE: 71

```
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacctgggg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacatcag cgaaaacgtc tatatcaccg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca  catggtcctg   660
ctggagttcg tgaccgccgc cgggatcact ctcggcatgg acgagctgta caag          714
```

<210> SEQ ID NO 72
<211> LENGTH: 238
<212> TYPE: PRT
<213> ORGANISM: artificial
<220> FEATURE:
<223> OTHER INFORMATION: ECFP (148E) amino acid sequence

<400> SEQUENCE: 72

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser Glu Asn Val Tyr Ile Thr Ala Asp Lys Gln Lys Asn Gly
```

```
                145                 150                 155                 160
Ile Lys Ala Asn Phe Lys Ile Arg His Asn Ile Glu Asp Gly Ser Val
                    165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Ser Thr Gln Ser Ala Leu Ser
                195                 200                 205

Lys Asp Pro Asn Glu Lys Arg Asp His Met Val Leu Leu Glu Phe Val
            210                 215                 220

Thr Ala Ala Gly Ile Thr Leu Gly Met Asp Glu Leu Tyr Lys
225                 230                 235

<210> SEQ ID NO 73
<211> LENGTH: 714
<212> TYPE: DNA
<213> ORGANISM: artificial
<220> FEATURE:
<223> OTHER INFORMATION: ECFP (65S, 148E) nucleotide sequence

<400> SEQUENCE: 73
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgagctgggg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacatcag cgaaaacgtc tatatcaccg ccgacaagca gaagaacggc     480
atcaaggcca acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg     660 ctggagttcg tgaccgccgc cgggatcact ctcggcatgg acgagctgta caag           714

<210> SEQ ID NO 74
<211> LENGTH: 238
<212> TYPE: PRT
<213> ORGANISM: artificial
<220> FEATURE:
<223> OTHER INFORMATION: ECFP (65S, 148E) amino acid sequence

<400> SEQUENCE: 74

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Leu
        50                  55                  60

Ser Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95
```

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
        130                 135                 140

Tyr Ile Ser Glu Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
        210                 215                 220

Thr Ala Ala Gly Ile Thr Leu Gly Met Asp Glu Leu Tyr Lys
225                 230                 235

<210> SEQ ID NO 75
<211> LENGTH: 714
<212> TYPE: DNA
<213> ORGANISM: artificial
<220> FEATURE:
<223> OTHER INFORMATION: ECFP (65S, 148D) nucleotide sequence

<400> SEQUENCE: 75
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg cccaccctc     180 gtgaccaccc tgagctgggg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga cacccctggtg    360 aaccgcatcg agctgaaggg catcgacttc aaggaggacg gcaacatcct ggggcacaag     420
ctggagtaca actacatcag cgacaacgtc tatatcaccg ccgacaagca gaagaacggc     480
atcaaggcca acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg      660 ctggagttcg tgaccgccgc cgggatcact ctcggcatgg acgagctgta caag            714

<210> SEQ ID NO 76
<211> LENGTH: 238
<212> TYPE: PRT
<213> ORGANISM: artificial
<220> FEATURE:
<223> OTHER INFORMATION: ECFP (65S, 148D) amino acid sequence

<400> SEQUENCE: 76

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

```
Thr Gly Lys Leu Pro Val Pro Trp Pro Thr Leu Val Thr Thr Leu
    50              55                  60

Ser Trp Gly Val Gln Cys Phe Ser Arg Tyr Pro Asp His Met Lys Gln
65              70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser Asp Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 77
<211> LENGTH: 28
<212> TYPE: DNA
<213> ORGANISM: artificial
<220> FEATURE:
<223> OTHER INFORMATION: TagRFPf nucleotide sequence

<400> SEQUENCE: 77
attagagctc atggtgtcta agggcgaa                                      28

<210> SEQ ID NO 78
<211> LENGTH: 30
<212> TYPE: DNA
<213> ORGANISM: artificial
<220> FEATURE:
<223> OTHER INFORMATION: TagFRPr nucleotide sequence

<400> SEQUENCE: 78
ataatgaatt cttaattaag tttgtgcccc                                    30

<210> SEQ ID NO 79
<211> LENGTH: 714
<212> TYPE: DNA
<213> ORGANISM: artificial
<220> FEATURE:
<223> OTHER INFORMATION: ECFP (26R, 65S, 148G, 164H, 206K) nucleotide
      sequence

<400> SEQUENCE: 79
gtgagcaagg gcgaggagct gttcaccggg gtggtgccca tcctggtcga gctggacggc    60
gacgtaaacg gccacaggtt cagcgtgtcc ggcgagggcg agggcgatgc cacctacggc   120
aagctgaccc tgaagttcat ctgcaccacc ggcaagctgc ccgtgccctg cccaccctc    180 gtgaccaccc tgagctgggg cgtgcagtgc ttcagccgct accccgacca catgaagcag   240

-continued

```
cacgacttct tcaagtccgc catgcccgaa ggctacgtcc aggagcgtac catcttcttc    300
aaggacgacg gcaactacaa gacccgcgcc gaggtgaagt tcgagggcga caccctggtg    360
aaccgcatcg agctgaaggg catcgacttc aaggaggacg gcaacatcct ggggcacaag    420
ctggagtaca actacatcag cggcaacgtc tatatcaccg ccgacaagca gaagaacggc    480
atcaaggccc acttcaagat ccgccacaac atcgaggacg gcagcgtgca gctcgccgac    540
cactaccagc agaacacccc catcggcgac ggccccgtgc tgctgcccga caaccactac    600
ctgagcaccc agtccaagct gagcaaagac cccaacgaga gcgcgatca catggtcctg    660 ctggagttcg tgaccgccgc cgggatcact ctcggcatgg acgagctgta caag          714
```

<210> SEQ ID NO 80
<211> LENGTH: 238
<212> TYPE: PRT
<213> ORGANISM: artificial
<220> FEATURE:
<223> OTHER INFORMATION: ECFP (26R, 65S, 148G, 164H, 206K) amino acid sequence

<400> SEQUENCE: 80

```
Val Ser Lys Gly Glu Glu Leu Phe Thr Gly Val Val Pro Ile Leu Val
1               5                   10                  15

Glu Leu Asp Gly Asp Val Asn Gly His Arg Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser Gly Asn Val Tyr Ile Thr Ala Asp Lys Gln Lys Asn Gly
145                 150                 155                 160

Ile Lys Ala His Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Lys Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 81
<211> LENGTH: 681
<212> TYPE: DNA
<213> ORGANISM: artificial
<220> FEATURE:

<223> OTHER INFORMATION: ECFP (26R, 65S, 148G, 164H, 206K) nucleotide
      sequence truncated in C-terminal

<400> SEQUENCE: 81

```
gtgagcaagg gcgaggagct gttcaccggg gtggtgccca tcctggtcga gctggacggc    60
gacgtaaacg gccacaggtt cagcgtgtcc ggcgagggcg agggcgatgc cacctacggc   120
aagctgaccc tgaagttcat ctgcaccacc ggcaagctgc ccgtgccctg cccacccctc   180
gtgaccaccc tgagctgggg cgtgcagtgc ttcagccgct accccgacca catgaagcag   240
cacgacttct tcaagtccgc catgcccgaa ggctacgtcc aggagcgtac catcttcttc   300
aaggacgacg gcaactacaa gacccgcgcc gaggtgaagt tcgagggcga cacccctggtg  360
aaccgcatcg agctgaaggg catcgacttc aaggaggacg gcaacatcct ggggcacaag   420
ctggagtaca actacatcag cggcaacgtc tatatcaccg ccgacaagca gaagaacggc   480
atcaaggccc acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccaagct gagcaaagac cccaacgaga gcgcgatca catggtcctg    660
ctggagttcg tgaccgccgc c                                             681
```

<210> SEQ ID NO 82
<211> LENGTH: 227
<212> TYPE: PRT
<213> ORGANISM: artificial
<220> FEATURE:
<223> OTHER INFORMATION: ECFP (26R, 65S, 148G, 164H, 206K) amino acid
      sequence truncated in C-terminal

<400> SEQUENCE: 82

```
Val Ser Lys Gly Glu Glu Leu Phe Thr Gly Val Val Pro Ile Leu Val
1               5                   10                  15

Glu Leu Asp Gly Asp Val Asn Gly His Arg Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser Gly Asn Val Tyr Ile Thr Ala Asp Lys Gln Lys Asn Gly
145                 150                 155                 160

Ile Lys Ala His Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Lys Leu Ser
        195                 200                 205
```

```
Lys Asp Pro Asn Glu Lys Arg Asp His Met Val Leu Leu Glu Phe Val
    210                 215                 220
Thr Ala Ala
225
```

UNITED STATES PATENT AND TRADEMARK OFFICE
CERTIFICATE OF CORRECTION

| | |
|---|---|
| PATENT NO. | : 9,567,374 B2 |
| APPLICATION NO. | : 14/126183 |
| DATED | : February 14, 2017 |
| INVENTOR(S) | : Hélène Pasquier et al. |

It is certified that error appears in the above-identified patent and that said Letters Patent is hereby corrected as shown below:

On the Title Page

The Assignees' names should read as follows:

(73) Assignees: --CENTRE NATIONAL DE LA RECHERCHE SCIENTIFIQUE, Paris (FR); UNIVERSITE PARIS-SUD 11, Orsay (FR)--

Signed and Sealed this
Tenth Day of October, 2017

Joseph Matal
*Performing the Functions and Duties of the*
*Under Secretary of Commerce for Intellectual Property and*
*Director of the United States Patent and Trademark Office*